US011426442B2

(12) United States Patent
Garruto et al.

(10) Patent No.: US 11,426,442 B2
(45) Date of Patent: *Aug. 30, 2022

(54) COMPOSITIONS AND METHODS FOR INVASIVE AND NON-INVASIVE PROCEDURAL SKINCARE

(71) Applicant: Alastin Skincare, Inc., Carlsbad, CA (US)

(72) Inventors: John A. Garruto, Encinitas, CA (US); Alan David Widgerow, Irvine, CA (US)

(73) Assignee: ALASTIN SKINCARE, INC., Carlsbad, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/870,643

(22) Filed: May 8, 2020

(65) Prior Publication Data

US 2020/0338154 A1 Oct. 29, 2020

Related U.S. Application Data

(63) Continuation of application No. 16/293,467, filed on Mar. 5, 2019, now Pat. No. 10,688,147, which is a
(Continued)

(51) Int. Cl.
| | | |
|---|---|---|
| *A61K 38/08* | (2019.01) | |
| *A61K 8/58* | (2006.01) | |
| *A61K 31/01* | (2006.01) | |
| *A61K 31/047* | (2006.01) | |
| *A61K 31/231* | (2006.01) | |
| *A61K 31/47* | (2006.01) | |
| *A61K 31/685* | (2006.01) | |
| *A61K 31/695* | (2006.01) | |
| *A61K 31/74* | (2006.01) | |
| *A61K 8/26* | (2006.01) | |
| *A61K 8/37* | (2006.01) | |
| *A61K 8/41* | (2006.01) | |

(Continued)

(52) U.S. Cl.
CPC .............. *A61K 38/08* (2013.01); *A61K 8/26* (2013.01); *A61K 8/37* (2013.01); *A61K 8/416* (2013.01); *A61K 8/42* (2013.01); *A61K 8/498* (2013.01); *A61K 8/4973* (2013.01); *A61K 8/553* (2013.01); *A61K 8/585* (2013.01); *A61K 8/602* (2013.01); *A61K 8/64* (2013.01); *A61K 8/891* (2013.01); *A61K 8/894* (2013.01); *A61K 8/97* (2013.01); *A61K 9/0014* (2013.01); *A61K 31/01* (2013.01); *A61K 31/047* (2013.01); *A61K 31/16* (2013.01); *A61K 31/231* (2013.01); *A61K 31/353* (2013.01); *A61K 31/47* (2013.01); *A61K 31/685* (2013.01); *A61K 31/695* (2013.01); *A61K 31/7048* (2013.01); *A61K 31/74* (2013.01); *A61K 36/05* (2013.01); *A61K 36/28* (2013.01); *A61K 38/06* (2013.01); *A61K 47/14* (2013.01); *A61K 47/186* (2013.01); *A61K 47/22* (2013.01); *A61K 47/24* (2013.01); *A61K 47/34* (2013.01); *A61Q 19/00* (2013.01); *A61Q 19/08* (2013.01); *A61K 2300/00* (2013.01); *A61K 2800/594* (2013.01); *A61K 2800/5922* (2013.01); *A61K 2800/75* (2013.01); *A61K 2800/884* (2013.01)

(58) Field of Classification Search
CPC .... A61Q 19/00; A61Q 19/08; A61K 2300/00; A61K 2800/884; A61K 2800/75; A61K 2800/594; A61K 280/5922; A61K 47/34; A61K 47/24; A61K 47/22; A61K 47/186; A61K 47/14; A61K 38/06; A61K 36/28; A61K 36/05; A61K 31/7048; A61K 31/353; A61K 31/16; A61K 9/0014; A61K 8/97; A61K 8/864; A61K 8/891; A61K 8/64; A61K 8/602; A61K 8/553; A61K 8/498; A61K 8/4973; A61K 8/42; A61K 8/416; A61K 8/37; A61K 8/26; A61K 31/74; A61K 31/695; A61K 31/6885; A61K 31/47; A61K 31/231; A61K 31/047; A61K 31/01; A61K 8/585; A61K 38/08

See application file for complete search history.

(56) References Cited

U.S. PATENT DOCUMENTS

| | | | |
|---|---|---|---|
| 3,299,037 | A | 1/1967 | Boissonnas et al. |
| 3,415,805 | A | 12/1968 | Siedel et al. |
| 5,534,420 | A | 7/1996 | Debono et al. |
| 5,814,610 | A | 9/1998 | Bab et al. |
| 5,993,787 | A | 11/1999 | Sun et al. |
| 6,939,854 | B2 | 9/2005 | Priestley |
| 6,974,799 | B2 | 12/2005 | Lintner |

(Continued)

FOREIGN PATENT DOCUMENTS

| | | | |
|---|---|---|---|
| CA | 2768653 | A1 | 3/2011 |
| CA | 2895387 | A1 | 7/2014 |

(Continued)

OTHER PUBLICATIONS

Yuji Shirakata, et al, Heparin-binding EGF-like Growth Factor Accelerates Keratinocyte Migration and Skin Wound Healing, 118 J Cell Sci., 2363 (Year: 2005).*

(Continued)

*Primary Examiner* — Sean M Basquill
(74) *Attorney, Agent, or Firm* — Sunit Talapatra; Foley & Lardner LLP

(57) ABSTRACT

Compositions and methods for skincare treatment are provided. The invention relates more generally to skin care treatment and more particularly, to compositions and methods for promoting healthy skin, skin regeneration, skin repair, skin bed preparation, and enhanced wound healing.

9 Claims, 28 Drawing Sheets
(25 of 28 Drawing Sheet(s) Filed in Color)

Related U.S. Application Data continuation of application No. 16/004,259, filed on Jun. 8, 2018, now Pat. No. 10,286,030, which is a continuation of application No. 15/423,530, filed on Feb. 2, 2017, now Pat. No. 10,086,035.

(60) Provisional application No. 62/303,332, filed on Mar. 3, 2016, provisional application No. 62/291,376, filed on Feb. 4, 2016.

(51) Int. Cl.

| | |
|---|---|
| *A61K 8/42* | (2006.01) |
| *A61K 8/49* | (2006.01) |
| *A61K 8/55* | (2006.01) |
| *A61K 8/60* | (2006.01) |
| *A61K 8/64* | (2006.01) |
| *A61K 8/891* | (2006.01) |
| *A61K 8/894* | (2006.01) |
| *A61K 8/97* | (2017.01) |
| *A61K 9/00* | (2006.01) |
| *A61K 31/16* | (2006.01) |
| *A61K 31/353* | (2006.01) |
| *A61K 31/7048* | (2006.01) |
| *A61K 36/05* | (2006.01) |
| *A61K 36/28* | (2006.01) |
| *A61K 38/06* | (2006.01) |
| *A61K 47/14* | (2017.01) |
| *A61K 47/18* | (2017.01) |
| *A61K 47/22* | (2006.01) |
| *A61K 47/24* | (2006.01) |
| *A61K 47/34* | (2017.01) |
| *A61Q 19/00* | (2006.01) |
| *A61Q 19/08* | (2006.01) |

(56) References Cited

U.S. PATENT DOCUMENTS

| | | | |
|---|---|---|---|
| 7,361,634 B2 | 4/2008 | Trotter et al. | |
| 7,544,375 B1 | 6/2009 | Bellin et al. | |
| 7,566,464 B2 | 7/2009 | Belfer | |
| 7,632,527 B2 | 12/2009 | Jochim et al. | |
| 7,750,115 B2 | 7/2010 | Oka et al. | |
| 7,772,196 B2 | 8/2010 | Yedgar | |
| 7,943,156 B2 | 5/2011 | Alminana et al. | |
| 8,021,695 B2 | 9/2011 | Gruber | |
| 8,025,907 B2 | 9/2011 | Belfer | |
| 8,067,370 B2 | 11/2011 | Trotter et al. | |
| 8,071,139 B2 | 12/2011 | Widgerow | |
| 8,076,312 B2 | 12/2011 | Yedgar | |
| 8,183,204 B2 | 5/2012 | Pickart | |
| 8,304,393 B2 | 11/2012 | Oka et al. | |
| 8,394,371 B2 | 3/2013 | Laurent-Applegate et al. | |
| 8,449,879 B2 | 5/2013 | Laurent-Applegate et al. | |
| 8,529,925 B2 | 9/2013 | Alexiades-Armenakas | |
| 8,530,426 B2 | 9/2013 | Lintner et al. | |
| 8,575,106 B2 | 11/2013 | Santhanam et al. | |
| 8,591,961 B2 | 11/2013 | Widgerow | |
| 8,697,656 B2 | 4/2014 | Fournial et al. | |
| 8,710,010 B2 | 4/2014 | Van Den Nestt et al. | |
| 8,710,011 B2 | 4/2014 | Garcia Sanz et al. | |
| 8,796,315 B2 | 8/2014 | Mccord | |
| 8,815,266 B2 | 8/2014 | Carreño et al. | |
| 8,901,103 B2 | 12/2014 | Yedgar | |
| 8,906,426 B2 | 12/2014 | Galderisi | |
| 8,916,539 B2 | 12/2014 | Yedgar et al. | |
| 8,946,166 B2 | 2/2015 | Garcia et al. | |
| 8,962,565 B2 | 2/2015 | Dal et al. | |
| 8,993,716 B2 | 3/2015 | Carreno et al. | |
| 9,000,033 B2 | 4/2015 | Gruber | |
| 9,067,967 B2 | 6/2015 | García et al. | |
| 9,078,903 B2 | 7/2015 | Laurent-Applegate et al. | |
| 9,144,434 B1 | 9/2015 | Rodan et al. | |
| 9,180,157 B2 | 11/2015 | Widgerow | |
| 9,180,158 B2 | 11/2015 | Widgerow | |
| 9,248,160 B1 | 2/2016 | Obagi et al. | |
| 9,265,792 B2 | 2/2016 | Riley | |
| 9,266,921 B2 | 2/2016 | Garcia et al. | |
| 9,278,122 B2 | 3/2016 | Laurent-Applegate et al. | |
| 9,315,564 B2 | 4/2016 | Serraima et al. | |
| 9,333,152 B2 | 5/2016 | Ferrer et al. | |
| 9,364,414 B2 | 6/2016 | Domloge et al. | |
| 9,376,659 B2 | 6/2016 | Rao et al. | |
| 9,408,881 B2 | 8/2016 | Gruber et al. | |
| 9,434,764 B2 | 9/2016 | Abdel-Malek et al. | |
| 9,486,409 B2 | 11/2016 | Edelson et al. | |
| 9,526,679 B2 | 12/2016 | Jang et al. | |
| 9,725,483 B2 | 8/2017 | Garcia et al. | |
| 9,834,580 B2 | 12/2017 | Abdel-Malek et al. | |
| 10,086,035 B2 | 10/2018 | Garruto et al. | |
| 10,286,030 B2 * | 5/2019 | Garruto | A61K 31/16 |
| 10,493,011 B2 | 12/2019 | Garruto et al. | |
| 10,688,147 B2 * | 6/2020 | Garruto | A61K 8/37 |
| 11,103,455 B2 | 8/2021 | Garruto et al. | |
| 2003/0166571 A1 | 9/2003 | Judd | |
| 2003/0223938 A1 | 12/2003 | Nagy et al. | |
| 2004/0043047 A1 | 3/2004 | Dumas et al. | |
| 2004/0120918 A1 | 6/2004 | Lintner et al. | |
| 2005/0063932 A1 | 3/2005 | Dilallo et al. | |
| 2005/0244483 A1 * | 11/2005 | Maruyama | A61K 48/00 424/443 |
| 2006/0110355 A1 * | 5/2006 | Blin | A61K 8/553 424/70.23 |
| 2006/0198800 A1 | 9/2006 | Dilallo et al. | |
| 2007/0048245 A1 | 3/2007 | Belfer | |
| 2007/0110731 A1 | 5/2007 | Riley | |
| 2008/0044373 A1 | 2/2008 | Ilekti et al. | |
| 2008/0107679 A1 | 5/2008 | Dilallo et al. | |
| 2008/0152606 A1 | 6/2008 | Reinhart et al. | |
| 2008/0166313 A1 | 7/2008 | Jochim et al. | |
| 2008/0166314 A1 | 7/2008 | Jochim et al. | |
| 2008/0171011 A1 | 7/2008 | Jochim et al. | |
| 2008/0171030 A1 | 7/2008 | Jochim et al. | |
| 2008/0171031 A1 | 7/2008 | Jochim et al. | |
| 2008/0175928 A1 | 7/2008 | Jochim et al. | |
| 2008/0181974 A1 | 7/2008 | Cauchard et al. | |
| 2008/0213300 A1 | 9/2008 | Jochim et al. | |
| 2009/0047226 A1 | 2/2009 | Teckenbrock et al. | |
| 2009/0186826 A1 | 7/2009 | Lintner et al. | |
| 2009/0285770 A1 | 11/2009 | Laboureau | |
| 2010/0021401 A1 | 1/2010 | Sallander | |
| 2010/0047296 A1 | 2/2010 | Banowski et al. | |
| 2010/0183723 A1 | 7/2010 | Laurent-Applegate et al. | |
| 2010/0189795 A1 | 7/2010 | Dreher | |
| 2010/0316745 A1 | 12/2010 | Pellicier et al. | |
| 2010/0322983 A1 | 12/2010 | Griffiths-Brophy et al. | |
| 2011/0005737 A1 | 1/2011 | Plata | |
| 2011/0020242 A1 | 1/2011 | Zheng et al. | |
| 2011/0052676 A1 | 3/2011 | Gruber | |
| 2011/0059907 A1 | 3/2011 | Gupta et al. | |
| 2011/0091420 A1 | 4/2011 | Liu et al. | |
| 2011/0158922 A1 | 6/2011 | Dupont et al. | |
| 2011/0177140 A1 | 7/2011 | Voegeli et al. | |
| 2012/0021029 A1 | 1/2012 | Garcia et al. | |
| 2012/0045405 A1 | 2/2012 | Gilman et al. | |
| 2012/0076842 A1 * | 3/2012 | Fournial | A61K 8/64 424/401 |
| 2012/0128755 A1 | 5/2012 | Gruber et al. | |
| 2012/0277313 A1 | 11/2012 | Kwon et al. | |
| 2013/0129691 A1 | 5/2013 | Laurent-Applegate et al. | |
| 2013/0224131 A1 | 8/2013 | Voegeli et al. | |
| 2013/0337088 A1 | 12/2013 | Widgerow | |
| 2014/0127286 A1 | 5/2014 | Doucet et al. | |
| 2014/0178315 A1 | 6/2014 | Gruber et al. | |
| 2014/0242134 A1 | 8/2014 | Khoshdel et al. | |
| 2014/0309173 A1 | 10/2014 | Dreher | |
| 2014/0315995 A1 | 10/2014 | Dreher et al. | |
| 2014/0364819 A1 | 12/2014 | Vandelden | |
| 2015/0050331 A1 | 2/2015 | Needleman | |
| 2015/0057244 A1 | 2/2015 | Yedgar et al. | |
| 2015/0157728 A1 | 6/2015 | Modi | |

(56) References Cited

U.S. PATENT DOCUMENTS

| | | | |
|---|---|---|---|
| 2015/0183823 | A1 | 7/2015 | Garcia et al. |
| 2015/0202139 | A1 | 7/2015 | Friedman |
| 2015/0209282 | A1 | 7/2015 | Chu et al. |
| 2015/0342852 | A1 | 12/2015 | Van Den Nest et al. |
| 2015/0342854 | A1 | 12/2015 | Shibuya et al. |
| 2016/0000858 | A1 | 1/2016 | Tittl et al. |
| 2016/0006543 | A1 | 1/2016 | Winstead et al. |
| 2016/0008263 | A1 | 1/2016 | Mendoza |
| 2016/0030321 | A1 | 2/2016 | Dreher |
| 2016/0058693 | A1 | 3/2016 | Widgerow |
| 2016/0058816 | A1 | 3/2016 | Widgerow |
| 2016/0075738 | A1 | 3/2016 | Ferrer et al. |
| 2017/0001438 | A1 | 1/2017 | Seto et al. |
| 2017/0081508 | A1 | 3/2017 | Daniere et al. |
| 2017/0101438 | A1 | 4/2017 | García et al. |
| 2017/0135930 | A1 | 5/2017 | Korth |
| 2017/0157014 | A1 | 6/2017 | Peschard et al. |
| 2017/0202769 | A1 | 7/2017 | Pilant |
| 2017/0281507 | A1 | 10/2017 | Idkowiak-Baldys et al. |
| 2017/0281508 | A1 | 10/2017 | Idkowiak-Baldys et al. |
| 2017/0304178 | A1 | 10/2017 | Idkowiak-Baldys et al. |
| 2018/0066016 | A1 | 3/2018 | Abdel-Malek et al. |
| 2021/0205405 | A1 | 7/2021 | Garruto et al. |

FOREIGN PATENT DOCUMENTS

| | | |
|---|---|---|
| CN | 103505377 A | 1/2014 |
| CN | 104069043 A | 10/2014 |
| CN | 104523449 A | 4/2015 |
| CN | 104523554 A | 4/2015 |
| CN | 104586695 A | 5/2015 |
| CN | 104622779 A | 5/2015 |
| CN | 103601792 B | 6/2016 |
| CN | 107375041 A | 11/2017 |
| DE | 102004050563 A1 | 4/2006 |
| DE | 102004055541 A1 | 5/2006 |
| DE | 102004057405 A1 | 6/2006 |
| DE | 102004057406 A1 | 6/2006 |
| DE | 102005063179 A1 | 9/2006 |
| DE | 102006046076 A1 | 4/2007 |
| DE | 102005056157 A1 | 5/2007 |
| DE | 102005063062 A1 | 7/2007 |
| DE | 102005063178 A1 | 7/2007 |
| DE | 102006004955 A1 | 7/2007 |
| DE | 102006020380 A1 | 10/2007 |
| DE | 102006040903 A1 | 3/2008 |
| DE | 102006041291 A1 | 3/2008 |
| DE | 102007022448 A1 | 3/2008 |
| DE | 102007024381 A1 | 3/2008 |
| DE | 102006049672 A1 | 4/2008 |
| DE | 102006049674 A1 | 4/2008 |
| DE | 102006049675 A1 | 4/2008 |
| DE | 102007022449 A1 | 4/2008 |
| DE | 102006058611 A1 | 6/2008 |
| DE | 102006060439 A1 | 6/2008 |
| DE | 102006061829 A1 | 6/2008 |
| DE | 102006062438 A1 | 7/2008 |
| DE | 102006062566 A1 | 7/2008 |
| DE | 102096062501 A1 | 7/2008 |
| DE | 102007024384 A1 | 11/2008 |
| DE | 102007031452 A1 | 1/2009 |
| DE | 102008028821 A1 | 1/2009 |
| DE | 102008061045 A1 | 10/2009 |
| DE | 102008032179 A1 | 1/2010 |
| DE | 102009026718 A1 | 4/2010 |
| DE | 102008053883 A1 | 5/2010 |
| DE | 102008053884 A1 | 5/2010 |
| DE | 102008059703 A1 | 6/2010 |
| DE | 102008061044 A1 | 6/2010 |
| DE | 102008062398 A1 | 6/2010 |
| DE | 102009037537 A1 | 6/2010 |
| DE | 102009037900 A1 | 6/2010 |
| DE | 102009039393 A1 | 6/2010 |
| DE | 102009045981 A1 | 8/2010 |
| DE | 102008061340 A1 | 9/2010 |
| DE | 102009002226 A1 | 10/2010 |
| DE | 102009002227 A1 | 10/2010 |
| DE | 102009002287 A1 | 10/2010 |
| DE | 102009017612 A1 | 10/2010 |
| DE | 102009026414 A1 | 11/2010 |
| DE | 102009027024 A1 | 12/2010 |
| DE | 102009029813 A1 | 12/2010 |
| DE | 102010027180 A1 | 5/2011 |
| DE | 102010028418 A1 | 11/2011 |
| DE | 102010063585 A1 | 6/2012 |
| DE | 102011084904 A1 | 6/2012 |
| DE | 102011087999 A1 | 9/2012 |
| DE | 102012222967 A1 | 9/2013 |
| DE | 102012222764 A1 | 10/2013 |
| EP | 2266529 A2 | 12/2010 |
| EP | 2514403 A1 | 10/2012 |
| EP | 2740484 A1 | 6/2014 |
| EP | 2792684 A1 | 10/2014 |
| FR | 2668365 A1 | 4/1992 |
| JP | 2011246372 A | 12/2011 |
| RU | 2591789 C1 | 7/2016 |
| WO | WO-9910374 A1 | 3/1999 |
| WO | WO-2005016364 A1 | 2/2005 |
| WO | WO-2005048968 A1 | 6/2005 |
| WO | WO-2006131234 A1 | 12/2006 |
| WO | WO-2007000214 A1 | 1/2007 |
| WO | WO-2007017196 A2 | 2/2007 |
| WO | WO-2007059822 A1 | 5/2007 |
| WO | WO-2007078056 A1 | 7/2007 |
| WO | WO-2008003685 A1 | 1/2008 |
| WO | WO-2008058943 A2 | 5/2008 |
| WO | WO-2008065072 A1 | 6/2008 |
| WO | WO-2008090226 A2 | 7/2008 |
| WO | WO-2008151257 A2 | 12/2008 |
| WO | WO-2008155382 A2 | 12/2008 |
| WO | WO-2008155391 A2 | 12/2008 |
| WO | WO-2009026949 A1 | 3/2009 |
| WO | WO-2009059205 A1 | 5/2009 |
| WO | WO-2009114959 A1 | 9/2009 |
| WO | WO-2010019939 A1 | 2/2010 |
| WO | WO-2010037553 A1 | 4/2010 |
| WO | WO-2010049011 A2 | 5/2010 |
| WO | WO-2010049389 A1 | 5/2010 |
| WO | WO-2010049390 A1 | 5/2010 |
| WO | WO-2010049457 A2 | 5/2010 |
| WO | WO-2010118880 A1 | 10/2010 |
| WO | WO-2011028673 A2 | 3/2011 |
| WO | WO-2012010684 A2 | 1/2012 |
| WO | WO-2012010685 A2 | 1/2012 |
| WO | WO-2012044745 A2 | 4/2012 |
| WO | WO-2012098116 A1 | 7/2012 |
| WO | WO-2012130775 A1 | 10/2012 |
| WO | WO-2012143845 A2 | 10/2012 |
| WO | WO-2012164488 A2 | 12/2012 |
| WO | WO-2013060707 A2 | 5/2013 |
| WO | WO-2013075017 A1 | 5/2013 |
| WO | WO-2013091975 A1 | 6/2013 |
| WO | WO-2013092080 A1 | 6/2013 |
| WO | WO-2014081845 A2 | 5/2014 |
| WO | WO-2014090524 A2 | 6/2014 |
| WO | WO-2014110613 A1 | 7/2014 |
| WO | WO-2014120793 A1 | 8/2014 |
| WO | WO-2014140890 A2 | 9/2014 |
| WO | WO-2016007314 A1 | 1/2016 |
| WO | WO-2016046848 A2 | 3/2016 |
| WO | WO-2016097966 A1 | 6/2016 |
| WO | WO-2017001625 A1 | 1/2017 |
| WO | WO-2017136600 A1 | 8/2017 |
| WO | WO-2017216177 A1 | 12/2017 |
| WO | WO-2019028275 A1 | 2/2019 |

OTHER PUBLICATIONS

Active Concepts. AC Dermal Respiratory Factor Advanced PF. Technical Data Sheet. (4 pgs.) (2014).

Alkemade et al. SKALP/elafin is an inducible proteinase inhibitor in human epidermal keratinocytes. Journal of Cell Science 107:2335-2342 (1994).

(56) References Cited

OTHER PUBLICATIONS

Al-Rimawi et al. Formulation and evaluation of a moisturizing day cream containing olive leaves extract. Int J Devel Res 4(10):1996-2000 (2014).
Ashcroft et al. Age-Related Changes in the Temporal and Spatial Distributions of Fibrillin and Elastin Mrnas and Proteins in Acute Cutaneous Wounds of Healthy Humans. Journal of Pathology 183:80-89 (1997).
Bani et al. Histological and Ultrastructural Effects of Ultrasound-induced Cavitation on Human Skin Adipose Tissue. Plast Reconstr Surg Glob Open 1(6):e41 (2013).
Bauters et al. Gelatinase A (MMP2) promotes marine adipogenesis. Biochimica et Biophysica Acta (BBA) General Subjects 1850:1449-1456 (2015).
Bekker et al. Relating rheological measurements to primary and secondary skin feeling when mineral-based and Fischer-Tropsch wax-based cosmetic emulsions and Jellies are applied to the skin. Int J Cosmet Sci 35(4):354-361 (2013).
Bio-Bustyl: A genuine firmness and tone concentrate for the bust; vol. 2; X055406215 (2008).
Bitto et al. Long-term IGF-I exposure decreases autophagy and cell viability. PLoS One 5(9):e12592 (2010).
Blanchevoye et al. Interaction between the Elastin Peptide VGVAPG and Human Elastin Binding Protein. J Biol Chem 288:1317-1328 (2012).
Brandner et al. Caffeine improves barrier function in male skin. International Journal of Cosmetic Science 28:343-347 (2006).
Bylka et al. Centella asiatica in cosmetology. Postepy Dermatol Alergol 30(1):46-49 (2013).
Canadian Patent Application No. 3,013,459 Office Action dated Dec. 9, 2019.
Canadian Patent Application No. 3,013,459 Office Action dated Feb. 11, 2020.
Cappellano et al. Dermal white adipose tissue renewal is regulated by the PDGFA/AKT axis. Stem Cell Investig 4:23 (2017).
Carruthers et al. Cryolipolysis and skin tightening. Dermatol Surg 40(Suppl. 12):S184-S189 (2014).
CASAS. 2019 ASAPS—Examination of healing and recovery outcomes post cosmetic surgery and non-surgical body contouring procedures with a novel topical body treatment incorporating Tripeptide and Hexapeptide (TriHex) technology. Abstract 2019.
CELLDETOX® Product brochure. Silab (3 pgs.) (2013).
Cenizo et al. LOXL as a target to increase the elastin content in adult skin: a dill extract induces the LOXL gene expression. Experimental Dermatology 15:574-581 (2006).
Chiang et al. Current concepts related to hypertrophic scarring in burn injuries. Wound Repair Regen 24(3):466-77 (2016).
Cho et al. Phosphatidylserine prevents UV-induced decrease of type I procollagen and increase of MMP-1 in dermal fibroblasts and human skin in vivo. J Lipid Res 49(6):1235-1245 (2008).
Cianfanelli et al. Ambra1 at a glance. J Cell Sci 128(11):2003-8 (2015).
Codogno et al. Atg5: more than an autophagy factor. Nature Cell Biology 8(10):1045-1048 (2006).
Database GNPD [Online]: MINTEL; anonymous: Lip Bio-Lipid Concentrate; XP055606868, retrieved from www.gnpd.com, Database accession No. 3434721 (2015).
Database GNPD [Online]: MINTEL; anonymous: Skin Softening Toner; XP055606893, retrieved from www.gnpd.com, Database accession No. 2481095 (2014).
De Backer et al. Controlling MicroRNAs to Fight Skin Senescence. Cosmetics & Toiletries Available at https://www.cosmeticsandtoiletries.com/research/biology/Controlling-MicroRNAs-to-Fight-Skin-Senescence-367698261.html (Feb. 4, 2016) (6 pgs.).
Donati et al. Epidermal Wnt/β-catenin signaling regulates adipocyte differentiation via secretion of adipogenic factors. PNAS USA 111(15):E1501-E1509. (2014).
Dow Corning 9040 Silicone Elastomer Blend product Information (7 pgs) (Apr. 3, 2012).
Draelos et al. Glycation and Skin Aging: A Review. Cosmetics & Toiletries Magazine (3 pgs.) (Jun. 2011).
Driskell et al. Defining dermal adipose tissue. Exp Dermatol 23(9):629-631 (2014).
Duncan et al. A prospective study analyzing the application of radiofrequency energy and high-voltage, ultrashort pulse duration electrical fields on the quantitative reduction of adipose tissue. J Cosmet Laser Ther 18(5):257-67 (2016).
Emami-Razavi et al. Effect of Bentonite on Skin Wound Healing: Experimental Study in the Rat Model. Acta Medica Iranica 44(4):235-240 (2006).
ESSENSKIN™ The essential by instinct. Brochure (2 pgs.) (2008).
European Application No. 17748189.2 International Search Report and Written Opinion dated Jul. 25, 2019.
EWC's Skin Deep Cosmetics Database 'System JO Maximizer Shaping Cream' Nov. 2014 Retrieved from the internet:< URL: http:www.ewg.orgskindeepproduct526533System_JO_Maximizer_Shaping_Cream> (5 pgs).
EWG's Skin Deep Cosmetics Database: System JO Maximizer Shaping Cream; XP009512694; Washington (2014).
Fligiel et al. Collagen degradation in aged/photodamaged skin in vivo and after exposure to matrix metalloproteinase-1 in vitro. J Invest Dermatol 120:842-848 (2003).
Floquet et al. Structural Characterization of VGVAPG an Elastin-Derived Peptide. Biolpolymers 76:266-280 (2004).
Foster et al., Dermal white adipose tissue undergoes major morphological changes during the spontaneous and induced murine hair follicle cycling: a reappraisal. Archives of Dermatological Research 310(5):453-462. doi: 10.1007/s00403-018-1831-y (2018).
Garibyan et al. Three-dimensional volumetric quantification of fat loss following cryolipolysis. Lasers Surg Med 46(2):75-80 (2014).
Gautam, et al. Topical Delivery of Protein and Peptide Using Novel Cell Penetrating Peptide IMT-P8. Sci. Rep. 6, 26278 (2016).
Grant et al. Fat in flames: influence of cytokines and pattern recognition receptors on adipocyte lipolysis. Am J Physiol Endocrinol Metab 309(3):E205-13 (2015).
Gregory et al. The macrophage and the apoptotic cell: an innate immune interaction viewed simplistically? Immunology 113:1-14 (2004).
Gruber et al. Modulation of cellular senescence in fibroblasts and dermal papillae cells in vitro. J Cosmet Sci. 64(2):79-87 (2013) (Abstract).
Hakozaki et al. The effect of niacinamide on reducing cutaneous pigmentation and suppression of melanosome transfer. Br J Dermatol 147:20-31 (2002).
He et al. Receptor for advanced glycation end products binds to phosphatidylserine and assists in the clearance of apoptotic cells. EMBO Reports 12(4):358-364 (2011).
Hocker et al. Inhibition of autophagy through MAPK14-mediated phosphorylation of ATG5. Autophagy 9(3):426-428 (2013).
Ingargiola et al. Cryolipolysis for fat reduction and body contouring: safety and efficacy of current treatment paradigms. Plast Reconstr Surg 135(6):1581-90 (2015).
International Application No. PCT/US2019/044714 Invitation to Pay Additional Fees dated Oct. 1, 2019.
Ito et al. Is the Hair Follicle Necessary for Norm Wound Healing. J Invest Dermatol 128:1059-1061 (2008).
Jain et al.: Transfollicular drug delivery: current perspectives. Research and Reports in Transdermal Drug Delivery. (2016).
Jalian et al. Paradoxical adipose hyperplasia after cryolipolysis. JAMA Dermatol 150(3):317-9 (2014).
Johnson et al. Controlled delivery of heparin-binding EGF-like growth factor yields fast and comprehensive wound healing. J Control Release 166(2):124-129 (2013).
Johnson et al.: Safety Assessment of Tripeptide-1, Hexapeptide-12, their Metal Salts and Fatty Acyl Derivatives, and Palmitoyl Tetrapeptide-7 as Used in Cosmetics. Cosmetic Ingredient Review. 37(Supplement3):90S-102S (2014) https:http://www.cir-safety.org/sites/default/files/tripep062014final.pdf.
Jose et al. Enhanced trophic factor secretion by mesenchymal stem/stromal cells with Glycine-Histidine-Lysine (GHK)-modified alginate hydrogels. Acta Biomater 10(5):1955-1964 (2014).

(56) References Cited

OTHER PUBLICATIONS

Katsiki et al. The olive constituent oleuropein exhibits proteasome stimulatory properties in vitro and confers life span extension of human embryonic fibroblasts. Rejuvenation Res 10(2):157-172 (2007).
Khamlue et al. Skin Wound Healing Promoting Effect of Polysaccharides Extracts from Tremella fuciformis and Auricularia auricula on the ex-vivo Porcine Skin Wound Healing Model. 2012 4th International Conference on Chemical, Biological and Environmental Engineering IPCBEE 43:93-98(2012).
Kilmer et al. Safety and efficacy of cryolipolysis for non-invasive reduction of submental fat. Lasers Surg Med 48(1):3-13 (2016).
Kontogianni et al. Olive leaf extracts are a natural source of advanced glycation end product inhibitors. J Med Food 16(9):817-822 (2013).
Koo et al. Protection from photodamage by topical application of caffeine after ultraviolet irradiation. Br J Dermatol 156(5):957-964 (2007).
Kovac et al. *Plantago lanceolata* L. water extract induces transition of fibroblasts into myofibroblasts and increases tensile strength of healing skin wounds. J Pharm Pharmacol 67(1):117-125 (2015).
Kruglikov et al. Skin aging: are adipocytes the next target? Aging (Albany NY) 8(7):1457-1469 (2016).
Laatikainen et al. SOD3 decreases ischemic injury derived apoptosis through phosphorylation of Erk1/2, Akt, and FoxO3a. PLoS One 6(8):e24456 (2011).
Lee et al. Protective effect and mechanism of phosphatidylserine in UVB-induced human dermal fibroblasts. EU J Lipid Sci Technol 115(7):783-790 (2013).
Li et al. Antioxidant and anti-inflammatory activities of methanol extracts of Tremella fuciformis and its major phenolic acids. J Food Sci 79(4):C460-468 (2014).
Liao et al. Antioxidative activity, moisture retention, film formation, and viscosity stability of Auricularia fuscosuccinea, white strain water extract. Biosci Biotechnol Biochem 78(6):1029-1036 (2014).
Liu et al. Elastic fiber homeostasis requires lysyl oxidase-like 1 protein.Nat Genet. 36(2):178-182 (2004).
Luebberding et al. Age-related changes in skin barrier function—quantitative evaluation of 150 female subjects.Int J Cosmet Sci. 35(2):183-190 (2013).
Lupo et al. Cosmeceutical peptides. Dermatol Ther 20:343-349 (2007).
Mahmoudi et al. Comparing the effects of Bentonite & Calendula on the improvement of infantile diaper dermatitis: A randomized controlled trial. Indian J Med Res 42:742-746 (2015).
Maixner et al. Autophagy in Adipose Tissue. Obes Facts. 5(5):710-721 (2012).
Manstein et al. Selective cryolysis: A novel method of non-invasive fat removal. Lasers in Surgery and Medicine 40(9):595-604 (2008).
Marino et al. Human autophagins, a family of cysteine proteinases potentially implicated in cell degradation by autophagy. J Biol Chem 278(6):3671-8 (2003).
Nagase Chemtex PIPS; Phosphatidylserine & phosphatidylinositol (4 pgs) (May 2015).
Navarrete-Solis et al. A Double-Blind, Randomized Clinical Trial of Niacinamide 4% versus Hydroquinone 4% in the Treatment of Melasma. Dermatol Res Pract 2011:379173 (2011).
Noblesse et al. Lysyl oxidase-like and lysyl oxidase are present in the dermis and epidermis of a skin equivalent and in human skin and are associated to elastic fibers. J Invest Dermatol 122(3):621-630 (2004).
Ojima et al. Dynamics of protein secretion during adipocyte differentiation. FEBS Open Bio 6(8):816-26 (2016).
OMAR. Oleuropein in olive and its pharmacologic effects. Sci Pharm 78(2):133-154 (2010).
Park et al. High-Intensity Focused Ultrasound for the Treatment of Wrinkles and Skin Laxity in Seven Different Facial Areas. Ann Dermatol 27(6):688-693 (2015).
PCT/US2017/016292 International Search Report and Written Opinion dated May 12, 2017.

PCT/US2018/045045 International Preliminary Report on Patentability dated Feb. 4, 2020.
PCT/US2018/045045 International Search Report and Written Opinion dated Oct. 10, 2018.
PCT/US2019/044714 International Search Report and Written Opinion dated Dec. 3, 2019.
Pereira et al. The role of inflammation in adipocytolytic nonsurgical esthetic procedures for body contouring. Clinical, Cosmetic and Investigational Dermatology 10:57-66 (2017).
PHYTOSONIC™ Brochure. Sederma (2 pgs.) (Sep. 2008).
Pickart et al. The Human Tripeptide GHKCU in Prevention of Oxidative Stress and Degenerative Conditions of Aging: Implications for Cognitive Health. Oxid Med Cell Longev 2012:324832 (2012).
Pickart. The human tri-peptide GHK and tissue remodeling. J Biomater Sci Polym Ed 19:969-988 (2008).
Plikus et al. Regeneration of fat cells from myofibroblasts during wound healing. Science 355(6326):748-752 (2017).
Preissig et al. Current laser resurfacing technologies: A review that delves beneath the surface. Semin Plast Surg 26(3):109-116 (2012).
Pro-Lipo™ Neo. Smart Lipsome Preparation. LucasMeyer Cosmetics PowerPoint Presentation (25 pgs) (viewed Aug. 2018).
Remington. The Science and Practice of Pharmacy. Mack Publishing Company, 19th Edition, 1995.
Resh. Fatty acylation of proteins: new insights into membrane targeting of myristoylated and palmitoylated proteins. Biochimica et Biophysics Acta 1451:1-16 (1999).
Rigacci et al. Oleuropein aglycone induces autophagy via the AMPK/mTOR signalling pathway: a mechanistic insight. Oncotarget 6(3):35344-35357 (2015).
Rivera-Gonzalez et al. Skin Adipocyte Stem Cell Self-Renewal is Regulated by a PDGFA/AKT-Signaling Axis. Cell Stem Cell 19(6):738-751 (2016).
Rnjak et al. Severe Burn Injuries and the Role of Elastin in the Design of Dermal Substitutes. Tissue Eng Part B Rev 17(2):81-91 (2011).
Russell et al. Studies on the antiobesity effect of zinc-alpha2-glycoprotein in the ob/ob mouse. Int J Obes (Lond) 35(3):345-354 (2011).
Seaman et al. Paradoxical Adipose Hyperplasia and Cellular Effects After Cryolipolysis: A Case Report. Aesthet Surg J 36(1):NP6-13 (2016).
Senior et al. Val-Gly-Val-Ala-Pro-Gly, a repeating peptide in elastin, is chemotactic for fibroblasts and monocytes. J Cell Biol 99:870-874 (1984).
Shadfar et al. Anatomy and Physiology of the Aging Neck. Facial Plast Surg Clin North Am. 22(2):161-170 (2014).
Shirakata et al. Heparin-binding EGF-like growth factor accelerates keratinocyte migration and skin wound healing. J Cell Sci 118(Pt 11):2363-2370 (2005).
Simeon et al. Expression and activation of matrix metalloproteinases in wounds: modulation by the tripeptide-copper complex glycyl-L-histidyl-L-lysine-Cu2+. J Invest Dermatol 112:957-962 (1999).
Simons. Angiogenesis: where do we stand now? Circulation 111(12):1556-1566 (2005).
Sinambela et al., Human in vivo study: dermal application of Rutin Smartcrystals® & peptide-loaded liposomes to decrease skin roughness. 40th Annual Meeting of the Controlled Release Society (2013).
Singh et al. Lipophagy: Connecting Autophagy and Lipid Metabolism. Int J Cell Biol. 2012:282041 (2012).
Skaltsounisd et al. Redox Biol. Aug. 2015;5:20515. doi: 10.1016j.redox.2015.04.010 (13 pgs.) (Epub Apr. 29, 2015).
Sklirou et al. Hexapeptide-11 is a novel modulator of the proteostasis network in human diploid fibroblasts. Redox Biology 5:205-215 (2015).
SymDecanox HA. New Generation of Antioxidant. Symris Brochure (34 pgs) (2015).
Takeuchi et al. Inhibition of platelet-derived growth factor signalling induces autophagy in malignant glioma cells. Br J Cancer 90(5):1069-75 (2004).

(56) References Cited

OTHER PUBLICATIONS

Tsai et al. How irritant is water? An overview. Contact Dermatitis 41(6):311-314 (1999).
U.S. Appl. No. 16/293,467 Office Action dated Sep. 17, 2019.
U.S. Appl. No. 15/423,530 1st Action Interview dated Sep. 6, 2017.
U.S. Appl. No. 15/423,530 Office Action dated Dec. 18, 2017.
U.S. Appl. No. 15/423,530 Preinterview Action dated May 25, 2017.
U.S. Appl. No. 16/004,259 Office Action dated Sep. 26, 2018.
U.S. Appl. No. 16/053,674 Preinterview Office Action dated Jan. 25, 2019.
UNISOOTH PN47. Induchem Switzerland. (15 pgs) (Sep. 21, 2010).
Uplevity™. Lipotec. Technical Report (25 pgs) (Jun. 2013).
Van Zutphen et al. Lipid droplet autophagy in the yeast *Saccharomyces cerevisiae*. Mol Biol Cell 25(2):290-301 (2014).
Verma et al. Transfollicular drug delivery: current perspectives. Research and Reports in Transdermal Drug Delivery 5:1-17 (2016).
Verma. Particle size of liposomes influences dermal delivery of substances into skin. International Journal of Pharmaceutics 258(1-2):141-151 (2003).
Vilchez et al. Marine carotenoids: biological functions and commercial applications. Mar Drugs 9(3):319-333 (2011).
Vogt et al. 40 nm, but not 750 or 1,500 nm, nanoparticles enter epidermal CD1a+ cells after transcutaneous application on human skin. J Invest Dermatol 126(6):1316-22 (2006).
Vural et al. Autophagy in macrophages: impacting inflammation and bacterial infection. Scientifica (Cairo) 2014:825463 (2014).
Wang. Lipid droplets, lipophagy, and beyond. Biochim Biophys Acta 1861(8 Pt B):793-805 (2016).
Wen et al. Xylose phosphorylation functions as a molecular switch to regulate proteoglycan biosynthesis. PNAS USA 111(44):15723-15728 (2014).
Widgerow et al. A Double-Blind Randomized controlled Trial Evaluation the Efficacy and Tolerability of a Topical body Treatment in Combination With Cryolipolysis Procedures. J Drugs Dermatol 18(4):342-348 (2019).
Widgerow et al. Extracellular Matrix Modulation: Optimizing Skin Care and Rejuvenation Procedures. J Drugs Dermatol 15(4s):S63-S71 (2016).
Widgerow et al. Non-Surgical Fat Reduction and Topical Modulation of Adipose Tissue Physiology. J Drugs Dermatol 18(4):375-380 (2019).
Widgerow et al. Preoperative Skin Conditioning: Extracellular Matrix Clearance and Skin Bed Preparation, A New Paradigm. Aesthetic Surgery Journal39(S3):S103-S111 (2019).
Widgerow. Chronic wound fluid-thinking outside the box. Wound Repair Regen 19(3):287-291 (2011).
Widgerow. Topical Skin Restoration Technology—Advances in Age Management Strategies. Modern Aesthetics (8 pgs.) (May/Jun. 2016).
Wohlrab et al. Niacinamide—Mechanisms of Action and Its Topical Use in Dermatology. Skin Pharmacol Physiol 27:311-315 (2014).
Wu et al. Caspases: a molecular switch node in the crosstalk between autophagy and apoptosis. Int J Biol Sci 10(9):1072-83 (2014).
Zhang et al. Induction of autophagy is essential for monocyte-macrophage differentiation. Blood 119(12):2895-2905 (2012).
Zoumalan. Topical Agents for Scar management: Are They Effective? J Drugs Dermatol 17(4):421-425 (Apr. 2018).
Mohan et al.: Encapsulation of bioactive whey peptides in soy lecithin-derived nanoliposomes: Influence of peptide molecular weight. ScienceDirect. Food Chemistry 213:143-148 (2016).
PCT/US2019/044714 PCT Communication dated Sep. 28, 2020.
Brazilian Patent Application No. BR112018015897-6 Office Action dated Apr. 29, 2021.
Japanese Patent Application No. 2018-539307 Office Action dated Sep. 30, 2020.
NIOD Lip Bio Lipid Concentrate. British Beauty Blogger (2015).
U.S. Appl. No. 17/192,494 Office Action dated May 14, 2021.
European Application No. 17748189.2 Office Action dated Mar. 15, 2021.
European Patent Application No. 18842077.2 Extended Supplemental European Search Report dated Jun. 16, 2021.
Marigliano et al.: Use of peptides in anti-aging functional cosmetology. Household and Personal Care Today. Tekno Scienze. Milano, IT. 4(1):4-11 (2010).
Pickart et al.: GHK Peptide as a Natural Modulator of Multiple Cellular Pathways in Skin Regeneration. Hindawi Publishing Corp. BioMed Research International. Article ID 648108, 7 pages (2015).
U.S. Appl. No. 16/529,577 Office Action dated Sep. 3, 2020.
U.S. Appl. No. 16/570,732 Office Action dated Nov. 16, 2020.
U.S. Appl. No. 17/192,494 Office Action dated Sep. 3, 2021.

\* cited by examiner

Day 9 Post-treatment

Day 4 Post-treatment

Prior to Treatment

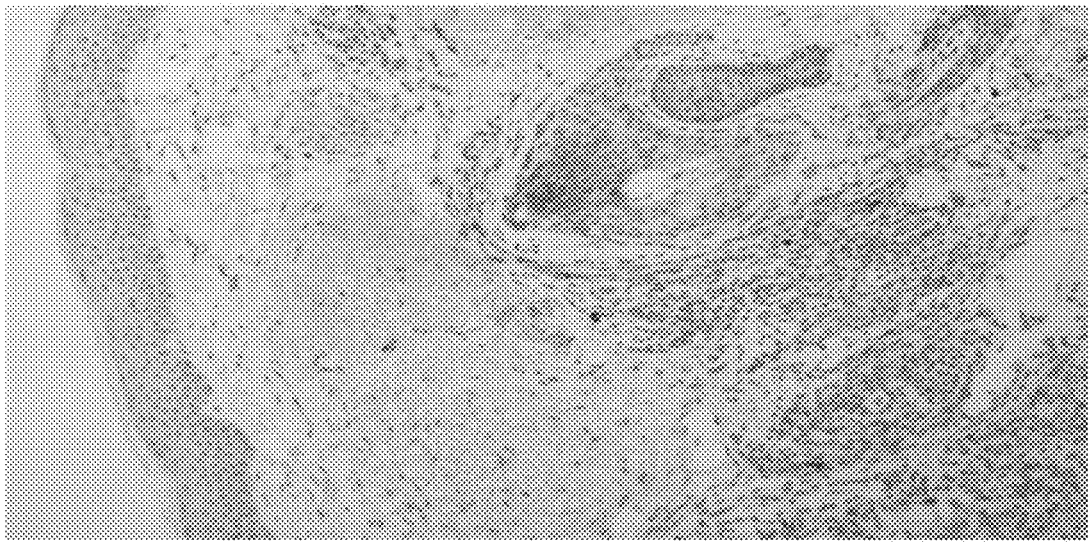

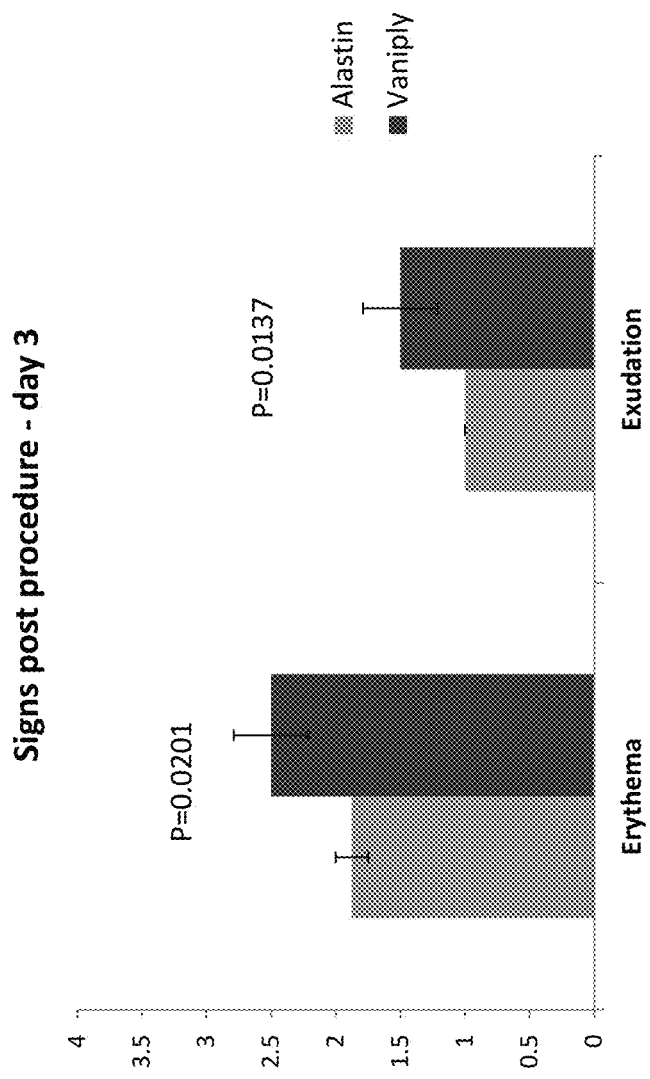

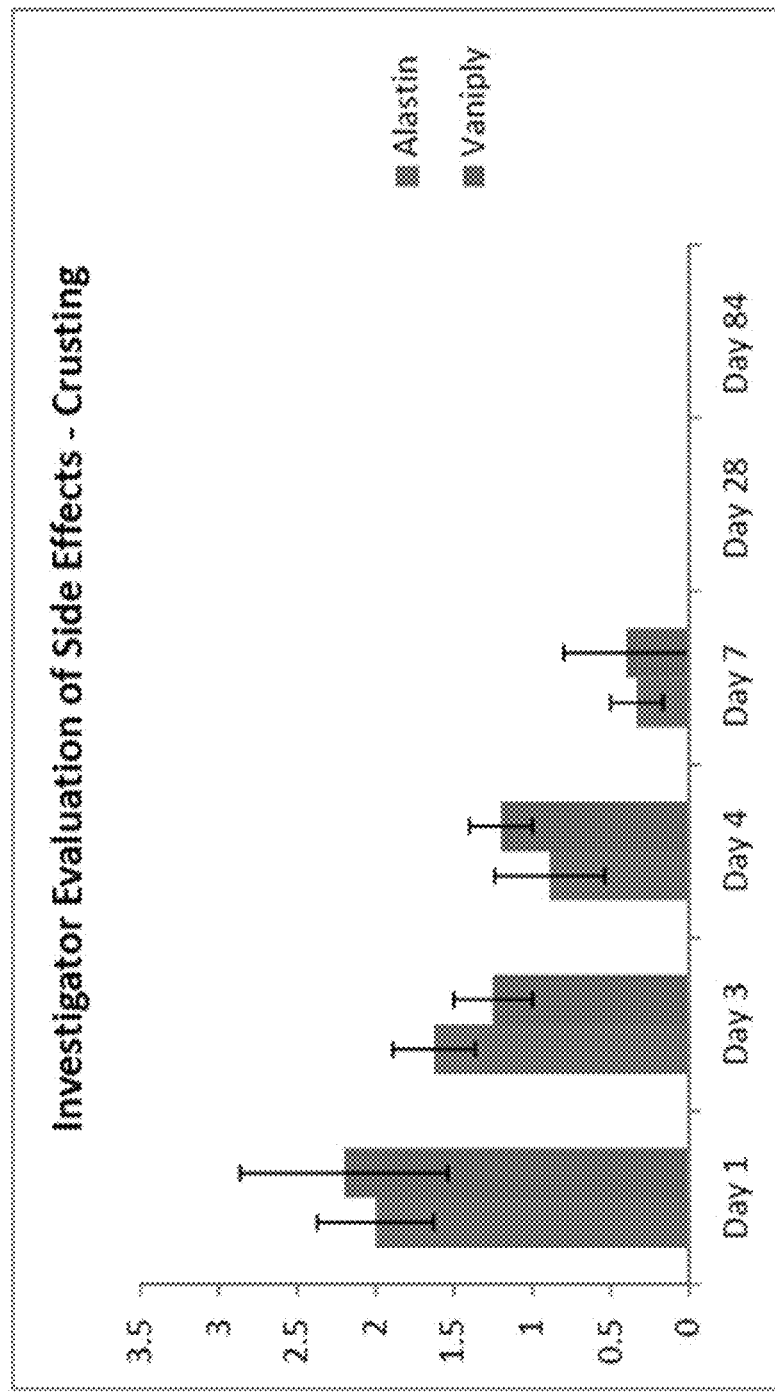

COMPOSITIONS AND METHODS FOR INVASIVE AND NON-INVASIVE PROCEDURAL SKINCARE

CROSS-REFERENCE TO RELATED APPLICATION

This application is a continuation Ser. No. 16/293,467, filed Mar. 5, 2019, which is a continuation of U.S. Ser. No. 16/004,259 filed Jun. 8, 2018, now issued as U.S. Pat. No. 10,286,030 on May 14, 2019, which is a continuation of U.S. Ser. No. 15/423,530 filed Feb. 2, 2017, issued as U.S. Pat. No. 10,086,035 on Oct. 2, 2018, which claims the benefit of U.S. Provisional Application No. 62/291,376, filed Feb. 4, 2016, and U.S. Provisional Application No. 62/303,332, filed Mar. 3, 2016. Each of the aforementioned applications is incorporated by reference herein in its entirety, and each is hereby expressly made a part of this specification. The aforementioned application is incorporated by reference herein in its entirety, and is hereby expressly made a part of this specification.

FIELD OF THE INVENTION

Compositions and methods for skincare treatment are provided, including compositions and methods for skin repair, promoting healthy skin, skin regeneration, and enhanced wound healing.

BACKGROUND OF THE INVENTION

The industry for invasive skin procedures such as cosmetic surgery, facial aesthetics, and medical lasers is estimated to expand to $3 billion by 2017. Due to this significant industry growth, the need for skincare treatments effective at promoting skin regeneration and alleviating the negative side effects of invasive skin treatments is also rapidly growing. These negative side effects are often a result of slow and ineffective skin regeneration or wound healing, which produces prolonged periods of inflammation, skin sensitivity, scarring, bruising, dry skin, infection, and other unfortunate skin conditions.

Traditional skincare treatments for alleviating these negative side effects have primarily relied upon a variety of common over the counter remedies. These common post-procedures and over-the-counter remedies have included skincare products such as facial and body lotions, skincare creams, petrolatum or petroleum jelly based products, butters, skin moisturizers, and a variety of other treatment products. However, these common remedies often may be primarily effective at treating one particular side effect, such as dry skin, and may not be meaningfully efficacious at treating other negative side effects. Moreover, many of the wide range of skincare products in the market are focused on treating the symptoms of slow wound healing, but do not enhance or promote skin regeneration itself.

SUMMARY OF THE INVENTION

Compositions and methods for promoting healthy skin, enhanced skin regeneration, wound healing, and treating other skin conditions are provided. These compositions preferably comprise two different peptides: a dipeptide, tripeptide, or tetrapeptide in combination with a pentapeptide, hexapeptide or heptapeptide. The peptide combination is effective in promoting healthy skin, skin regeneration, wound healing, and treating or ameliorating a variety of other skin conditions. Methods are also provided for producing and using the compositions.

Accordingly, in a first aspect, a topical composition for promoting skin repair is provided, comprising: one or more dipeptides, tripeptides, or tetrapeptides; and one or more pentapeptides, hexapeptides, or heptapeptides.

In a second aspect, a method for preparing a skin bed prior to a dermatologic treatment is provided, comprising: applying the topical composition of the first aspect to a skin bed, whereby the skin bed is prepared for a subsequent dermatological treatment, wherein the application of the topical composition to the skin bed prior to the dermatological treatment promotes healing of the damaged skin after the dermatological treatment.

In an embodiment of the second aspect, the topical composition of the first aspect is applied at least once a day to the skin bed.

In an embodiment of the second aspect, the topical composition of the first aspect is applied at least twice a day to the skin bed.

In an embodiment of the second aspect, the topical composition of the first aspect is first applied at least two weeks before the dermatological treatment.

In an embodiment of the second aspect, the topical composition of the first aspect is first applied at least four weeks before the dermatological treatment.

In a third aspect, a method for promoting skin repair after a dermatological treatment is provided, comprising: applying the topical composition of the first aspect to skin damaged by a dermatological treatment, whereby healing of the damaged skin is promoted.

In an embodiment of the third aspect, the topical formulation of the first aspect is applied at least once a day to the skin bed.

In an embodiment of the third aspect, the topical formulation of the first aspect is applied at least twice a day to the skin bed.

In an embodiment of the third aspect, the topical formulation of the first aspect is first applied for at least two weeks after the dermatological treatment.

In an embodiment of the third aspect, the topical formulation of the first aspect is first applied for at least four weeks after the dermatological treatment.

In an embodiment of the third aspect, the method further comprises: applying the topical composition of the first aspect to a skin bed prior to the dermatological treatment. For example, the topical composition of the first aspect is applied at least once a day to the skin bed, or at least twice a day to the skin bed, or is first applied at least two weeks before the dermatological treatment, or is first applied at least four weeks before the dermatological treatment.

In an embodiment of the method of the second aspect or third aspect, or any of their respective embodiments, the dermatological treatment is a laser treatment.

In an embodiment of the method of the second aspect or third aspect, or any of their respective embodiments, the dermatological treatment is a chemical peel.

In an embodiment of the method of the second aspect or third aspect, or any of their respective embodiments, the dermatological treatment is a treatment for actinic keratosis.

In an embodiment of the method of the second aspect or third aspect, or any of their respective embodiments, the dermatological treatment is a treatment for reducing signs of aging.

In a fourth aspect, a topical composition for promoting skin repair is provided, comprising palmitoyl tripeptide-1 and palmitoyl hexapeptide-12.

In an embodiment of the fourth aspect, the topical composition further comprises heptyl undecylenate.

In a fifth aspect, an anhydrous topical composition is provided comprising phosphatidyl serine, oleuropein and caprylyl methicone, wherein the topical composition is has a viscosity of from 10000 cPs to 25000 cPs, and wherein the anhydrous topical composition has an ability to maintain stability over three cycles of temperature testing from $-10°$ C. to $25°$ C.

In a sixth aspect, a topical composition for promoting skin repair is provided, comprising: 82-92 wt. % of a cyclopentasiloxane, dimethicone crosspolymer; 1-4 wt. % heptyl undecylenate; 0.01-0.06 wt. % of palmitoyl hexapeptide-12; 0.01-0.06 wt. % of palmitoyl tripeptide-1; 0.25-1 wt. % of caprylyl methicone; 0.05-0.1 wt. % of phospatidyl serine/lecithin; and 0.05-0.1 wt. % oleuropein.

In an embodiment of the sixth aspect, the topical composition comprises: 2-5 wt. % of a first carrier comprising the palmitoyl hexapeptide-12, the first carrier further comprising pentaerythrityl tetraisostearate, caprylic/capric triglyceride, propylene carbonate, and stearalkonium hectorite, wherein a concentration of the palmitoyl hexapeptide-12 in the carrier is 100 ppm; 2-5 wt. % of a second carrier comprising the palmitoyl tripeptide-1, the second carrier further comprising pentaerythrityl tetraisostearate, caprylic/capric triglyceride, propylene carbonate, and stearalkonium hectorite, wherein a concentration of the palmitoyl hexapeptide-12 in the carrier is 100 ppm.

In an embodiment of the sixth aspect, the topical composition further comprises: 1-4 wt. % PanthenylTriacetate/Naringenin; 1-4 wt. % Arnica Montana Extract; and 0.5-2 wt. % Dunaliella Salina Extract.

In a seventh aspect, a method for preparing a skin bed prior to a dermatologic treatment is provided, comprising: applying the topical composition of any of the fourth through sixth aspects to a skin bed, whereby the skin bed is prepared for a dermatological treatment which damages skin, such that healing of the damaged skin after the dermatological treatment is promoted.

In an embodiment of the seventh aspect, the topical composition is applied at least once a day to the skin bed for at least two weeks before the dermatological treatment.

In an embodiment of the seventh aspect, the topical composition is applied at least twice a day to the skin bed for at least four weeks before the dermatological treatment.

In an eighth aspect, a method for promoting skin repair after a dermatological treatment is provided, comprising: applying the topical composition of any of the fourth through seventh aspects to skin damaged by a dermatological treatment, whereby healing of the damaged skin is promoted.

In an embodiment of the eighth aspect, the topical composition is applied at least once a day to the skin bed for at least two weeks before the dermatological treatment.

In an embodiment of the eighth aspect, the topical composition is applied at least twice a day to the skin bed for at least four weeks before the dermatological treatment.

In a ninth aspect, a method for preparing a skin bed prior to a dermatologic treatment is provided, comprising: applying the topical composition of any of the fourth through seventh aspects to a skin bed, whereby the skin bed is prepared for a dermatological treatment which damages skin; and thereafter applying the topical composition to the skin damaged by the dermatological treatment, whereby healing of the damaged skin is promoted.

In an aspect of the ninth embodiment, the topical composition is applied at least once a day to the skin bed for at least two weeks before the dermatological treatment.

In an aspect of the ninth embodiment, the topical composition is applied at least twice a day to the skin bed for at least four weeks before the dermatological treatment.

In an embodiment of any of the seventh through ninth aspects, the dermatological treatment is a laser treatment.

In an embodiment of any of the seventh through ninth aspects, the dermatological treatment is a chemical peel.

In an embodiment of any of the seventh through ninth aspects, the dermatological treatment is a treatment for actinic keratosis.

In an embodiment of any of the seventh through ninth aspects, the dermatological treatment is a treatment for reducing signs of aging.

Any of the features of an embodiment of any of the aspects is applicable to all other aspects and embodiments identified herein. Moreover, any of the features of an embodiment of any of the aspects is independently combinable, partly or wholly with other embodiments described herein in any way, e.g., one, two, or three or more embodiments may be combinable in whole or in part. Further, any of the features of an embodiment of any of the aspects may be made optional to other aspects or embodiments.

DESCRIPTION OF THE DRAWINGS

The patent or application file contains at least one drawing executed in color. Copies of this patent or patent application publication with color drawing(s) will be provided by the Office upon request and payment of the necessary fee.

FIGS. 17A-17D provide photographs of skin biopsy samples for dual peptide treated skin three weeks after application at 40× (FIG. 17B), a baseline sample at 40× (FIG. 8A), a skin biopsy sample for dual peptide treated skin three weeks after application at 100× (FIG. 17D) and a baseline sample at 100× (FIG. 17C). Decreased MMP1 staining was observed over the three week period in the pre-auricular region.

FIGS. 19A-19I provide graphs of data generated during a randomized, single-blinded trial of the Alastin Procedure Enhancement System compared to standard of care following IPL and/or PDL with Q-switch-alexandrite and fractionated $CO_2$ laser resurfacing of the face.

DETAILED DESCRIPTION OF THE PREFERRED EMBODIMENT

Figure 1:
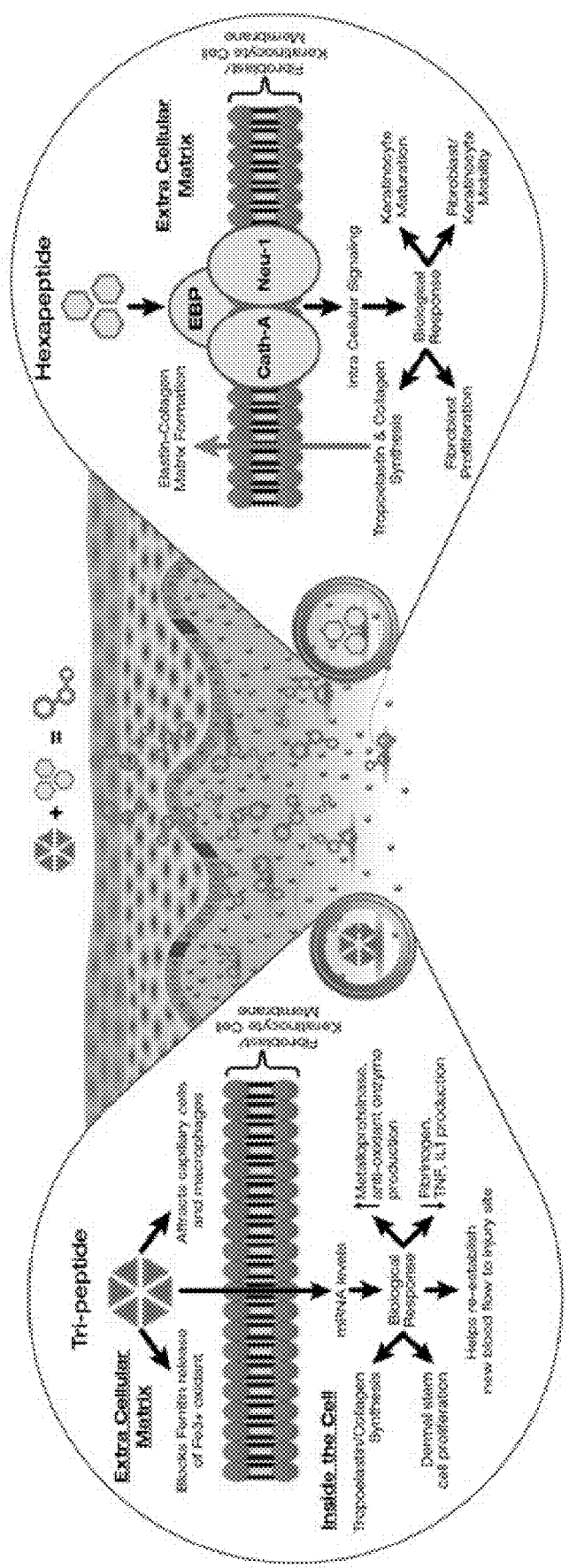
FIG. 1 is a schematic depiction of the mechanism by which an exemplary combination of peptides works to stimulate and restore elastin and collagen levels in the skin.

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

Definitions

The terms "pharmaceutically acceptable salts" and "a pharmaceutically acceptable salt thereof" as used herein are broad terms, and are to be given their ordinary and customary meaning to a person of ordinary skill in the art (and are not to be limited to a special or customized meaning), and refer without limitation to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts, e.g., salts of lysine, N,N'-dibenzylethylenediamine, chloroprocaine, choline, diethanolamine, ethylenediamine, meglumine (N-methylglucamine), procaine, and tris; salts of free acids and bases; inorganic salts, e.g., sulfate, hydrochloride, and hydrobromide; and other salts which are currently in widespread pharmaceutical use and are listed in sources well known to those of skill in the art, such as, for example, The Merck Index. Any suitable constituent can be selected to make a salt of the therapeutic agents discussed herein, provided that it is non-toxic and does not substantially interfere with the desired activity. In addition to salts, pharmaceutically acceptable precursors and derivatives of the compounds can be employed. Pharmaceutically acceptable amides, lower alkyl esters, and protected derivatives can also be suitable for use in compositions and methods of preferred embodiments. While it may be possible to administer the compounds of the preferred embodiments in the form of pharmaceutically acceptable salts, it is generally preferred to administer the compounds in neutral form.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included. For example all tautomers of phosphate groups are intended to be included. Furthermore, all tautomers of heterocyclic bases known in the art are intended to be included, including tautomers of natural and non-natural purine-bases and pyrimidine-bases.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallisation with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Therapeutic Uses

The compositions described herein are suitable for use in skin therapy, and more particularly, for skincare treatment, promoting skin regeneration, and promoting enhanced wound healing. The compositions are suitable for use in any surgical procedure involving a skin puncture, an incision, or other damage to the skin (e.g., chemical damage, cryogenic damage, mechanical damage, light damage, electrical damage, heat damage, damage resulting from deformation of the skin as in stretch marks, or the like) where enhanced wound healing (e.g., reduced time to healing, minimizing the appearance of the resulting scar, or the like) is desirable. The compositions are suitable for use in enhanced wound healing (e.g., acne scars, burn scars, other skin scars, chronic non-healing wounds). The compositions are suitable for use in conjunction with various dermatological or medical treatments or procedures that impact the dermis (e.g., phototherapy, removal of ecrine glands, radiation treatment for cancer) The compositions described herein may be suitable for skin therapy procedures that include but are not limited to aesthetic laser skin resurfacing treatments, laser hair removal, brow lift surgery, chemical peels (e.g., glycolic alpha hydroxyl acid peels, trichloroacetic acid peels, phenol peels, or the like), abdominoplasty, brachioplasty, blepharoplasty, mammoplasty, mastopexy, rhytidectomy or lower rhytidectomy, rhinoplasty, thigh lift surgery, melanocytic nevi (mole) removal, dermabrasion and microdermabrasion, retinoid treatments (e.g., isotretinoin, all-trans retinoic acid treatments, or the like), hyaluronic acid injections, botulinum toxin injections, filler treatments (e.g., wrinlde fill treatments or the like), sclerotherapy, gluteal augmentation surgery, micro-needling, tattooing, and any and all other treatments for hair removal, hair growth and regrowth (e.g., in conjunction with oral or topical minoxidil), infections (in combination with topical, oral, or injectable antibiotics), skin rejuvenation or resurfacing, acne removal or reduction, broken capillaries, rosacea, wrinlde reduction, pore reduction, ablation of cellulite and other dermal lipid depositions, wart and fungus removal, thinning or removal of scars including hypertrophic scars and keloids, treatment of abnormal pigmentation (e.g., port wine stains), tattoo removal, treatment of skin inconsistencies (e.g., texture, color, tone, elasticity, hydration, or the like), and general purpose lotions, e.g., hand lotions, face lotions, body lotions, etc.

A variety of surgical treatments and procedures can be conducted that involve damage to skin tissue. Ambulatory phlebectomy is an outpatient procedure developed by dermatologic surgeons that removes superficial veins (e.g., capillaries, spider veins, or varicose veins) through small, slit-like incisions in the skin. The treatment can result in temporary bruising and swelling and inflammation caused by small segments of vein that remain in the skin. Blepharoplasty is a surgical procedure that can restore a youthful appearance to the eye area. The upper and lower eyelids are lifted and loose or excess skin and fat tissue are removed from the eye area. Minor swelling and bruising can result. Cryolipolysis, also known as "fat freezing" or by the product name CoolSculpting, is a procedure that involves the non-invasive cooling of body fat to break down fat cells, resulting in a reduction of body fat without damage to other tissues. The effect takes several months to be seen. Redness and localized bruising can result. In cryosurgery, liquid nitrogen is used to remove skin growths, fade age spots and treat early stage basal and squamous cell carcinomas. The doctor will apply frozen nitrogen using either a cotton swab or a spray device. The goal is to freeze the skin quickly and then allow it to slowly thaw to cause maximum destruction to targeted skin cells. In some cases, additional applications may be needed. When treating skin cancer, the doctor may insert a small needle containing a thermometer into the treatment area to ensure the treated area has been sufficiently cooled. Potential complications include redness, swelling, bleeding, blisters, and healing problems. Dermabrasion is a procedure that uses a wire brush or a diamond wheel with rough edges to remove and level the upper layer of skin. The treated area heals, allowing new skin to grow in its place. It often is used for facial procedures. It can result in swelling and infection. Dermal fillers—Juvederm, Restylane, Belotero, and Voluma—contain some form of hyaluronic acid, a substance that naturally occurs throughout the body and skin, with the highest concentrations in the fluids of the eyes and joints. Radiesse is a calcium hydroxyapatite filler, while Sculptra contains L-poly-lactic acid. Fillers can be used to temporarily plump lips, raise depressed scars and level wrinkled skin. First, the doctor marks the areas to be injected. Topical or injection numbing medication may be used for added comfort. Then the fillers are injected by syringe using very fine needles. The effect typically lasts about six months. After that, additional injections are required to maintain the effect. Potential side effects include swelling, bruising, bleeding, blisters, cysts, and inflammatory reactions. Hair transplants include punch transplanting, wherein a plug containing hair follicles is removed from a part of the scalp where hair is more dense and transplanted to the treatment area. Hair transplantation has a high success rate as long as there is enough donor hair. The procedure can result in skin irritation or damage where hair is removed from or transplanted to. Laser/light therapy is a non-invasive procedure that uses light energy to repair and regenerate damaged skin. During the procedure, patients may feel a pinch similar to the snapping of a rubber band. Topical anesthetic or chilled gel may be applied to prevent discomfort. Treated area may be pink or red for four to eight hours after treatment. A slight stinging sensation, similar to a mild sunburn in the treated area can be observed, which usually subsides within four to six hours, and, mild swelling in the treatment area that usually dissipates within several days can occur. Potential complications include swelling and crusting. In liposuction, a surgeon uses a cannula to remove pockets of excess fat from various parts of the body. The cannula is inserted through small incisions made in the skin. In some procedures, the fat is loosened with water or liquefied by laser to facilitate its removal. The procedure is minimally-invasive and is usually performed under local tumescent anesthesia. After fat is removed, the incisions are usually left open to allow for drainage. The procedure can result in tissue damage, skin necrosis, bruising, and swelling. In microdermabrasion, a slightly rough applicator tip is applied to the surface of the skin of the face or neck to remove the uppermost layer of skin. This results in a smoother skin texture. The procedure is painless and non-invasive, but can result in skin irritation or infection. Micro-lipoinjection is the transfer or recycling of fat from one body area to another. Potential complications include bruising and swelling. Tattooing, which includes micropigmentation, also known as permanent cosmetics, is the process of inserting colored pigments just beneath the skin's surface. The procedure can result in inflammation or infection. Neck lifts are a surgical option to improve the appearance of the neck. Results are typically long-lasting. There are two primary types of neck lifts, including cervicoplasty wherein excess skin is surgically removed from the neck, and platsmaplasty, a procedure which reduces the banded appearance of the neck by removing, tightening or realigning the muscles of the neck. The procedures can result in bruising, infection, and swelling. Neuromodulators are wrinkle-relaxing injections of botulinum toxin—commercially known as Botox Cosmetic, Dysport or Xeomin—that are used to treat wrinkles, frown lines and crow's feet. A minute amount of the neuromodulator is injected directly into the underlying muscle, causing it to relax and gradually smooth out the appearance of the overlying skin. The effects typically last about three months. Potential complications include bruising and soreness. Non-ablative skin rejuvenation uses a laser to improve the appearance of wrinkles, brown spots and minor scars by creating heat in the skin without injuring the surface of the skin. The heat generated by the laser promotes collagen production which causes the skin to tighten and look young and healthy. Nonablative lasers often are fractionated so they deliver heat into the skin through thousands of tiny, deep columns known as microthermal treatment zones with intervening normal untreated skin. The fractional approach allows the skin to heal much faster than if the entire area was treated. This approach lessens the recovery period and reduces the number of complications that can occur. Multiple sessions are needed in most cases. The procedure can cause redness, swelling, and infection. Non-invasive body contouring treatments include low level laser therapy, which emits cold laser energy into body tissues that are absorbed by fat cells, which are broken down and absorbed into the body, and ultrasound, which uses high-intensity, focused sound waves to disrupt fat calls, causing them to dissolve gradually over time. Radiofrequency delivers controlled energy to excess fat areas, creating heat deep within fat cells and subsequently destroying them. Radiofrequency therapy is regularly used for body contouring in dermatology. Redness and bruising can result.

In each of the foregoing therapies, some degree of skin damage can result which may be alleviated by using the peptide compositions as described herein. The peptide compositions as disclosed herein can be applied as a pretreatment to therapy (e.g., daily for 1-31 days or more, e.g., daily for one, two, three, or four weeks, before commencing therapy) and/or as a post-treatment after therapy (e.g., daily for 1-31 days or more, e.g., daily for one, two, three, or four weeks, after completion of therapy).

Actinic Keratosis

The compositions as described herein are suitable for use connection with the treatment of actinic keratosis or certain other forms of cancerous skin lesions. Actinic keratoses, also called solar keratoses, are scaly, crusty growths or lesions caused by damage from the sun's ultraviolet rays. They typically appear on sun-exposed areas such as the face, bald scalp, lips, and the back of the hands, and are often elevated, rough in texture, and resemble warts. Most become red, but some will be tan, pink, and/or flesh-toned. If left untreated, up to ten percent of actinic keratoses develop into squamous cell carcinoma. In rarer instances, actinic keratoses may also turn into basal cell carcinomas. Almost all actinic keratoses can be eliminated if treated early, before they become skin cancers (benign or malignant growths or tumors). Various treatment options are available, which depend on the growth's characteristics and the patient's age and health.

Cryosurgery is the most commonly used treatment method when a limited number of actinic keratosis lesions exist. Treatment can be performed in the physician's office, and no cutting or anesthesia is required. Liquid nitrogen, applied with a spray device or cotton-tipped applicator, freezes the growths. The lesions subsequently shrink and/or blister, become crusted and fall off. Temporary redness and swelling may occur after treatment, and in some patients, pigment may be lost, leaving white spots.

When actinic keratoses are numerous and widespread, commercially available topical creams, gels and solutions for treating actinic keratoses can be employed in combination with the compositions as described herein. One of the most commonly used topical medications for actinic keratoses is 5-fluorouracil (5-FU) cream or solution. 5-FU in cream or lotion form is applied to the lesion areas once or twice daily for two to four weeks. It can be used on all affected areas. 5-FU is available in a variety of formulations, in concentrations ranging from 0.5 percent to 5 percent. Temporary side effects include redness, swelling, and crusting. Aldara or Zyclara (imiquimod) cream, also employed to treat actinic keratoses, works by stimulating the immune system to produce interferon, a chemical that destroys cancerous and precancerous cells. A topical formulation, e.g., at a concentration of 5%, 3.75% or 2.5%, is applied to the lesion two or three times a week for several weeks or months. The cream is generally well-tolerated, but some individuals develop redness and ulcerations. actinic keratoses. A gel combining hyaluronic acid with the non-steroidal anti-inflammatory drug diclofenac may also be effective for people whose skin is oversensitive to other topical treatments. The gel is applied twice a day for two to three months. Picato® (ingenol mebutate), available in concentrations of 0.015 and 0.05 percent, treats actinic keratoses with just two or three days application time, including three consecutive days for the 0.015% concentration (used on the face and scalp) and two consecutive days for the more concentrated 0.05% gel (used on the trunk and extremities). Skin redness, flaking/scaling, crusting, and swelling are the most common side effects. The adverse effects of these treatments (redness, crusting, swelling) may be alleviated by using the peptide compositions as described herein. The peptide compositions as disclosed herein can be applied as a pretreatment (e.g., daily for 1-31 days or more, e.g., daily for one, two, three, or four weeks, before commencing application of 5-FU, imiquimod cream, hyaluronic acid/diclofenac, or ingenol mebutate), and/or in the same topical formulation as 5-FU, imiquimod cream, hyaluronic acid/diclofenac, or ingenol mebutate, and/or as a post-treatment after application of 5-FU, imiquimod cream, hyaluronic acid/diclofenac, or ingenol mebutate (e.g., daily for 1-31 days or more, e.g., daily for one, two, three, or four weeks, after application of 5-FU, imiquimod cream, hyaluronic acid/diclofenac, or ingenol mebutate has ceased).

Photodynamic therapy is also employed for treatment of actinic keratoses as well as Bowen's Disease, a superficial form of squamous cell carcinoma that appears as a persistent red-brown scaly patch. Photodynamic therapy is especially useful for widespread lesions on the face and scalp. A light-sensitizing agent, topical 5-aminolevulinic acid or methyl aminolevulinate, is applied to the lesions. Subsequently, those medicated areas are activated by strong blue or red light, which selectively destroys actinic keratoses. Redness, pain and swelling can result. After the procedure, patients must strictly avoid sunlight for at least 48 hours, as UV exposure will increase activation of the medication, and may cause severe sunburns. The adverse effects of this treatment (redness, pain, swelling) may be alleviated by using the peptide compositions as described herein. The peptide compositions as disclosed herein can be applied as a pretreatment to photodynamic therapy (e.g., daily for 1-31 days or more, e.g., daily for one, two, three, or four weeks, before commencing photodynamic therapy) and/or as a post-treatment after photodynamic therapy (e.g., daily for 1-31 days or more, e.g., daily for one, two, three, or four weeks, after completion of photodynamic therapy).

Cryotherapy, 5-FU, imiquimod cream, hyaluronic acid/diclofenac, ingenol mebutate, and photodynamic therapy can be combined for treatment of actinic keratoses, along with use of the peptide compositions disclosed herein to encourage skin repair. Treatment regimens can include cryosurgery combined with photodynamic therapy or a topical agent like imiquimod, diclofenac, of 5-FU. The topical medications and photodynamic therapy may also be used serially every three months, six months, or year, as determined by the physician at routine skin examinations. This approach may both improve the cure rate and reduce side effects. One to two weeks of 5-FU followed by cryosurgery can reduce the healing time for 5-FU and decrease the likelihood of white spots following cryosurgery.

Curettage and electrodessication can be employed to remove portions of actinic keratoses, with electrocautery or trichloroacetic acid employed to stop bleeding, optionally under local anesthesia. The peptide formulations disclosed herein can advantageously be employed as a pretreatment or post-treatment. The peptide compositions as disclosed herein can be applied as a pretreatment to curettage and/or electrodessication (e.g., daily for 1-31 days or more, e.g., daily for one, two, three, or four weeks, before commencing curettage and/or electrodessication) and/or as a post-treatment after curettage and/or electrodessication (e.g., daily for 1-31 days or more, e.g., daily for one, two, three, or four weeks, after completion of curettage and/or electrodessication).

Chemical peeling, commonly employed to reverse the signs of photoaging, is also used to remove superficial actinic keratoses on the face, especially when other techniques have not succeeded. Trichloroacetic acid and/or similar chemicals are applied directly to the skin, causing the top skin layers to slough off. New skin generally regrows within a few weeks. This technique may require local anesthesia and can cause temporary discoloration and irritation. The peptide formulations disclosed herein can advantageously be employed as a pretreatment or post-treatment. The peptide compositions as disclosed herein can be applied as a pretreatment to chemical peeling (e.g., daily for 1-31 days or more, e.g., daily for one, two, three, or four weeks, before commencing chemical peeling) and/or as a post-treatment after chemical peeling (e.g., daily for 1-31 days or more, e.g., daily for one, two, three, or four weeks, after completion of chemical peeling).

Laser surgery can also be employed to treat actinic keratoses. The skin's outer layer and variable amounts of deeper skin are removed using a carbon dioxide or erbium YAG laser, as described elsewhere herein. Lasers are effective for removing actinic cheilitis from the lips and actinic keratoses from the face and scalp. They offer good control over the depth of tissue removed. Lasers are also used as a secondary therapy when topical medications or other techniques are unsuccessful. However, local anesthesia may be required. The risks of scarring and pigment loss are slightly greater than with other techniques. Accordingly, use of peptide formulations disclosed herein can advantageously be employed as a pretreatment or post-treatment. The peptide compositions as disclosed herein can be applied as a pretreatment to laser treatment (e.g., daily for 1-31 days or more, e.g., daily for one, two, three, or four weeks, before commencing laser treatment) and/or as a post-treatment after laser treatment (e.g., daily for 1-31 days or more, e.g., daily for one, two, three, or four weeks, after completion of laser treatment).

Chemical Peel

The peptide compositions described herein are useful in conjunction with chemical peel treatments. A chemical peel is a technique used to improve the appearance of the skin on the face, neck or hands. A chemical solution is applied to the skin that causes it to exfoliate and eventually peel off. The new skin is usually smoother and less wrinkled than the old skin. The new skin is also temporarily more sensitive to the sun. There are three basic types of chemical peels. A superficial peel can employ alpha-hydroxy acid or another mild acid to penetrate only the outer layer of skin to gently exfoliate it. The treatment is used to improve the appearance of mild skin discoloration and rough skin as well as to refresh the face, neck, chest or hands. In a medium peel, glycolic or trichloroacetic acid is applied to penetrate the out and middle layers of skin to remove damaged skin cells. The treatment is used to improve age spots, fine lines and wrinkles, freckles and moderate skin discoloration. It also can be used to smooth rough skin and treat some precancerous skin growths, e.g., actinic keratoses as described elsewhere herein. In a deep peel, tricholoracetic acid or phenol is applied to deeply penetrate the middle layer of skin to remove damaged skin cells. The treatment removes moderate lines, age spots, freckles and shallow scars. Patients will see a dramatic improvement in skin appearance; however, the treatment can result in varying degrees of damage to the layers of the skin. The peptide compositions as disclosed herein can be applied as a pretreatment to chemical peeling (e.g., daily for 1-31 days or more, e.g., daily for one, two, three, or four weeks, before commencing chemical peeling) and/or as a post-treatment after chemical peeling (e.g., daily for 1-31 days or more, e.g., daily for one, two, three, or four weeks, after completion of chemical peeling).

One type of chemical peel is a pulse peel, which involves application of a glycolic acid peel followed by application of an agent to target cancerous cells (e.g., 5-fluorouracil). The treatment can repeated four to six times over a two week period. Preconditioning with the formulations of the embodiments can advantageously be employed in conjunction with a pulse peel, or can advantageously be employed to facilitate healing when applied post-procedure.

Laser Resurfacing

In particular, the compositions described herein may be suitable for use prior to and/or following treatment with ablative and non-ablative laser resurfacing treatments that may be fractionated or unfractionated. In ablative laser treatments, the laser procedure removes the outer layers of skin at a specific targeted area. These procedures require a longer duration wound healing process than non-ablative laser treatments, which do not lead to the removal or vaporization of skin. Non-fractionated laser treatments act on the entire projected surface area of the treated skin, whereas fractionated laser treatments act on evenly divided portions of a targeted area to provide untouched regions of skin for quickened healing. As such, fractionated laser treatments have resulted in fewer side effects with lower amounts of reported scarring. See e.g. Preissig, J., Hamilton, K., Markus, R., Current laser resurfacing technologies: A review that delves beneath the surface, Seminars in Plastic Surgery 2012, Vol. 26(3), pp. 109-116. Ablative laser treatments may include but are not limited to $CO_2$, Er:YAG (erbium-doped yttrium aluminum garnet), combined Erbium/$CO_2$, and fractional laser photothermolysis laser resurfacing procedures. $CO_2$ lasers emit light at the 10,600 nm wavelength at pulses ranging as low as 0.2 µs-80 µs with higher intensity lasers and up to 10 ms pulses with lower intensity lasers. Er:YAG lasers emit light at the 2,940 nm wavelength and have pulses ranging from 0.25 up to 5 ms. Combination $CO_2$ and Er:YAG lasers rely on a combination of treatment with both types of lasers. Shorter pulses facilitate higher energy delivery and facilitate deeper ablation of skin. Non-ablative laser treatments may include diode, Erbium glass, thulium fiber, and Nd:YAG (neodymium-doped yttrium aluminum garnet) lasers. These treatments use lasers that emit light at wavelengths ranging from 1319 to 1927 nm at pulses ranging from 450 µs up to 210 ms. The peptide compositions as disclosed herein can be applied as a pretreatment to laser treatment (e.g., daily for 1-31 days or more, e.g., daily for one, two, three, or four weeks, before commencing laser treatment) and/or as a post-treatment after laser treatment (e.g., daily for 1-31 days or more, e.g., daily for one, two, three, or four weeks, after completion of laser treatment).

Skin Repair

The active ingredients of the compositions include two or more peptides. The first peptide in the combination is one or more dipeptides, tripeptides, and/or tetrapeptides and the second peptide in the combination is one or more pentapeptides, hexapeptides, and/or heptapeptides. The compositions may be used in cosmetic, cosmeceutical and general skincare compositions or provided in pharmaceutical compositions. Methods are also described for using compositions comprising the dipeptide, tripeptide, or tetrapeptide and the pentapeptide, hexapeptide, or heptapeptide for the promotion of healthy skin, skin regeneration and enhanced wound healing.

In general, skin regeneration and wound healing involve complicated and poorly understood processes that rely on the combined efforts of a large number of different tissues and cell types. Successful wound healing, which can be considered a type of tissue remodeling, occurs when the tissue remodeling process alleviates the inflammatory response of the innate immune system and minimizes the scar forming process that occurs when fibrous tissue replaces normal skin after an injury. This process occurs most efficiently in young children but becomes less efficient with age. Less efficient wound healing often produces unsightly, irritating, and even painful scars such as keloids or hypertrophic scars. Given that few of the patients undergoing invasive skin procedures are children, skincare treatments that can promote wound healing after an invasive skin procedure are particularly desirable. The combination of the two peptides has superior efficacy in promoting wound healing and skin regeneration.

Additionally, the compositions help treat or prevent dermatologic conditions such as skin dryness, dullness, loss of elasticity, lack of radiance, exaggerated lines and wrinkles, stretch marks, spider vessels or red blotchiness. In some embodiments, the appearance of "marionette" lines, smile lines, deep nasolabial fold lines, crow's feet, fine lines/wrinkles, vertical lines between the eyebrows, horizontal forehead lines, sagging thin/frail skin, skin redness and dullness may be improved using compositions as described herein. The compositions can also be used in the prevention and treatment of photodamaged skin, the appearance of fine lines and wrinkles, hyperpigmentation, age spots, and aged skin. The disclosed compositions can also help increase the flexibility of the stratum corneum, increasing the content of collagen and/or glycosaminoglycans in skin, increasing moisture in skin, decreasing transcutaneous water loss, and generally increasing the quality of skin.

The compositions can also be employed in the connection with mucous membranes, in particular the lips and the vaginal mucosa. When applied to the vaginal mucosa, a vaginal applicator can be employed as are commercially available. Suitable applicators can be in a form of a pre-filled syringe, a tube attached to a prefilled squeezable reservoir, a prepackaged wand including a preselected amount of composition, or a universal vaginal applicator including perforations along its length for dispensing the composition through the perforations.

Drug Delivery Uses

Certain of the compositions can be employed as a carrier for drug delivery. The anhydrous compositions as disclosed herein are particularly useful in this regard for the delivery of suitable for the delivery of locally acting drugs such as antibacterial drugs, antiprotozoal drugs, antifungal drugs, antiviral drugs, spermicidal agents, prostaglandins, and steroids. Drugs suitable for delivery include bromocriptine, sildenafil, oxytocin, calcitonin, luteinizing hormone-releasing hormone and analogues, insulin, human growth hormone, oxybutynin, and steroids used in hormone replacement therapy or for contraception. Antifungal drugs include clotrimazole, econazole, miconazole, terbinafine, fluconazole, ketoconazole, and amphotericin. Antibiotics include amoxicillin, doxycycline, cephalexin, ciprofloxacin, clindamycin, metronidazole, azithromycin, sulfamethoxazole/trimethoprim, amoxicillin/clavulanate, and levofloxacin. Classes of antibiotics include penicillins, tetracyclines, cephalosporins, quinolones, lincomycins, macrolides, sulfonamides, glycopeptides, aminoglycosides, and carbapenems. Types of hormones include 5-alpha-reductase inhibitors, adrenal cortical steroids, corticotropin, glucocorticoids, mineralocorticoids, adrenal corticosteroid inhibitors, antiandrogens, antidiuretic hormones, antigonadotropic agents, antithyroid agents, aromatase inhibitors, calcitonin, estrogen receptor antagonists, gonadotropin-releasing hormone antagonists, growth hormone receptor blockers, growth hormones, insulin-like growth factor, parathyroid hormone and analogs, progesterone receptor modulators, prolactin inhibitors, selective estrogen receptor modulators, sex hormones, androgens and anabolic steroids, contraceptives, estrogens, gonadotropin releasing hormones, gonadotropins, progestins, sex hormone combinations, somatostatin and somatostatin analogs, synthetic ovulation stimulants, and thyroid drugs. Antiviral agents include adamantane antivirals, antiviral boosters, antiviral combinations, antiviral interferons, chemokine receptor antagonist, integrase strand transfer inhibitor, miscellaneous antivirals, neuraminidase inhibitors, NNRTIs, NS5A inhibitors, nucleoside reverse transcriptase inhibitors (NRTIs), protease inhibitors, and purine nucleosides.

Drugs for treating skin conditions that can be employed using selected compositions as a delivery device include acne drugs (isotretinoin), atopic dermatitis drugs (topical steroids), herpes zoster drugs (antivirals such as valacyclovir), hives (antihistamines like loratadine or fexofenadine, omalizumab), sunburn (lidocaine), contact dermatitis (antihistamines, topical steroids), diaper rash (zinc oxide), rosacea (metronidazole, doxycycline, azelaic acid, isotretinoin, beta blockers, estrogen), athlete's foot (antifungals), and basal cell carcinoma (imiquimod, fluorouracil, vismodegib).

Types of Formulations

The peptide combinations of the embodiments can be employed in various types of formulations. Topical formulations including a dipeptide, tripeptide, or tetrapeptide, and a pentapeptide, hexapeptide, or heptapeptide in combination with at least one excipient, are provided. Excipients can include a nonaqueous or aqueous carrier, and one or more agents selected from moisturizing agents, pH adjusting agents, deodorants, fragrances, chelating agents, preservatives, emulsifiers, thickeners, solubilizing agents, penetration enhancers, anti-irritants, colorants, surfactants, beneficial agents, pharmaceutical agents, and other components as known in the art for use in connection with topical formulations for treatment of the skin. Preferably, the formulation is an anhydrous formulation to prevent skin irritation such as water-based irritant contact dermatitis or stinging sensation upon application to damaged skin. In another embodiment, the composition is formulated such that preservatives need not be employed (e.g., a preservative-free formulation) so as to avoid skin irritation associated with certain preservatives.

To facilitate application, the composition may be provided as an ointment, an oil, a lotion, a paste, a powder, a gel, or a cream. The composition may also include additional ingredients such as a protective agent, an emollient, an astringent, a humectant, a sun screening agent, a sun tanning agent, a UV absorbing agent, an antibiotic agent, an antifungal agent, an antiviral agent, an antiprotozoal agent, an anti-acne agent, an anesthetic agent, a steroidal anti-inflammatory agent, a non-steroidal anti-inflammatory agent, an antipruritic agent, an additional antioxidant agent, a chemotherapeutic agent, an anti-histamine agent, a vitamin or vitamin complex, a hormone, an anti-dandruff agent, an anti-wrinkle agent, an anti-skin atrophy agent, a skin whitening agent, a cleansing agent, additional peptides, additional modified peptides, and combinations thereof. In a further embodiment, the composition may avoid animal or cellular-based materials to avoid skin irritation. The composition can be applied to the dermis, or to mucous membranes.

Methods of using topical peptide formulations for promoting healthy skin, skin regeneration, and enhanced wound healing are provided. The compositions may also be applied to treat skin conditions such as inflammation, redness, soreness, skin sensitivity, dry skin, bruising, and similar conditions. Application of the peptide composition comprising a first dipeptide, tripeptide, or tetrapeptide and a second pentapeptide, hexapeptide, or heptapeptide may also be used to prevent scarring (e.g., in facelift procedures or other cosmetic procedures involving a skin incision), to quicken epithelial confluence, and to limit scabbing and crusting during wound healing. Increased collagen production and/or increased elastin production can also be induced through the application of a composition that comprises a first dipeptide, tripeptide, or tetrapeptide and a second pentapeptide, hexapeptide, or heptapeptide. Suitable methods for objectively measuring improvement in skin redness and inflammation may include tristimulus colorimetry, narrow-band reflectance spectroscopy, diffuse reflectance spectroscopy, skin reflectance spectroscopy, and/or UV photography.

Some embodiments include administering peptide compositions provided herein in topical formulations; however, other routes of administration are also contemplated (e.g., mucosal, subdermal, oral, or the like). Contemplated routes of administration include but are not limited to topical, mucosal, and subcutaneous. Suitable liquid forms include suspensions, emulsions, solutions, and the like. Unit dosage forms can also be provided, e.g., individual packets with a premeasured amount of the formulation, configured for administration to the face or other body part on a predetermined schedule pre-procedure and post-procedure. Unit dosage forms configured for administration twice or three times a day pre-procedure and post-procedure are particularly preferred; however, in certain embodiments it can be desirable to configure the unit dosage form for administration once a day, four times a day, or more.

In some embodiments, the topical and other formulations typically comprise from about 0.001 wt. % or less to about 50 wt. % or more of active ingredient, such as the peptides, preferably from about 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1 wt. % to about 2, 3, 4, 5, 6, 7, 8, 9, 10, 15, 20, 25, 30, 35, 40, or 45 wt. %.

Compositions and formulations for topical administration can include transdermal patches, ointments, lotions, creams, gels, drops, sprays, liquids, aerosols, and powders. Conventional pharmaceutical carriers, aqueous, powder or oily bases, thickeners and the like may be employed. In certain applications, an ointment, lotion, cream, gel or similar formulation can be provided that can be applied to the skin using the fingers. Such formulations are typically provided in a squeeze tube or bottle or a pot, or in a roll-on, wherein a ball is secured in the top of a container of the formulation, wherein the ball is permitted to roll. By rolling the ball over the skin surface, liquid in the container is transferred to the skin in a controlled manner. An alternative delivery mechanism includes a container with a perforated lid with a mechanism for advancing an extrudable formulation through the lid. In another form, a gel formulation with sufficient structural integrity to maintain its shape is provided, which is advanced up a tube and applied to the skin (e.g., in a stick form). An advantage of the stick form is that only the formulation contacts the skin in the application process, not the fingers or a portion of a container. A liquid or gel can also be placed using an applicator, e.g., a wand, a sponge, a syringe, or other suitable method.

Components of the Formulations

Peptides

Formulations comprising a combination of two or more peptides are provided for promoting healthy skin, skin regeneration, and enhanced wound healing, e.g., in patients subject to a skin procedure such as a laser treatment, a chemical peel, dermabrasion, microneedling, and other such procedures, in patients subject to any other treatment or exposure resulting in damage, inflammation, or irritation to the skin (e.g., sunburn, eczema, psoriasis, herpes lesions, shingles, allergic reaction, contact dermatitis, or the like), or in any skin condition wherein stimulation of collagen and/or elastin is beneficial. In a topical formulation comprising the two peptide combination, a first peptide (e.g., tripeptide) is present in the composition in pure for or in a form of a carrier containing the peptide, e.g., 50 ppm (by weight) or less to 1000, 5000, 10000, 50000, 100000, 500000 ppm or more, e.g., 100 ppm of the peptide. The topical formulation can contain from 0.01 wt. % or less (e.g., 0.001 wt. %) to 10 wt. % or more, e.g., 0.01 wt. % to 0.02 wt. %, 0.03 wt. %, 0.04 wt. %, 0.05 wt. %, 0.1 wt. %, 1 wt. % to 5 wt. % or 10 wt. % or 20 wt. % of the first peptide. The second peptide (e.g., hexapeptide) is present in the topical formulation composition in pure form or in a form of a carrier containing the peptide, e.g., 50 ppm (by weight) or less to 1000, 5000, 10000, 50000, 100000, 500000 ppm or more, e.g., 100 ppm of the peptide, or any other suitable amount. The topical formulation can contain from 0.01 wt. % or less (e.g., 0.001 wt. %) to 10 wt. % or more, e.g., 0.01 wt. % to 0.02 wt. %, 0.03 wt. %, 0.04 wt. %, 0.05 wt. %, 0.1 wt. %, 1 wt. % to 5 wt. % or 20 wt. % of the second peptide. The amount of peptide in the base can be adjusted up or down.

In example embodiments, a weight ratio for the first peptide to the second peptide in a topical formulation is 1 part first peptide to 0.2 to 10 parts second peptide, or 1 to 10 parts second peptide, or 1 to 8 parts second peptide, or 1 to 5.5 parts second peptide. The following nomenclature is employed herein to refer to various amino acids: Alanine (also referred to herein as "Ala" or "A"), Arginine (also referred to herein as "Arg" or "R"), Asparagine (also referred to herein as "Asn" or "N"), Aspartic acid (also referred to herein as "Asp" or "D"), Cysteine (also referred to herein as "Cys" or "C"), Glutamic acid (also referred to herein as "Glu" or "E"), Glutamine (also referred to herein as "Gln" or "Q"), Glycine (also referred to herein as "Gly" or "G"), Histidine (also referred to herein as "His" or "H"), Isoleucine (also referred to herein as "Ile" or "I"), Leucine (also referred to herein as "Leu" or "L"), Lysine (also referred to herein as "Lys" or "K"), Methionine (also referred to herein as "Met" or "M"), Phenylalanine (also referred to herein as "Phe" or "F"), Proline (also referred to herein as "Pro" or "P"), Serine (also referred to herein as "Ser" or "S"), Threonine (also referred to herein as "Thr" or "T"), Tryptophan (also referred to herein as "Trp" or "W"), Tyrosine (also referred to herein as "Tyr" or "Y"), Valine (also referred to herein as "Val" or "V").

In some embodiments, the first peptide is a dipeptide. Suitable dipeptides include but are not limited to those having the following sequence of amino acids: KK, KP, CK, KC, KT, DF, NF, VW, YR, or TT. In other embodiments, the first peptide is a tripeptide. Suitable tripeptides include but are not limited to those having the following sequence of amino acids: HGG, RKR, GHK, GKH, GGH, GHG, KFK, or KPK. In some embodiments, the first peptide is a tetrapeptide. Suitable tetrapeptides include but are not limited to those having the following sequence of amino acids: GQPR, KTFK, AQTR, or RSRK. In some embodiments, the second peptide is a pentapeptide. Suitable pentapeptides include but are not limited to those having the following sequence of amino acids: KTTKS, YGGFX or KLAAK. In some embodiments, the second peptide is a hexapeptide. Suitable hexapeptides include but are not limited to those having the following sequence of amino acids: VGVAPG or GKTTKS. In some embodiments, the second peptide is a heptapeptide. Suitable heptapeptides include but are not limited to one having an amino acid sequence RGYYLLE, or Heptapeptide-6 (a pro-sirtuin peptide). The compositions may include two or more peptides, e.g., two dipeptides and one pentapeptide; one tripeptide and one hexapeptide; one dipeptide, one tripeptide, and one heptapeptide, or the like, provided that the composition contains at least one dipeptide, tripeptide, or tetrapeptide and at least one pentapeptide, hexapeptide, or heptapeptide.

The peptide can be functionalized. For example, the peptide can be functionalized with a fatty acid, e.g., myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, caprylic acid, capric acid, lauric acid, palmitic acid, stearic acid, arachidic acid, behenic acid, lignoceric acid, cerotic acid, or the like. Examples include palmitoyl hexapeptide-12 (Pal-VGVAPG), palmitoyl tripeptide-1 (Pal-GHK), myristoyl hexapeptide-12 (Myr-VGVAPG), myristoyl tripeptide-1 (Myr-GHK). Palmitoyl or myristoyl functionalization can be desirable in certain embodiments as it exhibits enhanced penetration when compared to other fatty acids.

Some embodiments of the methods and compositions provided herein include as a first peptide glycine-histidine-lysine (GHK). GHK is a peptide sequence that is rarely found in the class of proteins in general, but is frequently found in extracellular matrix proteins. The small size of GHK permits it to approach membrane receptors far more easily than larger peptides. Further, its unique, copper-binding structure enhances copper transport into and out of cells and promotes wound healing through several different but related pathways. Due to its strong copper binding structure, GHK can be provided in the form of GHK-Cu (copper-bound GHK form).

GHK-Cu acts as an anti-inflammatory (see, e.g., Pickart, L., The human tri-peptide GHK and tissue remodeling, J. Biomater. Sci. Polymer Edn. 2008, Vol. 19, pp. 969-988, 972-973; Pickart et al., The Human Tripeptide GHK-CU in Prevention of Oxidative Stress and Degenerative Conditions of Aging: Implications for Cognitive Health, Oxid. Med. Cell Longev. 2012, Vol. 2012, pp. 1-8, 3) and an antioxidant. GHK-Cu acts to promote wound healing by suppressing the "acute phase response" that can produce both inflammation and induce scarring. This biological response prevents the invasion of bacteria, facilitates the arrival of immune cells, stems bleeding, and provides a covering for the wounded area. GHK-Cu also suppresses the acute phase response by inhibiting the production of molecules called cytokines. Cytokines are immune cell signaling molecules that attract immune cells and that trigger the production of other molecules that promote inflammation and fibrosis (leading to the creation of scar tissue). In particular, GHK-Cu suppresses the production of cytokines including tumor necrosis factor-alpha (TNFα), interleukin-1 (IL-1), interleukin-6 (IL-6), and transforming growth factor-beta-1 (TGF-β1), a few of the key drivers of inflammation and apoptotic cell death in the wound region. As TGF-β1 is an important component for the continuation of the acute phase response, GHK-Cu's suppression of TGF-β1 also acts to shorten the duration of the acute phase response once it has begun. GHK-Cu acts as an antioxidant by blocking ferritin's release of oxidizing iron, preventing further inflammation or microbial infection (as invading microbes need iron to survive).

GHK-Cu also stimulates blood vessel growth, increases collagen production, and regenerates the extracellular matrix. GHK-Cu acts as an attractant for cells vital to the regeneration of damaged tissues such as capillary cells that rebuild blood vessels. It also upregulates the production of a variety of enzymes that remove damaged proteins while also rebuilding the extracellular matrix (ECM), a key external scaffold that is important for intercellular communication and support. In particular, GHK-Cu's induces the production of messenger RNAs (mRNAs) necessary for the regeneration of the ECM, namely collagen, proteoglycans, glycosaminoglycans, chondroitin sulfate, and dermatan sulfate. GHK-Cu's induction of increased collagen production also plays a key role in enhancing skin regrowth. GHK-Cu further stimulates blood flow into damaged tissues through three processes: angiogenesis, anti-coagulation and vascular dilation. First, GHK-Cu induces angiogenesis or new blood vessel formation by increasing the production of growth factor proteins necessary for angiogenesis such as basic fibroblast growth factor (BFGF) and vascular endothelial growth factor (VEGF). Second, GHK-Cu increases blood flow to the wounded area by expanding the number of red blood cells (via growth in erythropoietin production) and by anti-coagulatory effects such as downregulating the blood clotting molecule thromboxane. Third, GHK-Cu facilitates vascular dilation through binding to the vasoconstriction protein angiotensin II, preventing angiotensin from constricting blood vessels and reducing blood flow.

GHK-Cu promotes stem cell proliferation (see, e.g., Ito et al., Is the Hair Follicle Necessary for Normal Wound Healing, J. Invest. Dermatol. 2008, Vol. 128, pp. 1059-1061, 1059). Wound healing studies have demonstrated that the addition of GHK-Cu greatly enlarged the production of hair follicles near the wound periphery in experiments with mice. Dermal hair follicles are a significant source of stem cells that are essential for dermal healing. Research into dermal hair follicles have demonstrated that hair-bearing areas tend to heal more quickly and that cells from various portions of the follicle may contribute to both dermal cell and epithelial cell replacement as well.

Thus, by decreasing inflammation, acting as an antioxidant, stimulating growth of new blood vessels, regenerating the extracellular matrix, enhancing collagen production, and by promoting stem cell proliferation, GHK can greatly enhance skin regeneration and promote wound healing.

Some embodiments of the methods and compositions provided herein include as a second peptide valine-glycine-valine-alanine-proline-glycine (VGVAPG). VGVAPG is a hexapeptide that is derived from the elastin protein (see, e.g., Blanchevoye et al., Interaction between the Elastin Peptide VGVAPG and Human Elastin Binding Protein, J. Biol. Chem. 2012, Vol. 288, pp. 1317-1328, 1317-1318). Elastin is a protein found in connective tissue (e.g. skin) that is necessary for tissues to return to their original shape and size after undergoing temporary expansion or contraction. Due to the importance of elastin in providing elasticity and resilience, elastin plays a significant role in skin cell resistance to injury and recovery from injury. The ability of skin to return to its original form after undergoing stretching or pulling relies on cross-linked elastin proteins (tropoelastin proteins in humans) that work to form "elastic fibers." The disruption of the elastic fiber system in healing wounds has been strongly linked to the production of scar tissue (see, e.g., Rnjak-Kovacina et al., Severe Burn Injuries and the Role of Elastin in the Design of Dermal Substitutes, Tissue Eng. Part B. Rev. 2011, pp. 81-91, 85-86). Because of these properties and others, elastin is a key component in the effective wound healing process.

VGVAPG plays a role in facilitating elastin's ability to prevent skin injury and to promote skin regeneration (see, e.g., Floquet et al., Structural Characterization of VGVAPG, an Elastin-Derived Peptide, Biopolymers (Peptide Science) 2004, Vol. 76, 266-280, 267). First, it has been shown to demonstrate the ability to attract monocytes and fibroblasts (see, e.g., Senior et al., Val-Gly-Val-Ala-Pro-Gly, a Repeating Peptide in Elastin, Is Chemotactic for Fibroblasts and Monocytes, J. Cell Biol. 1984, Vol. 99, pp. 870-874, 870), monocytes being essential for fighting off infection and fibroblasts being necessary for collagen production (the most abundant protein in skin) and for the regeneration of the extracellular matrix. Second, VGVAPG provides a binding site for elastin-binding protein, a permanent component of mature elastic fibers. Third, VGVAPG provides a binding site for elastin and extracellular matrix degradation enzymes such as matrix metalloproteinases (MMPs), which facilitate the replacement and regeneration of elastic fibers and extracellular matrix proteins.

The mechanism by which the peptide combination of the embodiments works to stimulate and restore elastin and collagen levels in the skin is depicted in FIG. 1. The exemplary composition contains a tripeptide and a hexapeptide. The schematic demonstrates the beneficial effects of the tripeptide and hexapeptide, which work synergistically to promote skin regeneration and wound healing through the attraction of healing cells, increased production of elastin and collagen, enhanced fibroblast proliferation, antioxidant behavior (preventing the release of oxidizing iron), and inducing the regeneration of the extracellular matrix. As a result, the combination of the two peptides exhibits synergistic, superior performance well beyond that expected for either of the two peptides alone.

Figure 2:
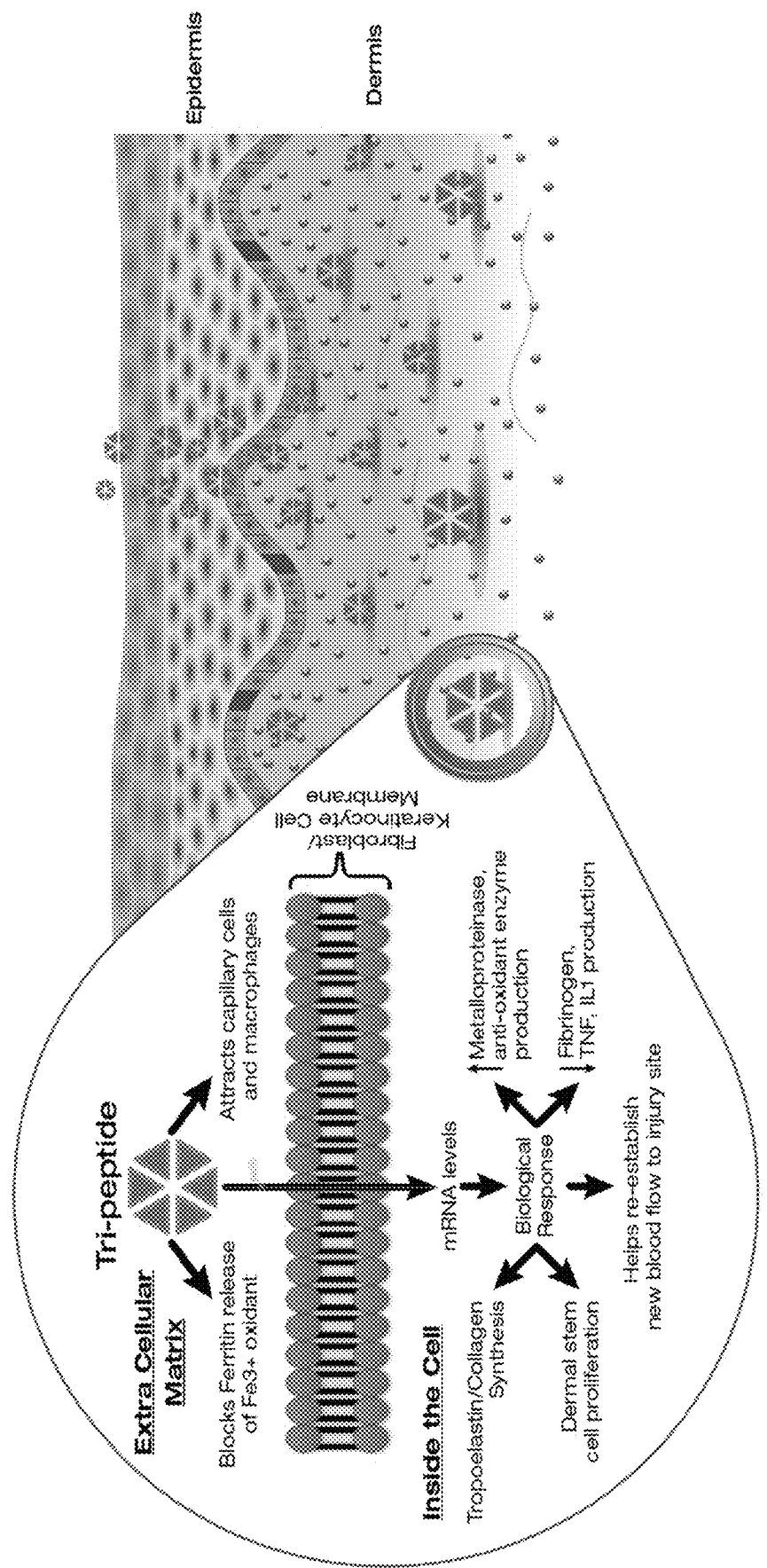
FIG. 2 depicts schematically a tripeptide's impact on promoting skin regeneration through increased collagen and elastin synthesis, blocking ferritin release of oxidized iron, attracting healing cells such as capillary cells and macrophages, and through re-establishing new blood flow to the injury site.

FIG. 2 provides a schematic diagram showing a tripeptide's impact on promoting skin regeneration through increased collagen and elastin synthesis, blocking ferritin release of oxidized iron, attracting healing cells such as capillary cells and macrophages, and through re-establishing new blood flow to the injury site. The tripeptide functions as an anti-oxidant, stimulates collage, elastin, and hyaluronic acid. It is formulated to penetrate stratum corneum. In the extracellular matrix (ECM), it is an anti-oxidant, attracts capillaries and macrophages, which facilitates wound healing. In the cell, it decreases inflammatory cytokines, increases collagen, elastin, dermal stem cell proliferation, and hyaluronic acid.

Figure 3:
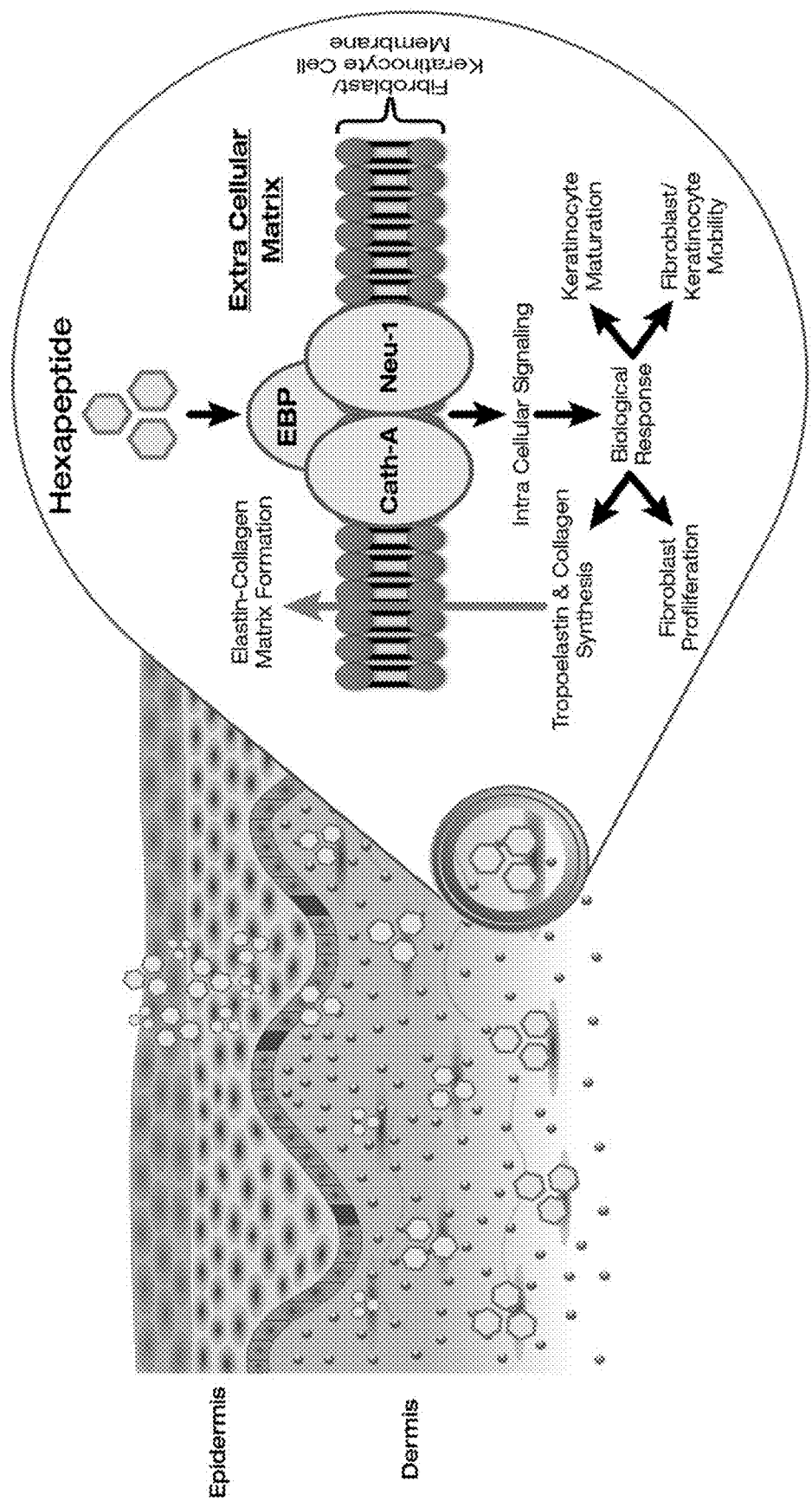
FIG. 3 depicts schematically a hexapeptide's impact on promoting skin regeneration and wound healing through the induction of elastin and collagen production, fibroblast proliferation, regeneration of the extracellular matrix, and fibroblast keratinocyte mobility.

FIG. 3 provides a schematic diagram showing a hexapeptide's impact on promoting skin regeneration and wound healing through the induction of elastin and collagen production, fibroblast proliferation, regeneration of the extracellular matrix, and fibroblast keratinocyte mobility. The hexapeptide is formulated to penetrate the stratum corneum, and mimics the elastin binding sequence, to stimulate elastin. It binds specifically to EBP receptors on fibroblasts and keratinocytes. The binding initiates intracellular signal transduction.

In topical formulations, the tripeptide is typically present in an amount of from about 50 ppm or less to about 100, 200, 300, 400, or 500 ppm or more, e.g., 50 ppm to 150 ppm.

In topical formulations, the hexapeptide is typically present in an amount of from about 50 ppm or less to about 100, 200, 300, 400, or 500 ppm or more, e.g., 50 ppm to 150 ppm.

The peptides can advantageously be provided in a base for suitable for combining with other components of a topical formulation. The base can include one or more components such as a thickener/binding agent (e.g., pentaerythrityl tetraisostearate), an emollient/dispersing agent (e.g., caprylic/capric triglyceride), a solvent (e.g., propylene carbonate), and/or a rheology modifier/antisetting agent (e.g., disteardimonium hectorite).

Oleuropein

In some embodiments, polyphenols such as oleuropein may be added to the compositions. Oleuropein is a polyphenol isolated from olive leaves (see e.g. Omar SH. Oleuropein in olive and its pharmacological effects. *Sci Pharm* 2010; 78(2): 133-54; Al-Rimawi F, Yateem H, Afaneh I. Formulation and evaluation of a moisturizing day cream containing olive leaves extract. International Journal of Development Research 2014; 4(10): 1996-2000; Kontogianni V G, Charisiadis P, Margianni E, Lamari F N, Gerothanassis I P, Tzakos A G. Olive leaf extracts are a natural source of advanced glycation end product inhibitors. Journal of medicinal food 2013; 16(9): 817-22). Oleuropein demonstrates major anti-inflammatory effects by inhibiting lypoxygenase activity and the production of leukotriene. More particularly researchers have demonstrated that oleuropein enhances proteasome activities in vitro more effectively than other known chemical activators, possibly through conformational changes of the proteasome. In this regard, it decreases reactive oxygen species (ROS), reduces the amount of oxidized proteins through increased proteasome-mediated degradation through increased proteasome-mediated degradation and autophagic pathways, and retains proteasome function during replicative senescence. Inhibition of AGE formation via blocking sugar attachment to proteins, scavenging the reactive intermediates, or breakdown of established AGE-induced cross-links constitutes an attractive therapeutic/preventive target. Oleuropein has been demonstrated to inhibit AGE formation and breakdown AGE products through its proteasome enhancing function. When oleuropein is employed in a topical formulation, it is preferably present at from about 0.005% by weight or less to about 10.0% by weight or more, typically at from about 0.01% by weight to about 5.0% by weight, e.g., at from about 0.05% by weight to about 0.1% by weight. Oleuropein is useful in compositions for promoting healing. Oleuropein is typically not employed in antiaging compositions, in that its effects tend to be incompatible with volumizing, but it can advantageously be employed in formulations for preconditioning the skin in advance of procedures as described herein (e.g., laser resurfacing, chemical peel, etc.).

Phosphatidyl Serine

In certain embodiments, phospholipids such as phosphatidylserine (PS), a highly enriched membrane phospholipid component, may be added. Phosphatidylserine has been known to have several physiological roles, such as activating signaling enzymes and antioxidant activity (see e.g. Draelos, Z., Pugliese, P. Glycation and Skin Aging: A Review. Cosmetics & Toiletries Magazine 2011; June 2011: 1-6; Lee, S., Yang, J., Park Y., et al. Protective effect and mechanism of phosphatidylserine in UVB-induced human dermal fibroblasts. European Journal of Lipid Science and Technology 2013; 115(7): 783-90; He, M., Kubo, H., Morimoto, K., et al. Receptor for advanced glycation end products binds to phosphatidylserine and assists in the clearance of apoptotic cells. EMBO reports 2011; 12(4): 358-64). It has been found to decrease MMP-1 in a dose dependent manner, to increase procollagen formation and may act as a substrate for AGE targets thus reducing the damage from glycation effects. Clearance of apoptotic cells is necessary for tissue development, homeostasis, and resolution of inflammation. Phosphatidylserine provides an "eat me" signal on the cell surface, and phagocytes recognize the signal using specific receptors such as the receptor of advanced glycation end-products (RAGE). This then binds to PS and assists in the clearance of apoptotic cells and end products of AGE. When phosphatidylserine is employed in a topical formulation, it is preferably present at from about 0.005% by weight or less to about 10.0% by weight or more, typically at from about 0.01% by weight to about 5.0% by weight, e.g., at from about 0.05% by weight to about 0.1% by weight.

Phosphatidylserine can advantageously be employed in formulations for preconditioning the skin in advance of procedures as described herein (e.g., laser resurfacing, chemical peel, etc.).

Carrier Systems

Liquids and gels containing the peptides and other components as described herein can be prepared using techniques as are known in the art of cosmetics manufacture. See, e.g., Handbook of Cosmetic Science and Technology, Fourth Edition, edited by André O. Barel, Marc Paye, Howard I. Maibach, CRC Press, 2014, the contents of which is hereby incorporated by reference in its entirety. Various formulations are possible. As an example, a clear cosmetic gel stick composition can include 60 to about 90% of an aliphatic polyhydric alcohol (e.g., a C2-6 alcohol containing from 2 to 6 hydroxyl groups); 1-10% of a soap; and 1-10% of a water-soluble emollient, e.g., a polyoxyalkylene ether of a C8-22 fatty alcohol, as the main ingredients, in combination with the peptides of the preferred embodiments. Aqueous extrudable gels are based on water-oil emulsion technologies. To minimize the amount of water introduced into an extrudable gel formula, the concentration of the active solution is adjusted. Ideally, a high concentration active solution (45-50%) of the peptides can be employed. Carrier systems for AP solids are typically based on volatile cyclic siloxanes because they evaporate quickly and do not leave residue on the skin. As an alternative to volatile cyclic siloxanes, alternatives can be used, including isohexadecane or C13-15 isoalkane. Solidification systems are employed to develop solid sticks that do not melt under typical storage or consumer conditions but provide an elegant skin feel and allow for easy transfer. A combination of cyclopentasiloxane and stearyl alcohol with varying degrees of additional waxes such as hydrogenated castor wax, hydrogenated vegetable oils and polyethylene, can be employed.

For liquid formulations (e.g., gel or lotion forms), a silicone, e.g., a cyclosiloxane or linear silicone (e.g., silicone elastomer), can be employed as a carrier. One type of suitable carrier is a dimethicone crosspolymer gel, e.g., dimethicone crosspolymer in cyclopentasiloxane. Other suitable dimethicone crosspolymers include cyclopentasiloxane, dimethicone/vinyldimethicone crosspolymer; dimethicone, dimethicone/vinyl dimethicone crosspolymer; and isodecane dimethicone/vinyl dimethicone crosspolymer.

Typically, the carrier is present in an amount of from about 80 wt. % to about 95 wt. %, or 82 wt. % to 92 wt. %, e.g., in a topical formulation for application to skin or mucous membranes.

Penetration Enhancers

Heptyl undecylenate can be employed to enhance penetration of the peptides, and to provide a silky feel to formulations. Other fatty acid esters can also be employed, e.g., methanoic acid, ethanoic acid, propanoic acid, butanoic acid, isobutyric acid, pentanoic acid, hexanoic acid, heptanoic acid, octanoic acid, nonanoic acid, decanoic acid, myristoleic acid, isovaleric acidpalmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, caprylic acid, capric acid, lauric acid, palmitic acid, stearic acid, arachidic acid, behenic acid, lignoceric acid, cerotic acid, medium chain fatty acids, e.g., $C_{6-12}$ fatty acids, or the like. Typical amounts when employed in topical formulations are from 1% by weight to 4% by weight. While heptyl undecylenate can advantageously be employed in most formulations, it can be considered an optional ingredient in glider formulations for use in conjunction with microneedling, and may be omitted for this use.

Anti-irritation Agents

Panthenyl triacetate/naringenin are natural plant extracts that reduce redness and water loss through the skin. Typical amounts for anti-irritation agents when employed in topical formulations are from 1% by weight to 4% by weight.

Anti-Inflammatory Agents

Arnica montana extract includes components such as essential oils, fatty acids, thymol, pseudoguaianolide sesquiterpene lactones and flavanone glycosides. It can exhibit an anti-inflammatory effect. Typical amounts for anti-inflammatory agents when employed in topical formulations are from 1% by weight to 4% by weight.

Antioxidant Agents

Dunaliella sauna extract includes components such as beta carotenes. It can exhibit an antioxidant effect. Typical amounts for anti-inflammatory agents when employed in topical formulations are from 0.1% by weight to 2% by weight.

Solubility Enhancers

Certain components of the formulation tend to be difficult to solubilize in conventional formulations. For example, phosphatidyl serine and oleuropein are known to exhibit solubility issues. It has been found that a siloxane polymer, e.g., caprylyl methicone, is particularly effective at solubilizing these two components in anhydrous formulations. For topical compositions containing from about 0.05% by weight to about 0.1% by weight phosphatidyl serine and/or from about 0.05% by weight to about 0.1% by weight oleuropein, caprylyl methicone in an amount of from about 0.5% by weight to about 1% by weight of caprylyl methicone can solubilize these components in an anhydrous formulation.

Hectorite Clays

Hectorite clays, such as modified hectorite clays, can be employed in conjunction with the peptides to provide impart penetration and adsorption properties to the compositions, and can aid in stabilizing emulsions. Hectorite has the chemical formula $Na_{0.3}(Mg,Li)_3Si_4O_{10}(OH)_2$. Other clays, such as bentonite and magnesium aluminum silicate can also be employed.

Hectorite or other clays can be modified to yield an organic modified clay compound. Salts (e.g., quaternary ammonium salts) of fatty acids (e.g., hydrogenated fatty acids) can be reacted with hectorite or other clays. As provided herein, fatty acids are referred to and described using conventional nomenclature as is employed by one of skill in the art. A saturated fatty acid includes no carbon-carbon double bonds. An unsaturated fatty acid includes at least one carbon-carbon double bond. A monounsaturated fatty acid includes only one carbon-carbon double bond. A polyunsaturated fatty acid includes two or more carbon-carbon double bonds. Double bonds in fatty acids are generally cis; however, trans double bonds are also possible. The position of double bonds can be indicated by Δn, where n indicates the lower numbered carbon of each pair of double-bonded carbon atoms. A shorthand notation specifying total # carbons: # double bonds, $\Delta_{double\ bond\ positions}$ can be employed. For example, $20:4\Delta_{5,8,11,14}$ refers to a fatty acid having 20 carbon atoms and four double bonds, with the double bonds situated between the 5 and 6 carbon atom, the 8 and 9 carbon atom, the 11 and 12 carbon atom, and the 14 and 15 carbon atom, with carbon atom 1 being the carbon of the carboxylic acid group. Stearate (octadecanoate) is a saturated fatty acid. Oleate (cis-Δ9-octadecenoate) is a monounsaturated fatty acid, linolenate (all-cis-Δ9,12,15-octadecatrienoate) is a polyunsaturated fatty acid. Fatty acids suitable for use can comprise from 5 to 30 carbon atoms, e.g., 5, 6, 7, 8, 9, 10, 11, 12, 13, 14, 15, 16, 17, 18, 19, 20, 21, 22, 23, 24, 25, 26, 27, 28, 29, or 30 carbon atoms. The fatty acid can be fully saturated, or can include as many double bonds as are feasible for the chain length. Fatty acids suitable for functionalizing hectorite or other clays include palmitic acid and stearic acid. Dialkyl quaternary cationic modifiers include dipalmoyldimonium chloride and distearyldimonium chloride. Amidoamine quaternary cationic modifiers include palmitamidopropyltrimonium chloride cetearyl alcohol and palmitamidopropyltrimonium chloride.

Other Excipients and Agents

In some embodiments, the peptides can be in admixture with a suitable carrier, diluent, or excipient, and can contain auxiliary substances such as wetting or emulsifying agents, pH buffering agents, gelling or viscosity enhancing additives, preservatives, scenting agents, colors, and the like, depending upon the route of administration and the preparation desired. See, e.g., "Remington: The Science and Practice of Pharmacy", Lippincott Williams & Wilkins; 20th edition (Jun.1, 2003) and "Remington's Pharmaceutical Sciences," Mack Pub. Co.; 18th and 19th editions (December 1985, and June 1990, respectively). Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulations include, without limitation, monoglycerides, diglycerides, sulfatides, lysolecithin, phospholipids, saponin, bile acids, and the like. The presence of such additional components can influence the physical state, solubility, stability, rate of release, rate of clearance, and penetration of active ingredients.

The compositions for topical administration comprise the peptide compositions as described herein and a dermatologically acceptable vehicle. The vehicle may be aqueous or nonaqueous. The dermatologically acceptable vehicle used in the topical composition may be in the form of a lotion, a gel, an ointment, a liquid, a cream, or an emulsion. If the vehicle is an emulsion, the emulsion may have a continuous aqueous phase and a discontinuous nonaqueous or oil phase (oil-in-water emulsion), or a continuous nonaqueous or oil phase and a discontinuous aqueous phase (water-in-oil emulsion). When administered topically in liquid or gel form, a liquid carrier such as water, petroleum, oils of animal or plant origin such as peanut oil, mineral oil, soybean oil, or sesame oil, or synthetic oils can be added to the active ingredient(s). Physiological saline solution, dextrose, or other saccharide solution, or glycols such as ethylene glycol, propylene glycol, or polyethylene glycol are also suitable liquid carriers. The pharmaceutical compositions can also be in the form of oil-in-water emulsions. The oily phase can be a vegetable oil, such as olive or arachis oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions can also contain coloring and scenting agents.

In certain embodiments, a silicone elastomer (e.g., dimethicone crosspolymer) is employed to increase delivery and penetration of the peptides into the skin. An alternative to increasing molecular weight (as with silicone gums) or adding filler (as with silicone compounds) is to partially crosslink siloxane polymers and disperse this material in an appropriate silicone carrier fluid. The resulting dimethicone crosspolymers (also known as silicone elastomers in the personal care industry) differ from basic polydimethylsiloxane (PDMS) because of the cross-linking between the linear polymers. These materials can be employed in peptide formulations, and also offer benefits in scar treatment, periwound protection and enzyme delivery. In skin care applications, the aesthetics of silicone elastomers (including those with functional groups) and their ability to absorb various oils (e.g., with a dimethicone/vinyl dimethicone crosspolymer such as Dow Corning® 9506 Elastomer Powder) are two of the elastomer's desirable properties. Silicone elastomers have a skin feel different from any of the silicone fluids, described as "smooth", "velvety" and "powdery". It can be modified by controlling the amount of liquid phase in the formula, and therefore the degree of swelling. Due to their film-forming properties, dimethicone crosspolymers can be used as delivery systems for active ingredients such as the peptides described herein, or other formulation components such as oil-soluble vitamins and sunscreens. Sunscreens such as octyl methoxycinnamate can be more efficiently delivered from a formulation containing a silicone elastomer, producing a higher sun protection factor (SPF). Silicone elastomer blends can be used to enhance SPF in oil-in-water formulations containing organic sunscreens. For example, in testing conducted regarding SPF, the addition of 4% silicone elastomer blend to a suncare formulation containing organic sunscreens increased the SPF from 5.7 to 18. This property of the silicone elastomer allows the effectiveness of sunscreen agents in a formulation to be maximized while reducing the amount needed to achieve a desired SPF. As a result, formulation costs can be reduced along with potential irritation caused by sunscreen actives. Accordingly, a higher SPF can be achieved with the same amount of UV absorber, resulting in enhanced performance with no added formulation cost. Silicone elastomers can be produced from linear silicone polymers by a variety of crosslinking reactions, e.g., by a hydrosilylation reaction in which a vinyl group reacts with a silicon hydride. The general process involves linear silicone polymers with reactive sites along the polymer chain reacting with a cross-linker. The dimethicone crosspolymer can be produced either as a gel made of a suspension of elastomer particles swollen in a carrier fluid (e.g., a mixture of high molecular weight silicone elastomer in cyclopentasiloxane such as Dow Corning® 9040 Silicone Elastomer Blend), or as a spray-dried powder (a dimethicone/vinyl dimethicone crosspolymer such as Dow Corning® 9506 Elastomer Powder). The gel form having desirable attributes is cyclomethicone, but low viscosity dimethicones and organic fluids can also be used. Examples of dimethicone crosspolymers in the suspension or gel form are high molecular weight silicone elastomer (12%) in decamethylcyclopentasiloxane (e.g., Dow Corning® ST-Elastomer 10) and a mixture of high molecular weight silicone elastomer in cyclopentasiloxane (e.g., Dow Corning® 9040 Silicone Elastomer Blend), which typically have an elastomer content ranging from 10 to 20% by weight.

The pharmaceutical excipients used in the topical preparations of the peptide compositions may be selected from the group consisting of solvents, emollients and/or emulsifiers, oil bases, preservatives, antioxidants, tonicity adjusters, penetration enhancers and solubilizers, chelating agents, buffering agents, surfactants, one or more polymers, and combinations thereof.

Suitable solvents for an aqueous or hydrophilic topical formulation include water; ethyl alcohol; isopropyl alcohol; mixtures of water and ethyl and/or isopropyl alcohols; glycerin; ethylene, propylene or butylene glycols; DMSO; and mixtures thereof. Suitable solvents for hydrophobic topical formulations include mineral oils, vegetable oils, and silicone oils. If desired, the peptide compositions as described herein may be dissolved or dispersed in a hydrophobic oil phase, and the oil phase may then be emulsified in an aqueous phase comprising water, alone or in combination with lower alcohols, glycerin, and/or glycols. It is generally preferred to employ anhydrous compositions, as the presence of water can result in stinging upon administration to skin tissues subject to laser treatment, chemical peel, dermabrasion, or the like. Anhydrous formulations may also act to prevent the development of water-based irritant contact dermatitis in damaged or sensitive skin, which may produce rashes and skin irritation that may retard wound healing and improvement in skin quality. Tsai, T. F., Maibach, H. I. How irritant is water? An overview. Contact Dermatitis 41(6) (1999): 311-314 (describing contact dermatitis caused by water as an irritant). However, in certain embodiments it may be acceptable to provide water based compositions, or to permit a limited amount of water to be present. For example, water may be present, but at amounts below the threshold at which a stinging sensation when applied to damaged skin may result. Osmotic shock or osmotic stress is a sudden change in the solute concentration around a cell, causing a rapid change in the movement of water across its cell membrane. Under conditions of high concentrations of either salts, substrates or any solute in the supernatant, water is drawn out of the cells through osmosis. This also inhibits the transport of substrates and cofactors into the cell thus "shocking" the cell. Alternatively, at low concentrations of solutes, water enters the cell in large amounts, causing it to swell and either burst or undergo apoptosis. Certain of the formulations as described herein can be advantageously employed where it is desirable to minimize osmotic shock.

Viscosity of the compositions can be maintained at the selected level using a pharmaceutically acceptable thickening agent. Suitable viscosity enhancers or thickeners which may be used to prepare a viscous gel or cream with an aqueous base include sodium polyacrylate, xanthan gum, polyvinyl pyrrolidone, acrylic acid polymer, carragenans, hydroxyethyl cellulose, hydroxypropyl cellulose, methyl cellulose, ethyl cellulose, propyl cellulose, hydroxypropyl methyl cellulose, polyethoxylated polyacrylamides, polyethoxylated acrylates, and polyethoxylated alkane thiols. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the thickening agent selected. An amount is preferably used that will achieve the selected viscosity. Viscous compositions are normally prepared from solutions by the addition of such thickening agents, or by employing a base that has an acceptable level of viscosity.

Suitable emollients include hydrocarbon oils and waxes such as mineral oil, petrolatum, paraffin, ceresin, ozokerite, microcrystalline wax, polyethylene, squalene, perhydrosqualene, silicone oils, triglyceride esters, acetoglyceride esters, such as acetylated monoglycerides; ethoxylated glycerides, such as ethoxylated glyceryl monostearate; alkyl esters of fatty acids or dicarboxylic acids.

Suitable silicone oils for use as emollients include dimethyl polysiloxanes, methyl(phenyl) polysiloxanes, and water-soluble and alcohol-soluble silicone glycol copolymers. Suitable triglyceride esters for use as emollients include vegetable and animal fats and oils including castor oil, safflower oil, cotton seed oil, corn oil, olive oil, cod liver oil, almond oil, avocado oil, palm oil, sesame oil, and soybean oil.

Suitable esters of carboxylic acids or diacids for use as emollients include methyl, isopropyl, and butyl esters of fatty acids. Specific examples of alkyl esters including hexyl laurate, isohexyl laurate, iso-hexyl palmitate, isopropyl palmitate, decyl oleate, isodecyl oleate, hexadecyl stearate, decyl stearate, isopropyl isostearate, dilauryl lactate, myristyl lactate, and cetyl lactate; and alkenyl esters of fatty acids such as oleyl myristate, oleyl stearate, and oleyl oleate. Specific examples of alkyl esters of diacids include diisopropyl adipate, diisohexyl adipate, bis(hexyldecyl) adipate, and diisopropyl sebacate.

Other suitable classes of emollients or emulsifiers which may be used in the topical formulations include fatty acids, fatty alcohols, fatty alcohol ethers, ethoxylated fatty alcohols, fatty acid esters of ethoxylated fatty alcohols, and waxes.

Specific examples of fatty acids for use as emollients include pelargonic, lauric, myristic, palmitic, stearic, isostearic, hydroxystearic, oleic, linoleic, ricinoleic, arachidic, behenic, and erucic acids. Specific examples of fatty alcohols for use as emollients include lauryl, myristyl, cetyl, hexadecyl, stearyl, isostearyl, hydroxystearyl, oleyl, ricinoleyl, behenyl, and erucyl alcohols, as well as 2-octyl dodecanol.

Specific examples of waxes suitable for use as emollients include lanolin and derivatives thereof including lanolin oil, lanolin wax, lanolin alcohols, lanolin fatty acids, isopropyl lanolate, ethoxylated lanolin, ethoxylated lanolin alcohols, ethoxolated cholesterol, propoxylated lanolin alcohols, acetylated lanolin, acetylated lanolin alcohols, lanolin alcohols linoleate, lanolin alcohols recinoleate, acetate of lanolin alcohols recinoleate, acetate of lanolin alcohols recinoleate, acetate of ethoxylated alcohols esters, hydrogenolysates of lanolin, hydrogenated lanolin, ethoxylated hydrogenated lanolin, ethoxylated sorbitol lanolin, and liquid and semi-solid lanolin. Also usable as waxes include hydrocarbon waxes, ester waxes, and amide waxes. Useful waxes include wax esters such as beeswax, spermaceti, myristyl myristate and stearyl stearate; beeswax derivatives, e.g., polyoxyethylene sorbitol beeswax; and vegetable waxes including carnauba and candelilla waxes.

Polyhydric alcohols and polyether derivatives may be used as solvents and/or surfactants in the topical formulations. Suitable polyhydric alcohols and polyethers include propylene glycol, dipropylene glycol, polypropylene glycols 2000 and 4000, poly(oxyethylene-co-oxypropylene) glycols, glycerol, sorbitol, ethoxylated sorbitol, hydroxypropylsorbitol, polyethylene glycols 200-6000, methoxy polyethylene glycols 350, 550, 750, 2000 and 5000, poly[ethylene oxide] homopolymers (100,000-5,000,000), polyalkylene glycols and derivatives, hexylene glycol, 2-methyl-2,4-pentanediol, 1,3-butylene glycol, 1,2,6-hexanetriol, 2-ethyl-1, 3-hexanediol, vicinal glycols having 15 to 18 carbon atoms, and polyoxypropylene derivatives of trimethylolpropane.

Polyhydric alcohol esters may be used as emulsifiers or emollients. Suitable polyhydric alcohol esters include ethylene glycol mono- and di-fatty acid esters, diethylene glycol mono- and di-fatty acid esters, polyethylene glycol (200-6000) mono- and di-fatty acid esters, propylene glycol mono- and di-fatty esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Suitable emulsifiers for use in topical formulations include anionic, cationic, nonionic, and zwitterionic surfactants. Preferred ionic emulsifiers include phospholipids, such as lecithin and derivatives.

Lecithin and other phospholipids may be used to prepare liposomes containing the peptide compositions as described herein. Formation of lipid vesicles occurs when phospholipids such as lecithin are placed in water and consequently form one bilayer or a series of bilayers, each separated by water molecules, once enough energy is supplied. Liposomes can be created by sonicating phospholipids in water. Low shear rates create multilamellar liposomes. Continued high-shear sonication tends to form smaller unilamellar liposomes. Hydrophobic chemicals can be dissolved into the phospholipid bilayer membrane. The lipid bilayers of the liposomes deliver the peptide compositions as described herein.

The topical formulation may contain micelles, or an aggregate of surfactant molecules dispersed in an aqueous solution. Micelles may be prepared by dispersing an oil solvent in an aqueous solution comprising a surfactant, where the surfactant concentration exceeds the critical micelle concentration. The resulting formulation contains micelles, i.e., spherical oil droplets surrounded by a membrane of polar surfactant molecules, dispersed in the aqueous solvent.

Sterols including, for example, cholesterol and cholesterol fatty acid esters; amides such as fatty acid amides, ethoxylated fatty acid amides, and fatty acid alkanolamides may also be used as emollients and/or penetration enhancers.

A pharmaceutically acceptable preservative can be employed to increase the shelf life of the composition. Other suitable preservatives and/or antioxidants for use in topical formulations include benzalkonium chloride, benzyl alcohol, phenol, urea, parabens, butylated hydroxytoluene (BHT), butylated hydroxyanisole (BHA), tocopherol, thimerosal, chlorobutanol, or the like, and mixtures thereof, can be employed. If a preservative, such as an antioxidant, is employed, the concentration is typically from about 0.02% to about 2% based on the total weight of the composition, although larger or smaller amounts can be desirable depending upon the agent selected. Reducing agents, as described herein, can be advantageously used to maintain good shelf life of the formulation. It is generally observed that the anhydrous formulations of the embodiments exhibit satisfactory stability, such that a preservative can be omitted from the formulation.

Suitable chelating agents for use in topical formulations include ethylene diamine tetraacetic acid, alkali metal salts thereof alkaline earth metal salts thereof, ammonium salts thereof, and tetraalkyl ammonium salts thereof.

The carrier preferably has a pH of between about 4.0 and 10.0, more preferably between about 6.8 and about 7.8. The pH may be controlled using buffer solutions or other pH modifying agents. Suitable pH modifying agents include phosphoric acid and/or phosphate salts, citric acid and/or citrate salts, hydroxide salts (i.e., calcium hydroxide, sodium hydroxide, potassium hydroxide) and amines, such as triethanolamine. Suitable buffer solutions include a buffer comprising a solution of monopotassium phosphate and dipotassium phosphate, maintaining a pH of between 5.8 and 8; and a buffer comprising a solution of monosodium phosphate and disodium phosphate, maintaining a pH of between 6 and 7.5. Other buffers include citric acid/sodium citrate, and dibasic sodium phosphate/citric acid. The peptide compositions of the embodiments are preferably isotonic with the blood or other body fluid of the recipient. The isotonicity of the compositions can be attained using sodium tartrate, propylene glycol or other inorganic or organic solutes. Sodium chloride is particularly preferred. Buffering agents can be employed, such as acetic acid and salts, citric acid and salts, boric acid and salts, and phosphoric acid and salts. It can be desirable to include a reducing agent in the formulation, such as vitamin C, vitamin E, or other reducing agents as are known in the pharmaceutical arts.

Surfactants can also be employed as excipients, for example, anionic detergents such as sodium lauryl sulfate, dioctyl sodium sulfosuccinate and dioctyl sodium sulfonate, cationic such as benzalkonium chloride or benzethonium chloride, or nonionic detergents such as polyoxyethylene hydrogenated castor oil, glycerol monostearate, polysorbates, sucrose fatty acid ester, methyl cellulose, or carboxymethyl cellulose.

When the peptide formulations of the embodiments are administered by subcutaneous injection, it is preferably in the form of a pyrogen-free, parenterally acceptable aqueous solution or oleaginous suspension, emulsion or solution. Suspensions can be formulated according to methods well known in the art using suitable dispersing or wetting agents and suspending agents. The preparation of acceptable aqueous or nonaqueous solutions with suitable properties, e.g., pH, isotonicity, stability, and the like, is within the skill in the art. For example, an isotonic vehicle such as 1,3-butanediol, water, isotonic sodium chloride solution, Ringer's solution, dextrose solution, dextrose and sodium chloride solution, lactated Ringer's solution, or other vehicles as are known in the art can be employed, or a fixed oil can be employed conventionally as a solvent or suspending medium, e.g., synthetic mono or diglycerides, fatty acids, or the like. The peptide formulations can also contain stabilisers, preservatives, buffers, antioxidants, or other additives known to those of skill in the art.

In certain embodiments, it can be advantageous to include additional agents having pharmacological activity. Anti-infective agents include, but are not limited to, anthelmintic (mebendazole), antibiotics including aminoglycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin, clindamycin, colistimethate sodium, polymyxin b sulfate, vancomycin, antivirals including acyclovir, amantadine, didanosine, efavirenz, foscarnet, ganciclovir, indinavir, lamivudine, nelfinavir, ritonavir, saquinavir, stavudine, valacyclovir, valganciclovir, zidovudine, quinolones (ciprofloxacin, levofloxacin), sulfonamides (sulfadiazine, sulfisoxazole), sulfones (dapsone), furazolidone, metronidazole, pentamidine, sulfanilamidum crystallinum, gatifloxacin, and sulfamethoxazole/trimethoprim. Anesthetics can include, but are not limited to, ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocaine, and phenazopyridine. Anti-inflammatory agents include but are not limited to, nonsteroidal anti-inflammatory drugs (NSAIDs) such as aspirin, celecoxib, choline magnesium trisalicylate, diclofenac potassium, diclofenac sodium, diflunisal, etodolac, fenoprofen, flurbiprofen, ibuprofen, indomethacin, ketoprofen, ketorolac, melenamic acid, nabumetone, naproxen, naproxen sodium, oxaprozin, piroxicam, rofecoxib, salsalate, sulindac, and tolmetin; and corticosteroids such as cortisone, hydrocortisone, methylprednisolone, prednisone, prednisolone, betamethesone, beclomethasone dipropionate, budesonide, dexamethasone sodium phosphate, flunisolide, fluticasone propionate, triamcinolone acetonide, betamethasone, fluocinonide, betamethasone dipropionate, betamethasone valerate, desonide, desoximetasone, fluocinolone, triamcinolone, clobetasol propionate, and dexamethasone.

In certain embodiments, the addition of emollients, emulsion stabilisers, moisturizers, excipients, and other compounds may be modified to enhance the sensory properties of the topical compositions, including but not limited to: skin feel (silkiness, lightness, creaminess, etc.), absorbency (required time at which product loses wet feel and is no longer perceived on skin), consistency, firmness, spreadability (e.g. viscosity, flow onset, shear rates), stickiness, integrity of shape, glossiness, hydrophilicity or hydrophobicity, and others. Preferably, compositions will have high spreadability and low viscosity properties. Compositions with such properties have been demonstrated to have an enhanced "silky" or "light" skin feel rating (see e.g. Bekker, M. Webber, G., Louw, N. Relating rheological measurements to primary and secondary skin feeling when mineral-based and Fischer-Tropsch wax-based cosmetic emulsions and jellies are applied to the skin, International Journal of Cosmetic Science 2013, 35(4), pp. 354-61).

The compositions can be advantageously employed as a carrier for platelet-rich plasma (PRP), which is blood plasma that has been enriched with platelets. As a concentrated source of autologous platelets, PRP contains several different growth factors and other cytokines that can stimulate healing of soft tissue. Platelet rich plasma therapy utilizes growth factors present in alpha granules of platelets in an autologous manner, e.g., for treatment of androgenetic alopecia, in wound healing, in facial rejuvenation, or the like For preparation of PRP, various protocols are used and no standard protocol exists but main principles essentially involve concentrating platelets in a concentration of 3-5 times the physiological value and then injecting this concentrated plasma in the tissue where healing or effect is desired. Such formulations can be particularly advantageous in vaginal rejuvenation applications.

Stability Testing

Stability testing of the topical formulations can be conducted as follows.

High temperature testing is now commonly used as a predictor of long-term stability. High temperature testing can be conducted at 37° C. (98 F) and 45° C. (113° F.). If a product is stored at 45° C. for three months (and exhibits acceptable stability) then it should be stable at room temperature for two years. Of course, the product must be stored at 25° C. (77° F.) for a period of one year. A good control temperature is 4° C. (39° F.) where most products will exhibit excellent stability. The product should also be subjected to −10° C. (14° F.) for three months.

The product should pass three cycles of temperature testing from −10° C. (14° F.) to 25° C. (77° F.). The product is placed at −10° C. for 24 hours and place it at room temperature (25° C.) for 24 hours. This completes one cycle. If the product passes three cycles then you can have a good degree of confidence in the stability of the product. An even more rigorous test is a −10° C. to 45° C. five-cycle test. This puts emulsions under a tremendous stress and, if it passes the test, indicates that you have a highly stable product.

The dispersed phase (of an oil-in-water emulsion) has a tendency to separate and rise to the top of the emulsion forming a layer of oil droplets. This phenomenon is called creaming. Creaming is one of the first signs of impending emulsion instability. A test method to predict creaming is centrifugation. Heat the emulsion to 50° C. (122° F.) and centrifuge it for thirty minutes at 3000 rpm. Then inspect the resultant product for signs of creaming.

Both formulas and packaging can be sensitive to the UV radiation. The product is placed in glass and the actual package in a light box that has a broad-spectrum output. Another glass jar completely covered with aluminum foil serves as a control. Discoloration of the product may be observed.

For all the above mentioned tests the color, odor/fragrance, viscosity, pH value, and, if available, particle size uniformity and/or particle agglomeration under the microscope can be observed.

Kits for Non-Invasive Use and Use with Invasive Procedures

Some embodiments of the methods and compositions provided herein include kits comprising peptides provided herein. In some embodiments, kits can be provided to an administering physician, other health care professional, a patient, or a caregiver. In some embodiments, a kit comprises a container which contains the peptide compositions in a suitable topical formulation, and instructions for administering the peptide composition to a subject. The kit can optionally also contain one or more additional therapeutic or other agents. For example, a kit containing a peptide composition in topical form can be provided along with other skin care agents, such as, cleansers, occlusive moisturizers, penetrating moisturizers, sunscreens, sunblocks, and the like. The kit may contain the peptide composition in bulk form, or can contain separate doses of the peptide composition for serial or sequential administration. The kit can optionally contain one or more diagnostic tools, administration tools, and/or instructions for use. The kit can contain suitable delivery devices, such as, syringes, pump dispensers, single dose packets, and the like, along with instructions for administering the peptide compositions and any other therapeutic or beneficial agents. The kit can optionally contain instructions for storage, reconstitution (if applicable), and administration of any or all therapeutic or beneficial agents included. The kits can include a plurality of containers reflecting the number of administrations to be given to a subject, or the different products to be administered to the subject.

The topical peptide formulation, in addition to the tripeptide and hexapeptide as described herein such as, as palmitoyl hexapeptide-12 and palmitoyl tripeptide-1, can contain other ingredients. For example, other ingredients can include cyclopentasiloxane, dimethicone crosspolymer, pentaerythrityl tetraisostearate, heptyl undecylenate, glycine soja (soybean) oil, panthenyl triacetate, narigenin, arnica montana extract, dunaliella salina extract, disteardimonium hectorite, tocopherol, squalane, caprylic/capric triglyceride, stearalkonium hectorite, and propylene carbonate. In some embodiments, the formulation is configured to support the skin before, during and after cosmetic procedures, and also works with the skin's own natural regenerating process and assists in improving the skin's appearance. The topical peptide formulation can be applied immediately post-procedure for faster recovery, or generally for healthier looking skin. The peptide formulation can increase natural levels of elastin in the skin, improves the quality of existing elastin, stimulates increase in collagen production, and exhibits high antioxidant activity to reduce inflammation, redness and irritation. The topical peptide formulation is suitable for all skin types and post-procedure skin. The topical formulations can be provided to the patient in bulk form, to permit a suitable amount of the peptides to be self-administered by the patient. For example, the patient can apply an amount of the formulation sufficient to provide an even coating over the affected area or as otherwise instructed by the physician. In certain embodiments it can desirable to incorporate additional therapeutic or active agents into the topical formulation. Alternatively, adjunct therapies or agents can be administered separately. For example, a cleanser, a sunblock, a sunscreen, a penetrating moisturizer, and/or an occlusive moisturizer can be provided for administration before or after the topical composition of the embodiments.

The topical peptide compositions can be used in conjunction with a gentle cleanser. The gentle, self-foaming cleanser removes impurities from the skin without drying or irritating the skin. The gentle cleanser can contain a blend of moisturizers and vitamins designed to clean, soothe and soften the skin without upsetting the skin's delicate moisture balance. In use, the cleanser softens, soothes and moisturizes skin, thoroughly removes environmental pollutants and make-up, is sulfate-free, and is suitable for use post-procedure on sensitive skin. In one embodiment, the gentle cleanser comprises water, sodium C14-16 olefin sulfonate, cocamidopropyl betaine, acrylates copolymer, PEG/PPG-8/3 diisostearate, avena satvia (oat) kernel extract, panthenol, glycerin, beta glucan, bisabolol, *Lavandula angustifolia* (lavender) oil, citrus *Aurantium dulcis* (orange) peel oil, titanium dioxide, tin oxide, synthetic fluorphlogopite, disodium EDTA, phenoxyethanol, ethylhexylglycerin, citric acid, and sodium hydroxide.

The topical peptide compositions can be used in conjunction with an occlusive moisturizer. The occlusive moisturizer is an ointment formulated to moisturize the skin and work with the body's own natural rejuvenating processes immediately following cosmetic procedures. It protects and enhances post-procedure outcomes for skin. The occlusive moisturizer softens, soothes and moisturizes skin, supports renewal of post-procedure skin, helps restore the skin's moisture balance, hydrates dry and compromised skin, and is suitable for post-procedure skin and extremely dry skin. In one embodiment, the occlusive moisturizer comprises petrolatum, microcrystalline wax, *Physalis angulata* extract, caprylic/capric triglyceride, *Butyrospermum parki* (shea butter) extract, bisabolol, and tocopherol.

The topical peptide compositions can be used in conjunction with a penetrating moisturizer. The moisturizer is a ceramide rich, hydrating moisturizer formulated to help rebuild the skin's natural barrier function, which can be compromised following cosmetic procedures. The moisturizer contains moisture building ingredients, antioxidants, and soothing phyto-nutrients that help promote and maintain the barrier function of the skin. The moisturizer helps to restore moisture balance, soften, soothe and hydrate skin, inhibit free radicals, and replenish and brighten dull, dry skin. The moisturizer is suitable for all skin types and post-procedure skin. In on embodiment, the penetrating moisturizer comprises water, caprylic/capric triglyceride, cetyl ethylhexanoate, cetaryl alcohol, squalane, niacinamide, dimethicone, cetearyl glucoside, glyceryl stearate, PEG-100 stearate, propanediol, ceramide 3, phytosterols, *Butyrospermum parklii* (shea butter) extract, *Butyrospermum parklii* (shea butter), olea europeaea (olive) fruit oil, sodium hyaluronate, beta-glucan, hydrolyzed pea protein, Dunaliella salina extract, xylitylglucoside, anhydroxylitol, xylitol, glycerin, lecithin, caprylyl glycol, caprylhydroxamic acid, xanthan gum, disodium EDTA, ethylhexylglycerin, and phenoxyethanol.

The topical peptide compositions can be used in conjunction with a sunscreen. The sunscreen can be of a suitable SPF, such as SPF 10+, SPF 15+, SPF 20+, SPF 30+, SPF 40+, SPF 50+, or higher. The sunscreen can be a broad spectrum and water resistant, such as 80 minutes or more) sunscreen. The sunscreen can include antioxidants, hydrators and skin soothing phytonutrients. The sunscreen can be used daily and immediately following facial treatments. The sunscreen provides broad spectrum UVA/UVB sun protection, moisturizing UV protection for the face, is non-comedogenic, is suitable for use post-procedure, is fragrance-free and paraben-free. Active ingredients of the sunscreen can include zinc oxide (e.g., 10% by weight) and octinoxate (e.g., 7.5% by weight). In one embodiment, the sunscreen comprises water, ethylhexyl palmitate, cyclomethicone, dimethicone, laurylmethicone copolyol, butylene glycol, tocopherol acetate, sodium chloride, aleurites moluccana (kukui nut) seed oil, emelia sinensis leaf (green tea) extract, cucmis staivus (cucumber) fruit extract, aloe barbadensis (aloe vera) leaf extract, tetrahexyldecyl ascorbate, allantoin, sodium hyaluronate, disodium EDTA, methylisothiazolinone, ethylhexlglycerin, and fragrance.

In one embodiment, a kit is provided for use in connection with an invasive skin procedure, as described herein. The kit, termed "an invasive kit", includes a topical peptide composition, an occlusive moisturizer, a gentle cleanser, a penetrating moisturizer, and a broad spectrum SPF 30+sunscreen.

In another embodiment, a kit is provided for use in connection with improving skin health but not in connection with an invasive skin procedure. The kit, termed "a noninvasive kit", includes a topical peptide composition, a gentle cleanser, a penetrating moisturizer, and a broad spectrum SPF 30+ sunscreen.

The various examples of creams, ointments, lotions, solutions, gels, sprays and patches may incorporate the peptide compositions as described herein as the active ingredient, in combination with penetration enhancing agents and other active agents acting synergistically on the skin for the promotion of wound healing or wound closure or the treatment of chronic cutaneous wound.

Oral Supplements

While topical administration of the peptides of disclosed herein can advantageously be employed, in certain embodiments systemic administration can be desirable. In such embodiments, the peptides are formulated into a composition suitable for oral administration, but other routes of administration are also contemplated.

The peptide compositions described herein can be administered by themselves to a subject, or in compositions where they are mixed with other active agents, as in combination therapy, or with carriers, diluents, excipients or combinations thereof. Formulation is dependent upon the route of administration chosen. Techniques for formulation and administration of the compounds described herein are known to those skilled in the art (see, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively).

The peptide combinations disclosed herein may be manufactured into administrable forms by a process that is itself known, e.g., by means of conventional mixing, dissolving, granulating, dragee-making, levigating, emulsifying, encapsulating, entrapping, tableting, or extracting processes.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. Contemplated herein is any combination of the forgoing, or other methods as would be known to one of ordinary skill in the art (see, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively).

In practice, the peptides may be combined as the active ingredient in intimate admixture with a pharmaceutical carrier according to conventional pharmaceutical compounding techniques. The ratio of the peptides to each other is maintained as in the topical formulation, however, excipients are preferably minimized so as to ensure administration of an appropriate amount of peptides in a compact format. In its simplest form, the peptides can be added directly to, e.g., a gelatin capsule or a softgel capsule for consumption by the patient. In other embodiments, carriers can be employed. The carrier can take a wide variety of forms depending on the form of preparation desired for administration. Thus, the peptide compositions provided herein can be presented as discrete units suitable for oral administration such as capsules, cachets or tablets each containing a predetermined amount of the active ingredient. Further, the peptide compositions can be presented as an oil, a powder, as granules, as a solution, as a suspension in an aqueous liquid, as a non-aqueous liquid, as an oil-in-water emulsion, or as a water-in-oil liquid emulsion, similar to the topical formulations described elsewhere herein, but using components suitable for human consumption. In addition to the common dosage forms set out above, the peptide compositions provided herein can also be administered by controlled release and/or delivery devices. The peptide compositions can be prepared by any of the methods of pharmacy. In general, such methods include a step of bringing into association the active ingredient with the carrier that constitutes one or more necessary ingredients. In general, the peptide compositions are prepared by uniformly and intimately admixing the peptide ingredients with liquid carriers or finely divided solid carriers or both. The product can then be conveniently shaped into the desired presentation.

A peptide formulation may also be administered in a local rather than systemic manner, for example, via injection of the peptide composition directly into a target area, e.g., in a depot or sustained release formulation. Furthermore, a targeted drug delivery system for the peptide may be used, for example, in a liposome coated with a tissue specific antibody.

The peptide compositions may contain the peptides in an amount effective for the desired therapeutic effect. In some embodiments, the peptide compositions are in a unit dosage form and comprise from about 0.1 mg or less to about 5000 mg or more of peptides per unit dosage form. In further embodiments, the peptide compositions comprise from about 1 to about 500 mg per unit dosage form or from about 500 to 5000 mg per unit dosage form of peptides. Such dosage forms may be solid, semisolid, liquid, an emulsion, or adapted for delivery via aerosol or the like.

The carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, lower alcohols, and water. Examples of gaseous carriers include carbon dioxide and nitrogen.

Peptide compositions provided herein can be prepared as solutions or suspensions of the peptides in water or non-aqueous liquids. A suitable surfactant can be included such as, for example, hydroxypropylcellulose. Dispersions can also be prepared in glycerol, liquid polyethylene glycols, and mixtures thereof in oils. Further, a preservative can be included to, for example, prevent the detrimental growth of microorganisms.

Peptide compositions provided herein suitable for injectable use include sterile aqueous solutions or dispersions. Furthermore, the peptide compositions can be in the form of sterile powders for the extemporaneous preparation of such sterile injectable solutions or dispersions. The peptide compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

In addition to the aforementioned carrier ingredients, the peptide formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood or other bodily fluids of the intended recipient. Peptide compositions can also be prepared in powder or liquid concentrate form for dilution.

Contemplated herein are peptide compositions including the peptides as described herein in combination with at least one additional active agent. The peptides and the at least one additional active agent(s) may be present in a single formulation or in multiple formulations provided together, or may be unformulated. In some embodiments, the peptides can be administered with one or more additional agents together in a single composition. For example, the peptides can be administered in one composition, and at least one of the additional agents can be administered in a second composition. In a further embodiment, the peptide and the at least one additional active agent(s) are co-packaged in a kit. For example, a drug manufacturer, a drug reseller, a physician, a compounding shop, or a pharmacist can provide a kit comprising the peptide in combination with another product or component for delivery to a patient. Such additional components can include anti-infective agents, anti-inflammatory agents, anesthetics, or the like.

Some embodiments described herein relate to oral compositions of peptides, which can include a therapeutically effective amount of the peptides described herein and a pharmaceutically acceptable carrier, diluent, excipient or combination thereof. The peptide composition can include the peptides in an amount for example, >1%, ≥2%, ≥3%, ≥4%, ≥5%, ≥6%, ≥7%, ≥8%, ≥9%, ≥10%, ≥20%, ≥30%, ≥40%, ≥50%, ≥60%, ≥70%, ≥80%, ≥90%, ≥95%, or ≥98% of the composition. As described elsewhere herein, the first peptide and second peptide are present in the composition at a weight ratio of 1 part of the first peptide (or first peptides) to about 1 to 2 parts of the second peptide (or second peptides).

EXAMPLES

Example 1A

Peptide Formulations

Several peptide-containing topical formulations were prepared comprising a first peptide and a second peptide in combination with excipients. The formulations so prepared were evaluated for suitability for use as a topical formulation, including skin feel and stability. The formulations were prepared as in the following tables.

| Formula 1A | |
|---|---|
| Ingredient | % (wt.) |
| Isododecane (and) Dimethicone Crosspolymer-3 | 95.468 |
| Physalis Angulata Extract | 1.000 |
| Arnica Montana Extract | 2.000 |
| Centella Asiatica Extract | 0.250 |
| Squalane | 1.000 |
| Growth Hormone Releasing Peptide-6 | 0.032 |
| 1,3 Propanediol | 0.250 |

| Formula 2A | |
|---|---|
| Ingredient | % (wt.) |
| Isododecane (and) Dimethicone Crosspolymer-3 | 92.718 |
| Panthenyl Triacetate/Naringenin | 2.000 |
| Arnica Montana Extract | 2.000 |
| Dunaliella Salina Extract | 1.000 |
| Squalane | 2.000 |
| Growth Hormone Releasing Peptide-2 | 0.032 |
| 1,3 Propanediol | 0.250 |

| Formula 3A | |
|---|---|
| Ingredient | % (wt.) |
| Cyclopentasiloxane, Polysilicone-11 | 92.718 |
| Panthenyl Triacetate/Naringenin | 2.000 |
| Arnica Montana Extract | 2.000 |
| Dunaliella Salina Extract | 1.000 |
| Squalane | 2.000 |
| Growth Hormone Releasing Peptide-2 | 0.032 |
| 1,3 Propanediol | 0.250 |

| Formula 4A | |
|---|---|
| Ingredient | % (wt.) |
| Isododecane (and) Dimethicone Crosspolymer-3 | 87.500 |
| Panthenyl Triacetate/Naringenin | 2.000 |
| Arnica Montana Extract | 2.000 |
| Dunaliella Salina Extract | 1.000 |
| Squalane | 2.000 |
| Carrier: | 5.500 |
| Penta erythrityl tetraisostearate | |
| Caprylic/capric triglyceride | |
| Propylene carbonate | |
| Stearalkonium hectorite | |
| Palmitoyl hexapeptide-12 (@ 100 ppm in carrier) | |

| Formula 5A | |
|---|---|
| Ingredient | % (wt.) |
| Isododecane (and) Dimethicone Crosspolymer-3 | 95.468 |
| Physalis Angulata Extract | 1.000 |
| Arnica Montana Extract | 2.000 |
| Centella Asiatica Extract | 0.250 |
| Squalane | 1.000 |
| Growth Hormone Releasing Peptide-6 | 0.032 |
| 1,3 Propanediol | 0.250 |

| Formula 6A | |
|---|---|
| Ingredient | % (wt.) |
| Isododecane (and) Dimethicone Crosspolymer-3 | 92.718 |
| Panthenyl Triacetate/Naringenin | 2.000 |
| Arnica Montana Extract | 2.000 |
| Dunaliella Salina Extract | 1.00 |
| Squalane | 2.000 |
| Growth Hormone Releasing Peptide-6 | 0.032 |
| 1,3 Propanediol | 0.250 |

| Formula 7A | |
|---|---|
| Ingredient | % (wt.) |
| Cyclopentasiloxane, Polysilicone-11 | 92.718 |
| Panthenyl Triacetate/Naringenin | 2.000 |
| Arnica Montana Extract | 2.000 |
| Dunaliella Salina Extract | 1.00 |
| Squalane | 2.000 |
| Growth Hormone Releasing Peptide-6 | 0.032 |
| 1,3 Propanediol | 0.250 |

| Formula 8A | |
|---|---|
| Ingredient | % (wt.) |
| Isododecane (and) Dimethicone Crosspolymer-3 | 87.500 |
| Panthenyl Triacetate/Naringenin | 2.000 |
| Arnica Montana Extract | 2.000 |
| Dunaliella Salina Extract | 1.000 |
| Squalane | 2.000 |
| Carrier: | 5.500 |
| Pentaerythrityl tetraisostearate | |
| Caprylic/capric triglyceride | |
| Propylene carbonate | |
| Stearalkonium hectorite | |
| Palmitoyl hexapeptide-12* | |

*Present in formulation at 0.055 wt. %; present in carrier at 100 ppm.

| Formula 9A | |
|---|---|
| Ingredient | % (wt.) |
| Isododecane (and) Dimethicone Crosspolymer-3 | 87.500 |
| Panthenyl Triacetate/Naringenin | 2.000 |
| Arnica Montana Extract | 2.000 |
| Dunaliella Salina Extract | 1.000 |
| Squalane | 2.000 |
| Carrier: | 5.500 |
| Pentaerythrityl tetraisostearate | |
| Caprylic/capric triglyceride | |
| Propylene carbonate | |
| Stearalkonium hectorite | |
| Palmitoyl hexapeptide-12* | |

*Present in formulation at 0.055 wt. %; present in carrier at 100 ppm.

| Formula 10A | |
|---|---|
| Ingredient | % (wt.) |
| Cyclopentasiloxane, Dimethicone Crosspolymer | 84.500 |
| Heptyl Undecylenate | 5.000 |
| Panthenyl Triacetate/Naringenin | 2.000 |
| Arnica Montana Extract | 2.000 |
| Dunaliella Salina Extract | 1.000 |
| Carrier: | 5.500 |
| Pentaerythrityl tetraisostearate | |
| Caprylic/capric triglyceride | |
| Propylene carbonate | |
| Stearalkonium hectorite | |
| Palmitoyl hexapeptide-12* | |

*Present in formulation at 0.055 wt. %; present in carrier at 100 ppm.

| Formula 11A | |
|---|---|
| Ingredient | % (wt.) |
| Cyclopentasiloxane, Dimethicone Crosspolymer | 84.500 |
| Heptyl Undecylenate | 5.000 |
| Panthenyl Triacetate/Naringenin | 2.000 |
| Arnica Montana Extract | 2.000 |
| Dunaliella Salina Extract | 1.000 |
| Carrier: | 5.500 |
| Pentaerythrityl tetraisostearate | |
| Caprylic/capric triglyceride | |
| Propylene carbonate | |
| Stearalkonium hectorite | |
| Palmitoyl hexapeptide-12* | |

*Present in formulation at 0.055 wt. %; present in carrier at 100 ppm.

| Formula 12A | |
|---|---|
| Ingredient | % (wt.) |
| Cyclopentasiloxane, Dimethicone Crosspolymer | 83.500 |
| Heptyl Undecylenate | 3.000 |
| Panthenyl Triacetate/Naringenin | 2.000 |
| Arnica Montana Extract | 2.000 |
| Dunaliella Salina Extract | 1.000 |
| Squalane | 2.000 |
| Carrier: | 5.500 |
| Pentaerythrityl tetraisostearate | |
| Caprylic/capric triglyceride | |
| Propylene carbonate | |
| Stearalkonium hectorite | |
| Palmitoyl hexapeptide-12* | |
| Carrier: | 1.000 |
| Pentaerythrityl tetraisostearate | |
| Caprylic/capric triglyceride | |
| Propylene carbonate | |
| Disteardimonium hectorite | |
| Palmitoyl tripeptide-1** | |

*Present in formulation at 0.055 wt. %; present in carrier at 100 ppm.
**Present in formulation at 0.01 wt. %; present in carrier at 100 ppm.

| Formula 13A | |
|---|---|
| Ingredient | % (wt.) |
| Cyclopentasiloxane, Dimethicone Crosspolymer | 83.500 |
| Heptyl Undecylenate | 5.000 |
| Panthenyl Triacetate/Naringenin | 2.000 |
| Arnica Montana Extract | 2.000 |
| Dunaliella Salina Extract | 1.000 |
| Carrier: | 5.500 |
| Pentaerythrityl tetraisostearate | |
| Caprylic/capric triglyceride | |
| Propylene carbonate | |
| Stearalkonium hectorite | |
| Palmitoyl hexapeptide-12* | |
| Carrier: | 1.000 |
| Pentaerythrityl tetraisostearate | |
| Caprylic/capric triglyceride | |
| Propylene carbonate | |
| Disteardimonium hectorite | |
| Palmitoyl tripeptide-1** | |

*Present in formulation at 0.055 wt. %; present in carrier at 100 ppm.
**Present in formulation at 0.01 wt. %; present in carrier at 100 ppm.

| Formula 14A | |
|---|---|
| Ingredient | % (wt.) |
| Cyclopentasiloxane, Dimethicone Crosspolymer | 83.500 |
| Heptyl Undecylenate | 5.000 |
| Panthenyl Triacetate/Naringenin | 2.000 |
| Arnica Montana Extract | 2.000 |
| Dunaliella Salina Extract | 1.000 |
| Carrier: | 5.500 |
| Pentaerythrityl tetraisostearate | |
| Caprylic/capric triglyceride | |
| Propylene carbonate | |
| Stearalkonium hectorite | |
| Palmitoyl hexapeptide-12* | |
| Carrier: | 1.000 |
| Pentaerythrityl tetraisostearate | |
| Caprylic/capric triglyceride | |
| Propylene carbonate | |
| Disteardimonium hectorite | |
| Palmitoyl tripeptide-1** | |

*Present in formulation at 0.055 wt. %; present in carrier at 100 ppm.
**Present in formulation at 0.01 wt. %; present in carrier at 100 ppm.

| Formula 15A | |
|---|---|
| Ingredient | % (wt.) |
| Cyclopentasiloxane, Dimethicone Crosspolymer | 83.400 |
| Heptyl Undecylenate | 2.500 |
| Panthenyl Triacetate/Naringenin | 2.000 |
| Arnica Montana Extract | 2.000 |
| Dunaliella Salina Extract | 1.000 |
| Carrier: | 5.500 |
| Pentaerythrityl tetraisostearate | |
| Caprylic/capric triglyceride | |
| Propylene carbonate | |
| Stearalkonium hectorite | |
| Palmitoyl hexapeptide-12* | |
| Carrier | 3.000 |
| Pentaerythrityl tetraisostearate | |
| Caprylic/capric triglyceride | |
| Propylene carbonate | |
| Disteardimonium hectorite | |
| Palmitoyl tripeptide-1** | |
| Caprylyl methicone | 0.500 |
| Phospatidyl serine/lecithin | 0.050 |
| Oleuropein | 0.050 |

*Present in formulation at 0.055 wt. %; present in carrier at 100 ppm.
**Present in formulation at 0.03 wt. %; present in carrier at 100 ppm.

| Formula 16A | |
|---|---|
| Ingredient | % (wt.) |
| Cyclopentasiloxane, Dimethicone Crosspolymer | 85.900 |
| Heptyl Undecylenate | 2.500 |
| Panthenyl Triacetate/Naringenin | 2.000 |
| Arnica Montana Extract | 2.000 |
| Dunaliella Salina Extract | 1.000 |
| Carrier: | 3.000 |
| Pentaerythrityl tetraisostearate | |
| Caprylic/capric triglyceride | |
| Propylene carbonate | |
| Stearalkonium hectorite | |
| Palmitoyl hexapeptide-12 | |
| Carrier: | 3.000 |
| Pentaerythrityl tetraisostearate | |
| Caprylic/capric triglyceride | |
| Propylene carbonate | |
| Disteardimonium hectorite | |
| Palmitoyl tripeptide-1 | |
| Caprylyl methicone | 0.500 |
| Phospatidyl serine/lecithin | 0.050 |
| Oleuropein | 0.050 |

*Present in formulation at 0.03 wt. %; present in carrier at 100 ppm.
**Present in formulation at 0.03 wt. %; present in carrier at 100 ppm.

Example 1B

Peptide Formulations

A series of formulations were prepared to assess the impact of various components on viscosity and stability. As discussed above, phosphatidylserine and oleuropein are difficult to solubilize.

The starting formulation, Formula 1B had a viscosity of approximately 5200 cPs. Formula 2B had a viscosity of approximately 6100 cPs. Formula 3B had a viscosity of approximately 7000 cPs. Formulation 2B and Formulation 3B each employed a different base, with the cyclopentysiloxane providing a higher viscosity. The results of this comparative test demonstrated that cyclopentysiloxane was able to provide a more desirable level of viscosity in formulation than the isododecane, dimethicone crosspolymer-3.

Formula 4B had a viscosity of approximately 8000 cPs. Formula 5B, which included cyclopentasiloxane as a base, exhibited a viscosity of approximately 9500 cPs. Formula 6B, using cyclopentasiloxane, dimethicone crosspolymer (DC9045) and heptyl undecylenate, exhibited a viscosity of approximately 28000 cPs. The results of this comparative test demonstrated that cyclopentysiloxane was able to provide a more desirable level of viscosity in formulation than the isododecane, dimethicone crosspolymer-3. The tests further demonstrated that the combination of cyclopentasiloxane, dimethicone crosspolymer and heptyl undecylenate exhibited acceptable levels of viscosity.

Formula 7B was similar to Formula 6B but also including palmitoyl tripeptide at 1%, exhibited a viscosity of approximately 16000 cPs—lower than that of Formula 6B, but still acceptably high. In Formula 8B, the amount of palmitoyl tripeptide was increased to 3%, and phosphatidylserine (lipoid PS P 70) was added, along with oleuropein 80% at 0.025%. It was found that Lipoid PS P70 and oleuropein exhibited poor solubility in heptyl undecylenate. In Formula 9B, the concentration of heptyl undecylenate was lowered to 2.5%, caprylyl methicone was added to solubilize the Lipoind PS P 70, which was increased to 0.05%, and oleuropein 80% was increased to 0.05%. The viscosity for Formula 9B was approximately 5000 cPs. The data demonstrated that caprylyl methicone was effective in solubilizing the phosphatidylserine and oleuropein; however, the greater stability was obtained at the expense of viscosity.

Tests were conducted to evaluate the feasibility of adding additional heptyl undecylenate to the formulations. In Formula 10B, the concentration of heptyl undecylenate was increased from 2.5% to 8.75%. Formula 10B exhibited separation and instability, and had a viscosity of approximately 1800 cPs. In Formula 11B, the concentration of heptyl undecylenate was increased from 8.75% to 16.75%. Formula 11B exhibited separation and instability, and had a viscosity of approximately 400 cPs. The results of these tests confirmed that raising levels of heptyl undecylenate resulted in instability of the formulations due to solubility issues with phosphatidylserine and oleuropein despite the presence of caprylyl methicone.

Other strategies were investigated for increasing viscosity while maintaining stability. In Formula 12B, the concentration of palmitoyl hexapeptide-12 containing base was lowered from 5.5% to 3% with a corresponding increase in the cyclopentasiloxane, dimethicone crosspolymer, yielding a formulation with a viscosity of approximately 24000 cPs. In Formula 13B, the concentration of palmitoyl hexapeptide-12 was lowered from 3% to 2% and heptyl undecylenate was removed to increase viscosity and stability, resulting in a formulation having a viscosity of approximately 47000 cPs. In Formula 14B, the concentration of palmitoyl hexapeptide-12 was increased back to 3% and the heptyl undecylenate was removed, yielding a formulation having an approximate viscosity of 34000 cPs. The results of the testing demonstrated that reducing the palmitoyl hexapeptide-12 containing base in favor of the cyclopentasiloxane, dimethicone crosspolymer increased viscosity to a desirable level even in the presence of heptyl undecylenate, resulting in a stable formulation.

A viscosity level of from 400 cPs to 50000 cPs is generally preferred for topical formulations, for example, 1000 cPs to 30000 cPs, or 10000 cPs to 25000 cPs, or 20000 cPs to 25000 cPs.

| Formula 1B | |
|---|---|
| Ingredient | % (wt.) |
| Isododecane, Dimethicone Crosspolymer-3 | 95.468 |
| Physalis Angulata Extract | 1.000 |
| Arnica Montana Extract | 2.000 |
| Centella Asiatica Extract | 0.250 |
| Squalane | 1.000 |
| Growth Hormone Releasing Peptide-2 | 0.032 |
| 1,3 Propanediol | 0.250 |

| Formula 2B | |
|---|---|
| Ingredient | % (wt.) |
| Isododecane, Dimethicone Crosspolymer-3 | 92.718 |
| Panthenyl Triacetate/Naringenin | 2.000 |
| Arnica Montana Extract | 2.000 |
| Dunaliella Salina Extract | 1.000 |
| Squalane | 2.000 |
| Growth Hormone Releasing Peptide-2 | 0.032 |
| 1,3 Propanediol | 0.250 |

| Formula 3B | |
|---|---|
| Ingredient | % (wt.) |
| Cyclopentasiloxane, Polysilicone-11 | 92.718 |
| Panthenyl Triacetate/Naringenin | 2.000 |
| Arnica Montana Extract | 2.000 |
| Dunaliella Salina Extract | 1.000 |
| Squalane | 2.000 |
| Growth Hormone Releasing Peptide-2 | 0.032 |
| 1,3 Propanediol | 0.250 |

| Formula 4B | |
|---|---|
| Ingredient | % (wt.) |
| Isododecane, Dimethicone Crosspolymer-3 | 87.500 |
| Panthenyl Triacetate/Naringenin | 2.000 |
| Arnica Montana Extract | 2.000 |
| Dunaliella Salina Extract | 1.000 |
| Squalane | 2.000 |
| Pentaerythrityl Tetraisostearate, Caprylic/Capric Triglyceride, Stearalkonium Hectorite, Propylene Carbonate, Palmitoyl Hexapeptide-12 | 5.500 |

| Formula 5B | |
|---|---|
| Ingredient | % (wt.) |
| Cyclopentasiloxane, Polysilicone-11 | 87.500 |
| Panthenyl Triacetate, Naringenin | 2.000 |
| Squalane, Dunaliella Salina Extract | 1.000 |
| Glycine Soja (Soybean) Oil, Arnica Montana Extract, Tocopherol | 2.000 |
| Squalane | 2.000 |
| Pentaerythrityl Tetraisostearate, Caprylic/Capric Triglyceride, Stearalkonium Hectorite, Propylene Carbonate, Palmitoyl Hexapeptide-12 | 5.500 |

Formula 6B

| Ingredient | % (wt.) |
| --- | --- |
| Cyclopentasiloxane, Dimethicone Crosspolymer | 84.500 |
| Heptyl Undecylenate | 5.000 |
| Panthenyl Triacetate, Naringenin | 2.000 |
| Squalane, Dunaliella Salina Extract | 1.000 |
| Glycine Soja (Soybean) Oil, Arnica Montana Extract, Tocopherol | 2.000 |
| Pentaerythrityl Tetraisostearate, Caprylic/Capric Triglyceride, Stearalkonium Hectorite, Propylene Carbonate, Palmitoyl Hexapeptide-12 | 5.500 |

Formula 7B

| Ingredient | % (wt.) |
| --- | --- |
| Cyclopentasiloxane, Dimethicone Crosspolymer | 83.500 |
| Heptyl Undecylenate | 5.000 |
| Panthenyl Triacetate, Naringenin | 2.000 |
| Squalane, Dunaliella Salina Extract | 1.000 |
| Glycine Soja (Soybean) Oil, Arnica Montana Extract, Tocopherol | 2.000 |
| Pentaerythrityl Tetraisostearate, Caprylic/Capric Triglyceride, Stearalkonium Hectorite, Propylene Carbonate, Palmitoyl Hexapeptide-12 | 5.500 |
| Pentaerythrityl Tetraisostearate, Caprylic/Capric Triglyceride, Disteardimonium Hectorite, Propylene Carbonate, Palmitoyl Tripeptide-1 | 1.000 |

Formula 8B

| Ingredient | % (wt.) |
| --- | --- |
| Cyclopentasiloxane, Dimethicone Crosspolymer | 81.450 |
| Squalane, Dunaliella Salina Extract | 1.000 |
| Glycine Soja (Soybean) Oil, Arnica Montana Extract, Tocopherol | 2.000 |
| Pentaerythrityl Tetraisostearate, Caprylic/Capric Triglyceride, Stearalkonium Hectorite, Propylene Carbonate, Palmitoyl Hexapeptide-12 | 5.500 |
| Pentaerythrityl Tetraisostearate, Caprylic/Capric Triglyceride, Stearalkonium Hectorite, Propylene Carbonate, Palmitoyl Tripeptide-1 | 3.000 |
| Heptyl Undecylenate | 5.000 |
| Phosphatidylserine, Phospholipids, Tocopherol, Ascorbyl Palmitate | 0.025 |
| Panthenyl Triacetate, Naringenin | 2.000 |
| Olea Europaea (Olive) Leaf Extract, Oleuropein | 0.025 |

Formula 9B

| Ingredient | % (wt.) |
| --- | --- |
| Cyclopentasiloxane, Dimethicone Crosspolymer | 83.40 |
| Heptyl Undecylenate | 2.500 |
| Squalane, Dunaliella Salina Extract | 1.000 |
| Glycine Soja (Soybean) Oil, Arnica Montana Extract, Tocopherol | 2.000 |
| Pentaerythrityl Tetraisostearate, Caprylic/Capric Triglyceride, Stearalkonium Hectorite, Propylene Carbonate, Palmitoyl Hexapeptide-12 | 5.500 |
| Pentaerythrityl Tetraisostearate, Caprylic/Capric Triglyceride, Stearalkonium Hectorite, Propylene Carbonate, Palmitoyl Tripeptide-1 | 3.000 |
| Caprylyl Methicone | 0.500 |
| Phosphatidylserine, Phospholipids, Tocopherol, Ascorbyl Palmitate | 0.050 |
| Panthenyl Triacetate, Naringenin | 2.000 |
| Olea Europaea (Olive) Leaf Extract, Oleuropein | 0.050 |

Formula 10B

| Ingredient | % (wt.) |
| --- | --- |
| Cyclopentasiloxane, Dimethicone Crosspolymer | 77.15 |
| Heptyl Undecylenate | 8.750 |
| Squalane, Dunaliella Salina Extract | 1.000 |
| Glycine Soja (Soybean) Oil, Arnica Montana Extract, Tocopherol | 2.000 |
| Pentaerythrityl Tetraisostearate, Caprylic/Capric Triglyceride, Stearalkonium Hectorite, Propylene Carbonate, Palmitoyl Hexapeptide-12 | 5.500 |
| Pentaerythrityl Tetraisostearate, Caprylic/Capric Triglyceride, Stearalkonium Hectorite, Propylene Carbonate, Palmitoyl Tripeptide-1 | 3.000 |
| Caprylyl Methicone | 0.500 |
| Phosphatidylserine, Phospholipids, Tocopherol, Ascorbyl Palmitate | 0.050 |
| Panthenyl Triacetate, Naringenin | 2.000 |
| Olea Europaea (Olive) Leaf Extract, Oleuropein | 0.050 |

Formula 11B

| Ingredient | % (wt.) |
| --- | --- |
| Cyclopentasiloxane, Dimethicone Crosspolymer | 69.150 |
| Heptyl Undecylenate | 16.750 |
| Squalane, Dunaliella Salina Extract | 1.000 |
| Glycine Soja (Soybean) Oil, Arnica Montana Extract, Tocopherol | 2.000 |
| Pentaerythrityl Tetraisostearate, Caprylic/Capric Triglyceride, Ste aralkonium Hectorite, Propylene Carbonate, Palmitoyl Hexapeptide-12 | 5.500 |
| Pentaerythrityl Tetraisostearate, Caprylic/Capric Triglyceride, Stearalkonium Hectorite, Propylene Carbonate, Palmitoyl Tripeptide-1 | 3.000 |
| Caprylyl Methicone | 0.500 |
| Phosphatidylserine, Phospholipids, Tocopherol, Ascorbyl Palmitate | 0.050 |
| Panthenyl Triacetate, Naringenin | 2.000 |
| Olea Europaea (Olive) Leaf Extract, Oleuropein | 0.050 |

Formula 12B

| Ingredient | % (wt.) |
| --- | --- |
| Cyclopentasiloxane, Dimethicone Crosspolymer | 85.900 |
| Heptyl Undecylenate | 2.500 |
| Squalane, Dunaliella Salina Extract | 1.000 |
| Glycine Soja (Soybean) Oil, Arnica Montana Extract, Tocopherol | 2.000 |
| Pentaerythrityl Tetraisostearate, Caprylic/Capric Triglyceride, Stearalkonium Hectorite, Propylene Carbonate, Palmitoyl Hexapeptide-12 | 3.000 |
| Pentaerythrityl Tetraisostearate, Caprylic/Capric Triglyceride, Stearalkonium Hectorite, Propylene Carbonate, Palmitoyl Tripeptide-1 | 3.000 |
| Caprylyl Methicone | 0.500 |
| Phosphatidylserine, Phospholipids, Tocopherol, Ascorbyl Palmitate | 0.050 |
| Panthenyl Triacetate, Naringenin | 2.000 |
| Olea Europaea (Olive) Leaf Extract, Oleuropein | 0.050 |

Formula 13B

| Ingredient | % (wt.) |
| --- | --- |
| Cyclopentasiloxane, Dimethicone Crosspolymer | 89.40 |
| Squalane, Dunaliella Salina Extract | 1.000 |
| Glycine Soja (Soybean) Oil, Arnica Montana Extract, Tocopherol | 2.000 |
| Pentaerythrityl Tetraisostearate, Caprylic/Capric Triglyceride, Stearalkonium Hectorite, Propylene Carbonate, Palmitoyl Hexapeptide-12 | 2.000 |
| Pentaerythrityl Tetraisostearate, Caprylic/Capric Triglyceride, Stearalkonium Hectorite, Propylene Carbonate, Palmitoyl Tripeptide-1 | 3.000 |
| Caprylyl Methicone | 0.500 |
| Phosphatidylserine, Phospholipids, Tocopherol, Ascorbyl Palmitate | 0.050 |
| Panthenyl Triacetate, Naringenin | 2.000 |
| Olea Europaea (Olive) Leaf Extract, Oleuropein | 0.050 |

Formula 14B

| Ingredient | % (wt.) |
| --- | --- |
| Cyclopentasiloxane, Dimethicone Crosspolymer | 88.70 |
| Squalane, Dunaliella Salina Extract | 1.000 |
| Glycine Soja (Soybean) Oil, Arnica Montana Extract, Tocopherol | 2.000 |
| Pentaerythrityl Tetraisostearate, Caprylic/Capric Triglyceride, Stearalkonium Hectorite, Propylene Carbonate, Palmitoyl Hexapeptide-12 | 3.000 |
| Pentaerythrityl Tetraisostearate, Caprylic/Capric Triglyceride, Stearalkonium Hectorite, Propylene Carbonate, Palmitoyl Tripeptide-1 | 3.000 |
| Caprylyl Methicone | 0.250 |
| Phosphatidylserine, Phospholipids, Tocopherol, Ascorbyl Palmitate | 0.025 |
| Panthenyl Triacetate, Naringenin | 2.000 |
| Olea Europaea (Olive) Leaf Extract, Oleuropein | 0.025 |

Example 1C

Exemplary formulations are prepared.

Exemplary Formula 1C

| Ingredient | % (wt.) |
| --- | --- |
| Cyclopentasiloxane, Dimethicone Crosspolymer | 82-92 |
| Palmitoyl hexapeptide-12 | 0.01-0.1 |
| Palmitoyl tripeptide-1 | 0.01-0.1 |
| Other Components | remainder |

Exemplary Formula 2C

| Ingredient | % (wt.) |
| --- | --- |
| Cyclopentasiloxane, Dimethicone Crosspolymer | 82-92 |
| Heptyl Undecylenate | 1-4 |
| Palmitoyl hexapeptide-12 | 0.01-0.1 |
| Palmitoyl tripeptide-1 | 0.01-0.1 |
| Other Components | remainder |

Exemplary Formula 3C

| Ingredient | % (wt.) |
| --- | --- |
| Cyclopentasiloxane, Dimethicone Crosspolymer | 82-92 |
| Palmitoyl hexapeptide-12 | 0.01-0.1 |
| Palmitoyl tripeptide-1 | 0.01-0.1 |
| Caprylyl methicone | 0.25-1 |
| Phosphatidyl serine | 0.05-0.1 |
| Oleuropein | 0.05-0.1 |
| Other Components | remainder |

Exemplary Formula 4C

| Ingredient | % (wt.) |
| --- | --- |
| Cyclopentasiloxane, Dimethicone Crosspolymer | 82-92 |
| Caprylyl methicone | 0.25-1 |
| Phosphatidyl serine | 0.05-0.1 |
| Oleuropein | 0.05-0.1 |
| Other Components | remainder |

Exemplary Formula 5C

| Ingredient | % (wt.) |
| --- | --- |
| Cyclopentasiloxane, Dimethicone Crosspolymer | 82-92 |
| Heptyl Undecylenate | 1-4 |
| Palmitoyl hexapeptide-12 | 0.01-0.1 |
| Palmitoyl tripeptide-1 | 0.01-0.1 |
| Caprylyl methicone | 0.25-1 |
| Phosphatidyl serine | 0.05-0.1 |
| Oleuropein | 0.05-0.1 |
| Other Components | remainder |

Exemplary Formula 6C

| Ingredient | % (wt.) |
| --- | --- |
| Cyclopentasiloxane, Dimethicone Crosspolymer | 82-92 |
| Heptyl Undecylenate | 1-4 |
| Carrier containing Palmitoyl hexapeptide-12 (@100 ppm) | 0.5-6 |
| Carrier containing Palmitoyl tripeptide-1 (@100 ppm) | 0.5-6 |
| Caprylyl methicone | 0.25-1 |
| Phosphatidyl serine | 0.05-0.1 |
| Oleuropein | 0.05-0.1 |
| Other Components | remainder |

Exemplary Formula 7C

| Ingredient | % (wt.) |
| --- | --- |
| Cyclopentasiloxane, Dimethicone Crosspolymer | 82-92 |
| Heptyl Undecylenate | 1-4 |
| Carrier: Pentaerythrityl tetraisostearate Caprylic/capric triglyceride Propylene carbonate Stearalkonium hectorite Palmitoyl hexapeptide-12** | 2-6 |

-continued

| Ingredient | % (wt.) |
|---|---|
| Carrier:<br>Pentaerythrityl tetraisostearate<br>Caprylic/capric triglyceride<br>Propylene carbonate<br>Disteardimonium hectorite<br>Palmitoyl tripeptide-1** | 1-6 |
| Caprylyl methicone | 0.25-1 |
| Phospatidyl serine/lecithin | 0.05-0.1 |
| Oleuropein | 0.05-0.1 |
| Other Components | remainder |

*Present in carrier at 100 ppm.
**Present in carrier at 100 ppm.

Exemplary Formula 8C

| Ingredient | % (wt.) |
|---|---|
| Cyclopentasiloxane, Dimethicone Crosspolymer | 82-92 |
| Heptyl Undecylenate | 1-4 |
| Carrier:<br>Pentaerythrityl tetraisostearate<br>Caprylic/capric triglyceride<br>Propylene carbonate<br>Stearalkonium hectorite<br>Palmitoyl hexapeptide-12* | 1-6 |
| Carrier:<br>Pentaerythrityl tetraisostearate<br>Caprylic/capric triglyceride<br>Propylene carbonate<br>Disteardimonium hectorite<br>Palmitoyl tripeptide-1** | 1-6 |
| Caprylyl methicone | 0.25-1 |
| Phospatidyl serine/lecithin | 0.05-0.1 |
| Oleuropein | 0.05-0.1 |
| Other Components | 3.5-14 |
| Panthenyl TriacetateNaringenin (or other anti-irritant) | 1-4 |
| Arnica Montana Extract (or other anti-inflammatory) | 1-4 |
| Dunaliella Salina Extract (or other antioxidant) | 0.5-2 |

*Present in carrier at 100 ppm.
**Present in carrier at 100 ppm.

Exemplary Formula 9C

| Ingredient | % (wt.) |
|---|---|
| Cyclopentasiloxane, Dimethicone Crosspolymer | 82-92 |
| Heptyl Undecylenate | 1-4 |
| Carrier containing Palmitoyl hexapeptide-12 (100 ppm) | 2-5 |
| Carrier containing Palmitoyl tripeptide-1 (100 ppm) | 2-5 |
| Caprylyl methicone | 0.25-1 |
| Phospatidyl serine/lecithin | 0.05-0.1 |
| Oleuropein | 0.05-0.1 |
| Other Components | 3.5-14 |

Exemplary Formula 10C

| Ingredient | % (wt.) |
|---|---|
| Cyclopentasiloxane, Dimethicone Crosspolymer | 82-92 |
| Heptyl Undecylenate | 1-4 |
| Carrier:<br>Pentaerythrityl tetraisostearate<br>Caprylic/capric triglyceride<br>Propylene carbonate<br>Stearalkonium hectorite<br>Palmitoyl hexapeptide-12* | 1-6 |
| Carrier:<br>Pentaerythrityl tetraisostearate<br>Caprylic/capric triglyceride<br>Propylene carbonate<br>Disteardimonium hectorite<br>Palmitoyl tripeptide-1** | 1-6 |
| Caprylyl methicone | 0.25-1 |
| Phospatidyl serine/lecithin | 0.05-0.1 |
| Oleuropein | 0.05-0.1 |
| Other Components | 3.5-14 |

Exemplary Formula 11C

| Ingredient | % (wt.) |
|---|---|
| Cyclopentasiloxane, Dimethicone Crosspolymer | 82-92 |
| Heptyl Undecylenate | 1-4 |
| Pentaerythrityl tetraisostearate<br>Caprylic/capric triglyceride<br>Propylene carbonate<br>Ste aralkonium hectorite<br>Palmitoyl hexapeptide-12 | 2-5 |
| Pentaerythrityl tetraisostearate<br>Caprylic/capric triglyceride<br>Propylene carbonate<br>Disteardimonium hectorite<br>Palmitoyl tripeptide-1 | 2-5 |
| Caprylyl methicone | 0.25-1 |
| Phospatidyl serine/lecithin | 0.05-0.1 |
| Oleuropein | 0.05-0.1 |
| Other Components | 3.5-14 |
| Anti-irritant | 1-4 |
| Anti-inflammatory | 1-4 |
| Anti-oxidant | 0.5-2 |

Example 2

Laser Wound Study

Figure 4A:
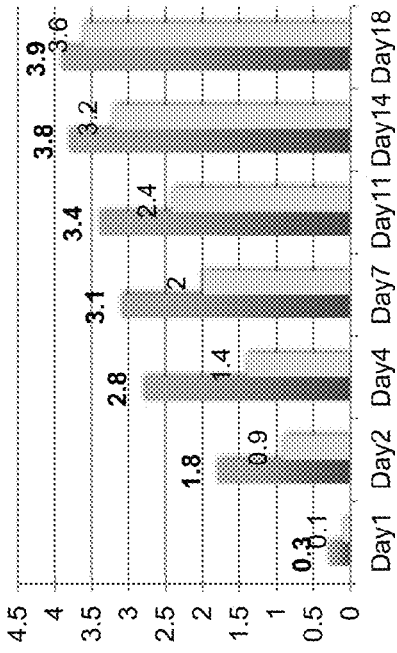
FIGS. 4A-4C depict the results of human subject wound healing progress for treatments using a dual peptide treatment versus a control treatment, the wound comprising a 3 mm erbium CO2 laser spot on his or her forearm.
Figure 4C:
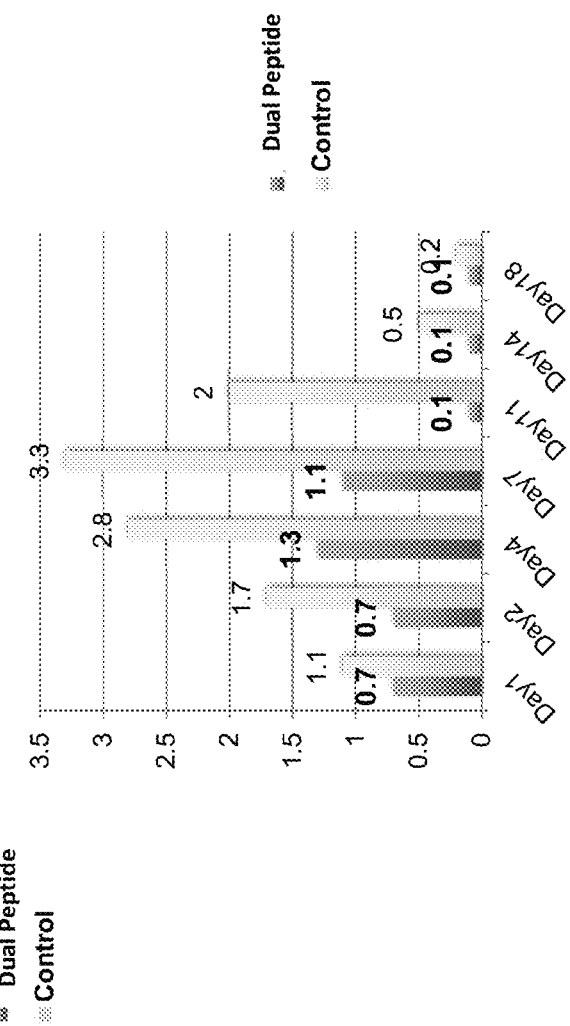
Figure 4B:
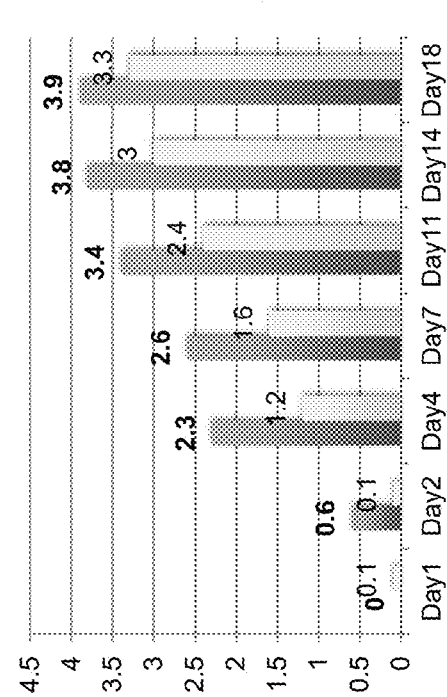

A laser wound study was conducted wherein subjects received a 3 mm erbium $CO_2$ laser spot on his or her forearm. Wound healing progress was observed for 18 days post-wound. Half of the subjects treated their wound at least one time a day for 18 days using a topical formulation (referred to herein as "a dual peptide") containing 1.0 wt. % GKH and 5.5 wt. % VGVAPG in an anhydrous silicone elastomer gel matrix. The other half of the subjects followed the same post-wound treatment protocol, but using a control formulation instead of a dual peptide formulation. The control was either Aquaphore® (comprising petrolatum, panthenol, glycerin, and bisabolol) from Beiersdorf Inc., Wilton, Conn., or no treatment). In FIG. 4A, a graph depicts the wound appearance for subjects receiving a dual peptide treatment versus control treatment over the course of 18 days post-wound. Wound appearance was superior for subjects receiving a dual peptide treatment, with significant differences on Days 2 to 14 when compared to the control. In FIG. 4B, the data demonstrates epithelial confluence was superior for subjects receiving a dual peptide treatment from Days 2 to 18, with noticeable differences between the two treatments on each of those days. The data depicted in FIG. 4C shows there was less crusting/scabbing in subjects receiving a dual peptide treatment from Days 1 to 18, with significant differences from Days 1 to 14.

Example 3

Laser Wound Study

Figure 5A:
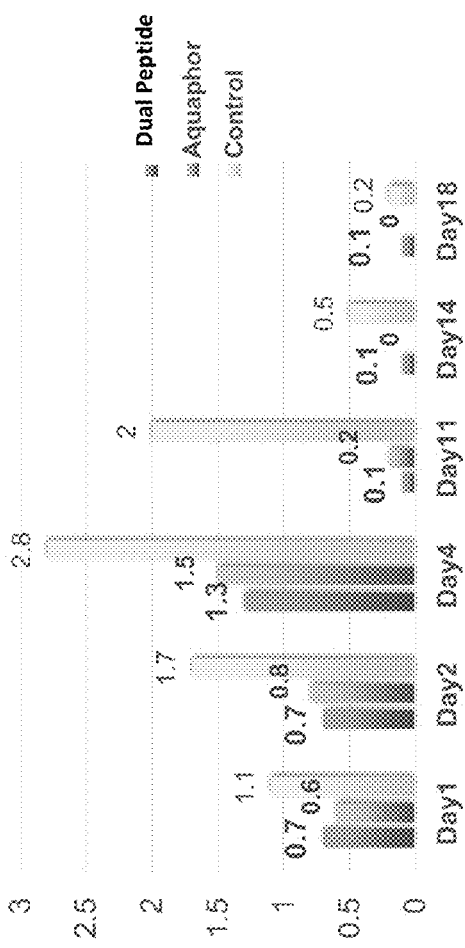
FIG. 5A provides crusting/scabbing data for a laser wound study comparing a dual peptide treatment against Aquaphor® treatment and a control treatment.
Figure 5D:
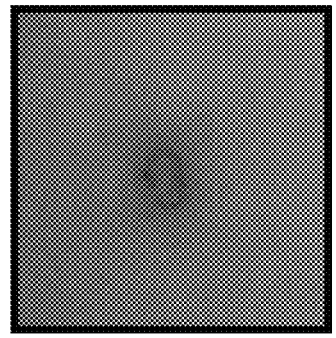
FIGS. 5B-5D are photographs of wound appearance on Day 4 for three different wounds, each treated with either a dual peptide (FIG. 5B), the Control treatment (FIG. 5C), or Aquaphor® (FIG. 5D).
Figure 5C:
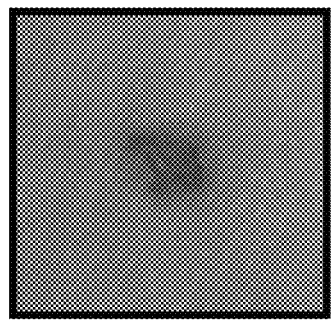
Figure 5B:
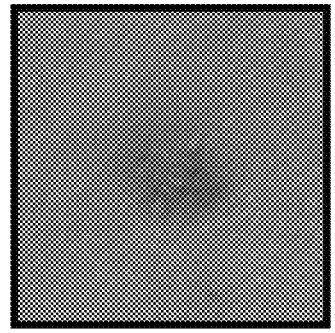

A study following the same protocol as Example 2 was conducted, which included testing of a commercial wound care treatment (Aquaphor®) in addition to a dual peptide and control. FIG. 5A provides crusting/scabbing data demonstrating that a dual peptide treatment was superior to the control from Days 1 to 18 and superior to Aquaphor® on Days 2 through 11. FIGS. 5B-D are photographs of wound appearance on Day 4 for three different wounds, each treated with either a dual peptide (FIG. 5B), the control treatment (FIG. 5C), or Aquaphor® (FIG. 5D). The photographs demonstrate that a dual peptide treatment exhibits the least amount of crusting or scabbing over the wound.

Example 4

Laser Wound Study

Figures 6A, 6B:
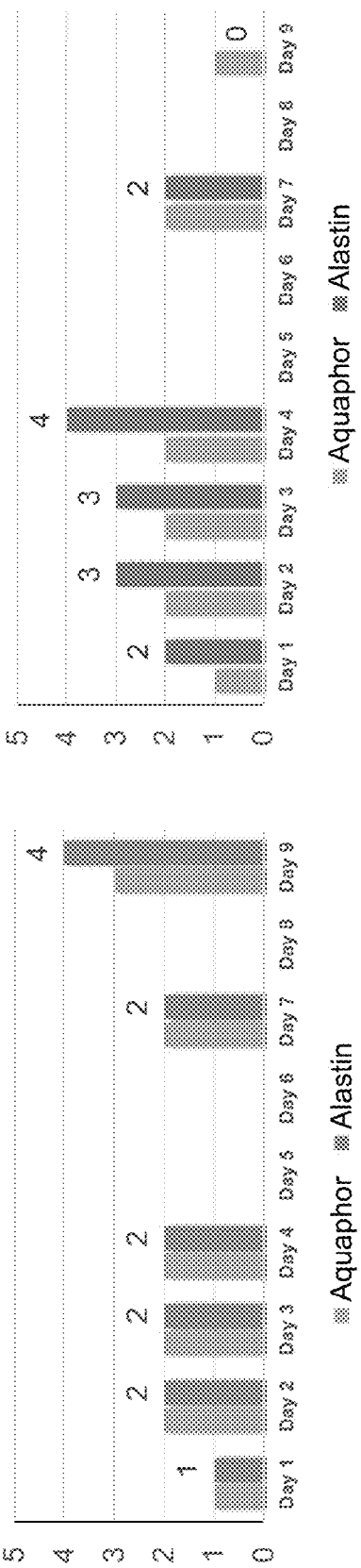
FIGS. 6A-6B provide data pertaining to wound appearance (FIG. 6A) and crusting/scabbing (FIG. 6B) in a study evaluating the wound healing benefits of two weeks of pretreatment with a dual peptide prior to a laser skin procedure and treatment with either a dual peptide or Aquaphor® post-procedure.
Figure 6D:
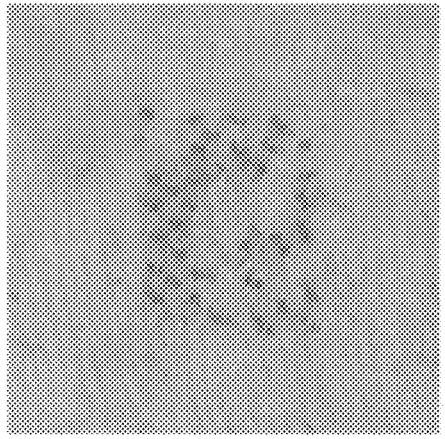
FIG. 6C is a Day 9 wound image for the Post-Wound dual peptide treatment and FIG. 6D is a Day 9 wound image for the Post-Wound Aquaphor® treatment.
Figure 6C:
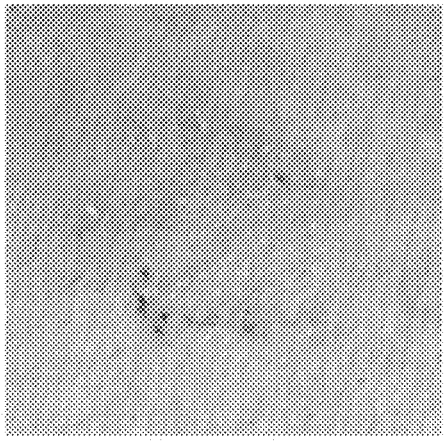

A laser wound study was conducted wherein subjects received a 1 mm erbium $CO_2$ laser spot on his or her forearm, the spot penetrating through the epidermis and deep into the dermis. The subjects received local anesthesia injections prior to receiving the laser wound. Each subject applied a dual peptide multiple times per day for two weeks (Pre-Wound Days 1-14) prior to receiving the laser wound. Half of the subjects received a dual peptide treatment at least one time per day for 9 days following receiving the laser wound, and the other half of the subject received Aquaphor® treatment multiple times per day for 9 days following receiving the laser wound. FIG. 6A-B provides data pertaining to wound appearance (FIG. 6A) and crusting/scabbing (FIG. 6B), demonstrating the wound healing benefits of two weeks of pretreatment with a dual peptide prior to a laser skin procedure and treatment with either a dual peptide or Aquaphor® post-procedure. In FIG. 6A, wound appearance data is provided for a dual peptide versus Aquaphor® treatment from Post-Wound Days 1 through Days 4, 7, and 9, with a meaningful difference on Post-Wound Day 9. In FIG. 6B, the differences in crusting and scabbing for a dual peptide treatment versus Aquaphor treatment is compared for Post-Wound Day 1 through Day 4, 7, and 9, with noticeable differences on Days 1 through 4. FIGS. 6C-D provide photographed wound images for the Post-Wound a dual peptide treatment (FIG. 6C) and Post-Wound Aquaphor® treatment (FIG. 6D) on Day 9, demonstrating superior wound healing associated with a dual peptide pre-treatment and post-treatment.

Example 5

Laser Esthetic Treatment Study

Figure 7C:
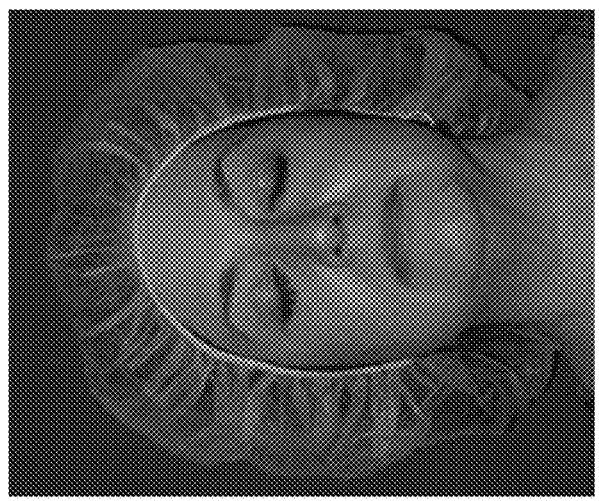
FIGS. 7A-7C are photographs of a patient before laser treatment, 4 days post laser treatment, and 9 days post laser treatment, wherein a dual peptide pretreatment and post treatment were utilized in connection with a laser treatment utilizing an Encore UltraPulse® ActiveFX™ $CO_2$ laser, manufactured by Lumenis, Inc., Santa Clara, Calif.
Figure 7B:
Figure 7A:

A human subject received a facial aesthetic laser treatment. The laser treatment utilized an Encore UltraPulse® ActiveFX™ $CO_2$ laser. The treatment protocol included a dual peptide pre-treatment for 21 days prior to a facial aesthetic laser treatment. Post-procedure, the patient was treated with a dual peptide on Days 1-14 ("invasive kit", as described herein) and from Day 14 onward ("noninvasive kit", as described herein). The photographs demonstrate images of the patient prior to treatment (FIG. 7A), Day 4 post-laser treatment (FIG. 7B), and Day 9 post-laser treatment (FIG. 7C). By Day 9 post-laser treatment (post-procedure), the patient's skin appears to have fully recovered from the procedure.

Example 6

Collagen and Elastin mRNA Study

Figure 8:
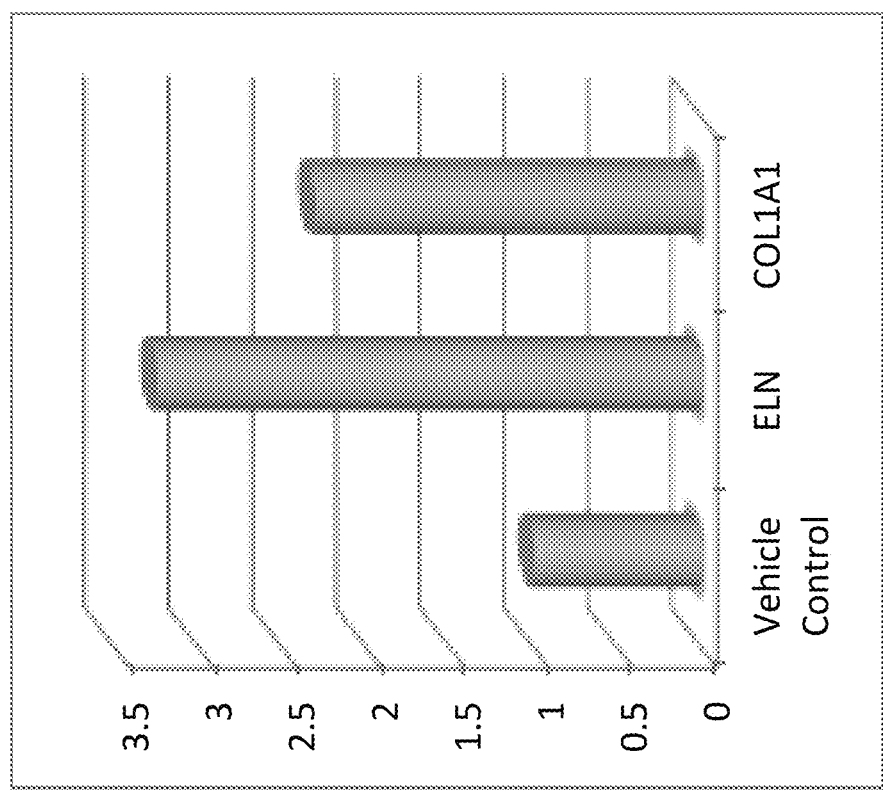
FIG. 8 depicts the results of a study comparing elastin mRNA for fibroblast monolayers exposed to either a dual peptide combination composition or a control.

Fibroblast monolayers were exposed to a dual peptide for 48 hours. mRNA production was compared to that of a set of fibroblast cells that were subjected to exposure to a control. After 48 hours, the fibroblast monolayers were harvested and mRNA was extracted from the cell lysate. Fibroblasts that were subjected to a dual peptide had elastin (ELN) mRNA levels more than three-fold greater than the control fibroblasts. The dual peptide also stimulated the fibroblasts to produce a more than two-fold increase in collagen (COL1A1) mRNA production compared to the control. FIG. 8 depicts the results of a study where fibroblast monolayers were exposed to a dual peptide composition. One set of fibroblasts were exposed to a dual peptide for 48 hours and a second set received a control treatment for 48 hours. The cells were then harvested and mRNA extracted from the cell lysates. The level of elastin (ELN) mRNA was more than 3 times higher for the dual peptide treated cells than the control fibroblasts. Collagen (COL1A1) mRNA production was over twice as high as the control fibroblasts. The data demonstrate that a dual peptide significantly upregulates collagen and elastin mRNA.

Example 7

Preconditioning

The concept of pre-conditioning is akin to the wound bed preparation concept practiced in wound healing. Preconditioning can be described as skin bed preparation. In order to maximize the healing capacity of therapeutic agents in chronic wounds, the bed must be debrided and prepared, ensuring that concentrations of proteases and cytokines are leveled to avoid lysis and degradation of these therapeutic agents from within the wound bed or from the corrosive wound fluid produced by these chronic wounds. See, e.g., Widgerow AD. Chronic wound fluid—thinking outside the box. *Wound repair and regeneration: official publication of the Wound Healing Society [and] the European Tissue Repair Society* 2011; 19(3): 287-91.

In much the same way, chronic photoaged skin needs adequate preparation to ensure the therapeutic procedure is optimized in its regenerative capacity. However, the background milieu is different. Before regeneration can take place, modulation of the extra-cellular matrix (ECM) must occur. In the case of damaged skin, this normally involves combatting the excessive fragmentation and agglutination of ECM proteins, primarily collagen, elastin and some glycosaminoglycans, which have collected in disorganized bundles resistant to protease digestion. The result is dysfunctional cell to cell and cell to matrix cross-talk and inefficient ongoing repair. See, e.g., Fligiel S, Varani J, Datta S, Kang S, Fisher G, Voorhees J J. Collagen Degradation in Aged/Photodamaged Skin InVivo and After Exposure to Matrix Metalloproteinase-1 InVitro. *The Journal of investigative dermatology* 2003; 120: 842-8. The resurfacing procedure usually results in denaturation of collagen producing extra fragmentation and an increased load for the ECM.

The theory of pre-conditioning is based upon the premise that aiding the process of degradation of these ECM bundles aids in clearing the ECM thus improving cellular and matrix cross talk. This allows the regenerative phase of repair to occur earlier in the process thus encouraging more efficient healing.

Denatured collagen and elastin fragments present as gelatins and the major proteases involved in clearing these fragments are metalloproteinases (MMP) 2 and 9, the gelatinases. See, e.g., Simeon A, Monier F, Emonard H, et al. Expression and Activation of Matrix Metalloproteinases in Wounds: Modulation by the Tripeptide—Copper Complex Glycyl-L-Histidyl-L-Lysine-Cu2F. *The Journal of investigative dermatology* 1999; 112: 957-62. A balance of MMP function and activity is extremely important for normal wound healing—chronic wounds exhibit an over-abundance of MMP activity with destruction of much of the ECM including the matrikine fragments derived from collagen and elastin that stimulate regeneration. Thus, pre-conditioning is aimed at temporarily increasing levels of MMPs (2 and 9 in particular) in order to degrade ECM fragment bundles and then allowing the newly denatured collagen fragments to stimulate regeneration in a relatively cleared ECM.

Figure 9:
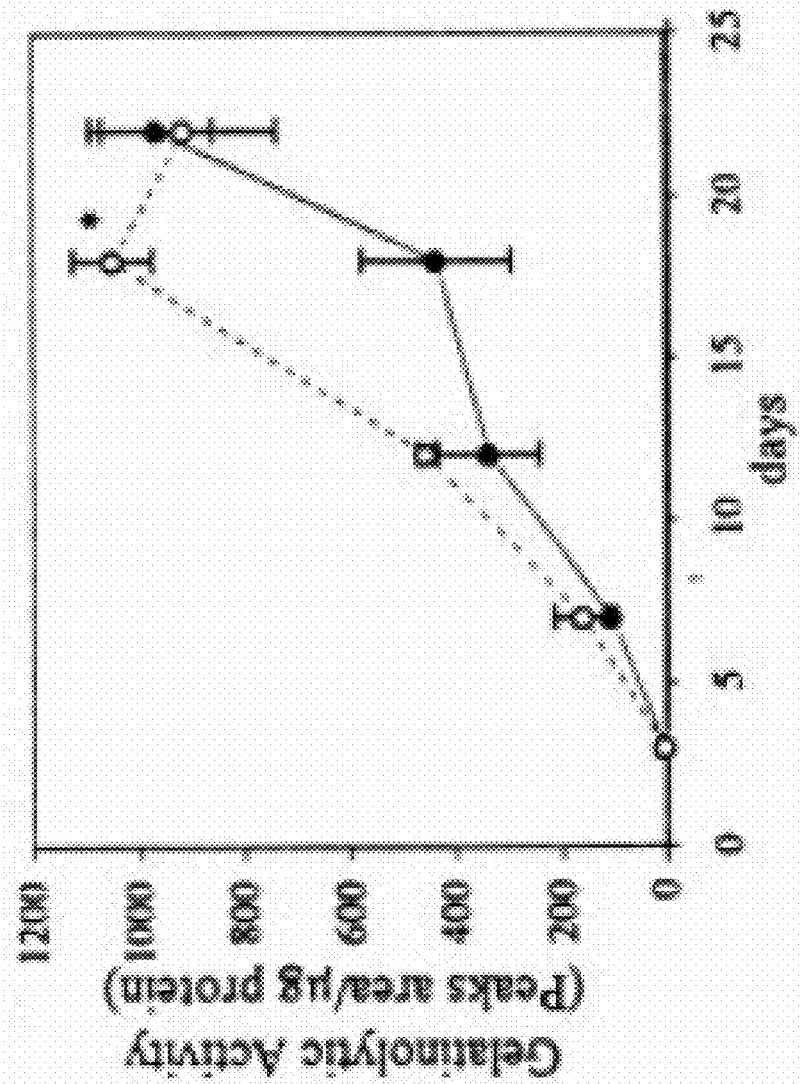
FIG. 9 is a graph showing gelatinolytic activity (peaks area/pg protein) over time for MMP-2.
Figure 10:
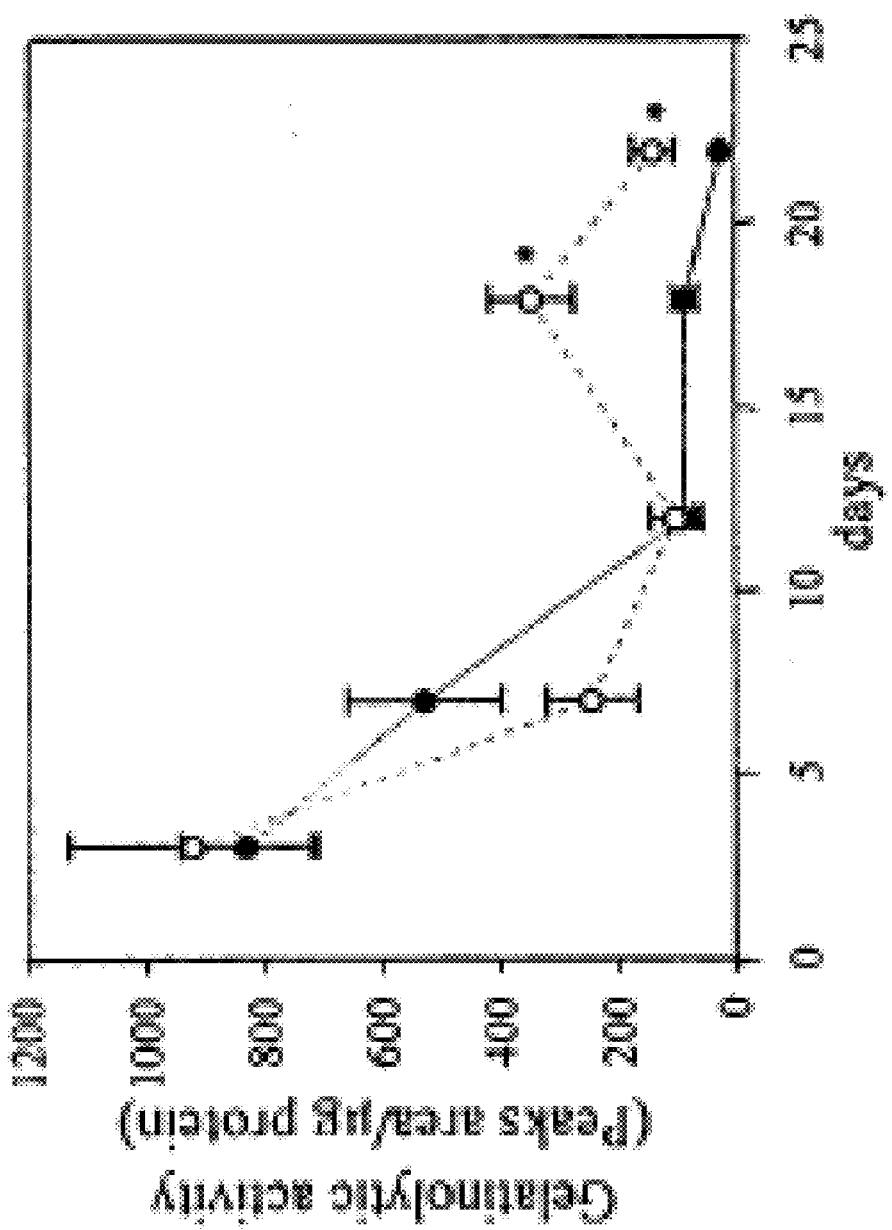
FIG. 10 shows a graph showing gelatinolytic activity (peaks area/μg protein) over time.

It is apparent that a balance of inflammation and protease activity is sought and the tri-hex technology introduces increased levels of MMPs 2 and 9 which are secreted at different times in the healing process. Studies have shown that GHK is able to modulate MMP expression and activation in wounds. MMP-2 was detected in wound models increasing from day 3 to day 22 after wound chamber implantation, whereas MMP 9 expression increase is short-lived coinciding with neutrophil infiltration, monocyte and macrophage activity and early phagocytosis. MMP2 then continues to clear the matrix over the next 3 weeks or so, clearing a pathway for angiogenesis and revascularization. FIG. 9 includes a graph showing gelatinolytic activity (peaks area/μg protein) over time for MMP-2. The dotted line is for GHK application to the wound chamber versus a control (solid line). GHK activates MMP-2 (gelatinase, Y axis) to far greater degree than control from day 3 and peaking at days 18-22. FIG. 10 includes a graph showing gelatinolytic activity (peaks area/pg protein) over time. The dotted line is for GHK application to the wound chamber versus a control (solid line). GHK activates MMP-2 (gelatinase, Y axis) to far greater degree than control from day 12 and peaking at days 18-22. See Simeon et al., *J Invest Dermatol* 112: 957-964, 1999.

Peptides, such as the tripeptides disclosed herein, stimulate increased levels of MMP-2, associated with extracellular matrix clearance before regeneration of collagen and elastin. There is also a direct correlation between MMP-2 and adipogenesis—the generation of new healthy fat. Adipogenesis is advantageous in that it can provide a volumizing effect for anti-aging, skin plumping and freshening effects. Adipose tissue (AT) expansion and regression are well-controlled processes in response to nutritional status. Expansion consists of hypertrophy, where existing adipocytes increase in volume, and hyperplasia, where newly formed adipocytes differentiate from precursor cells (adipogenesis). Tissue growth is also associated with angiogenesis and intensive proteolytic remodeling of the extracellular matrix (ECM). All of these processes are, in part, regulated by the matrix metalloproteinase (MMP) system. MMP deficiency has been observed to be associated with impaired AT development. Several studies show that the gelatinase subgroup (MMP-2 and MMP-9) is secreted by AT and that their activity is modulated during AT expansion/regression. Elevated plasma levels of MMP-2 are observed in obese patients, and these levels drop after bariatric surgery. Based on in vitro studies performed with rat, mouse (3T3-F442A and 3T3-L1 cell lines) and human preadipocytes, a role for the gelatinases has been suggested in differentiation of adipocytes.

The role of MMP-2 in in vitro preadipocyte differentiation, and in vivo de novo fat pad formation using precursor cells with genetic deficiency, gene silencing or overexpression of MMP-2 has been demonstrated. See Bauters et al., Biochimica et Biophysica Acta 1850 (2015) 1449-1456. Bauters et al. utilized an in vivo model of de novo adipogenesis wherein 3T3-F442A preadipocytes transduced with MMP-2 shRNA construct TRCN0000031228 or SHCOO2V negative control were injected subcutaneously in the back of 8 week-old male athymic BALB/cNude mice. Bauters et al. examined the size and density of adipocytes, as well as blood vessel density normalized to adipocyte number and observed the differentiation of embryonic fibroblasts into mature adipocytes. A significant increase in lipid accumulation during differentiation of 3T3-F442A cells with MMP-2 overexpression was observed, and was supported by significantly increased expression of aP2 and Ppar-γ. The de novo fat pads formed exhibited no differences in adipocyte size and density.

Differentiation of preadipocytes into new mature adipocytes can be divided in two main phases. The determination phase consists of commitment of progenitor cells to the adipocyte lineage. In the terminal differentiation phase, preadipocytes acquire the specific characteristics of mature adipocytes. By reducing the levels of MMP-2 via selective gene silencing, the differentiation of 3T3-F442A cells is reduced compared to control cells. MMP-2 overexpression had the opposed effect and stimulated differentiation of 3T3-F442A preadipocytes. However, even with minimally enhanced MMP-2 levels, enhanced differentiation was observed. Thus, MMP-2 appears to play a functional role in early and later stages of adipogenesis in vitro. Endothelial cells produce and secrete MMPs and it has been reported that in vivo adipogenesis is dependent on angiogenesis. Thus, local levels of active MMP-2 (independent of its origin) may be sufficient to account for its role in adipogenesis. Accordingly, by administering peptide, such as the tripeptides of the embodiments, to a patient, increased levels of MMP-2 can be obtained, which in turn can stimulate adipogenesis. The stimulated adipogenesis can yield a volumizing effect, resulting in the reduction in appearance of signs of aging, as well as plumping and freshening of the skin.

Figure 11:
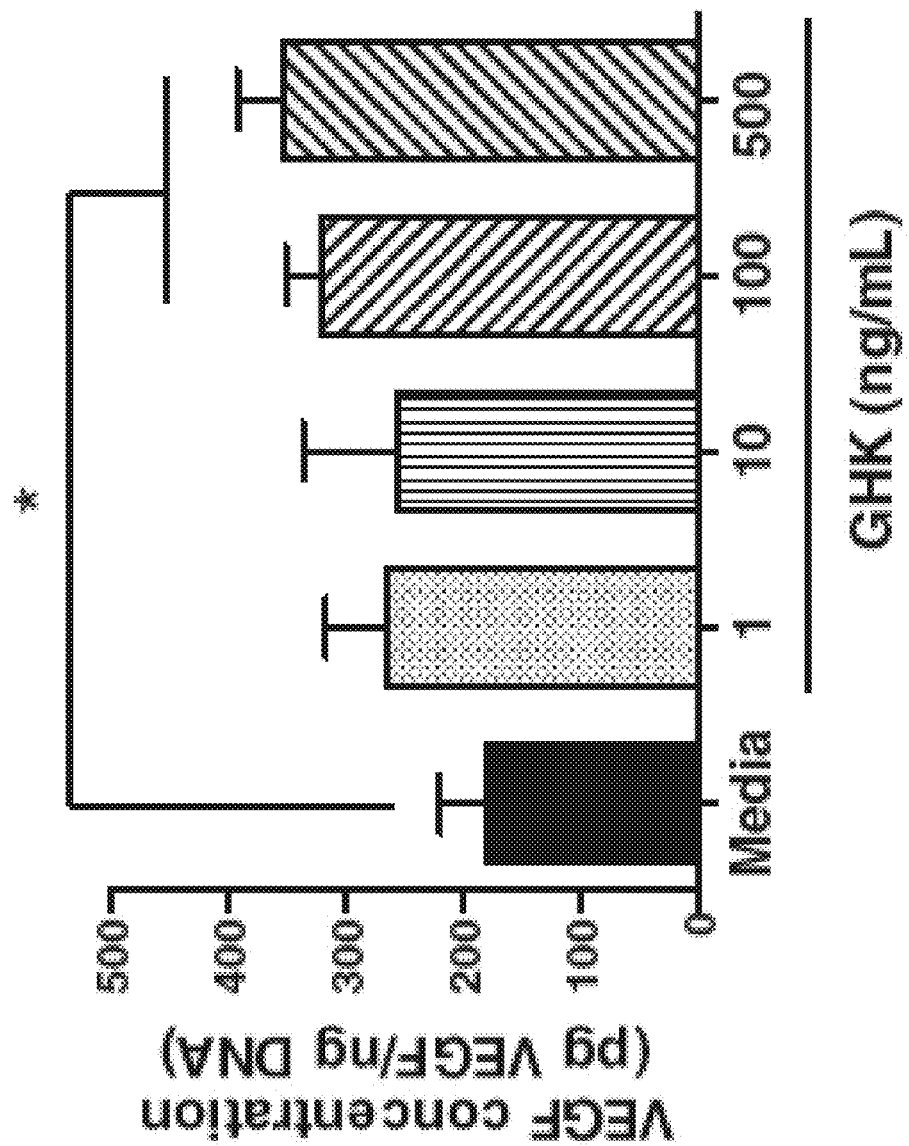
FIG. 11 shows VEGF concentration (pg VEGF/ng DNA) as a function of GHK (ng/mL) concentration.

The second area relating to ECM preparation involves the process of angiogenesis, the basis of nutrient delivery and exchange. The process is linked to the stimulation of VEGF and vessel development and growth takes weeks to develop. Pre-vascularization is expected to optimize wound healing. It has been demonstrated that the delivery modality for inducing angiogenesis must provide an extended (4 to 6 weeks) presence of the therapeutic agent at the site of desired vessel growth. See, e.g., Simons M. Angiogenesis: where do we stand now? *Circulation* 2005; 111(12): 1556-66. Such a prolonged presence cannot be achieved with single-dose administration of proteins or peptides but needs a protracted period of application. GHK dose-dependently increases the secretion of VEGF and stimulate tubular formation and neovascularization in animal models. FIG. 11 shows VEGF concentration (pg VEGF/ng DNA) as a function of GHK (ng/mL) concentration. See, e.g., Jose S, Hughbanks M L, Binder B Y, Ingavle G C, Leach J K.

Enhanced trophic factor secretion by mesenchymal stem/stromal cells with Glycine-Histidine-Lysine (GHK)-modified alginate hydrogels. *Acta biomaterialia* 2014; 10(5): 1955-64. Thus, a 4 week start to the process of administering a dual peptide prior to laser treatment ensures a robust start to angiogenic stimulation of the ECM.

Figure 12B:
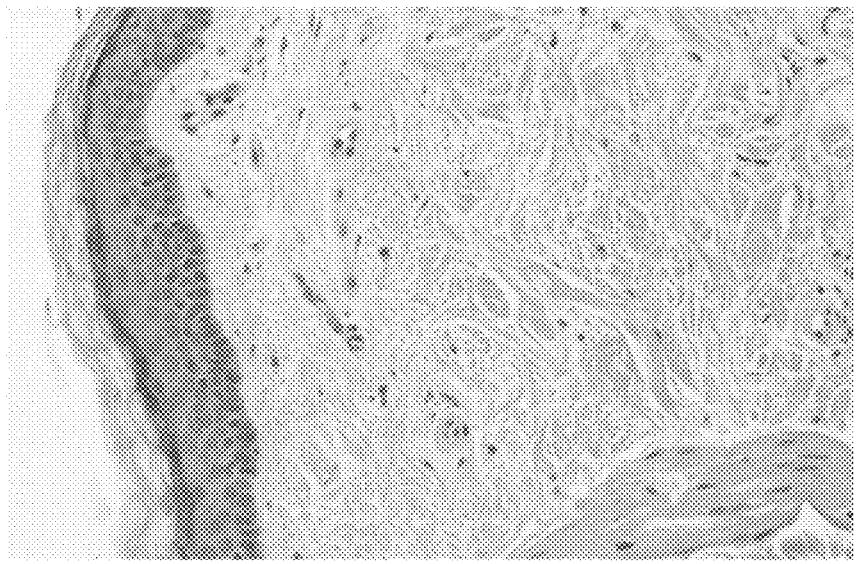
FIGS. 12A-12B provide photographs (100×) of skin biopsy samples for dual peptide treated skin (FIG. 12B) and an untreated control (FIG. 12A). The samples were stained with H/E, and the photographs demonstrate that preconditioning treatment with dual peptide results in a more organized distribution and arrangement of the collagen.
Figure 12A:
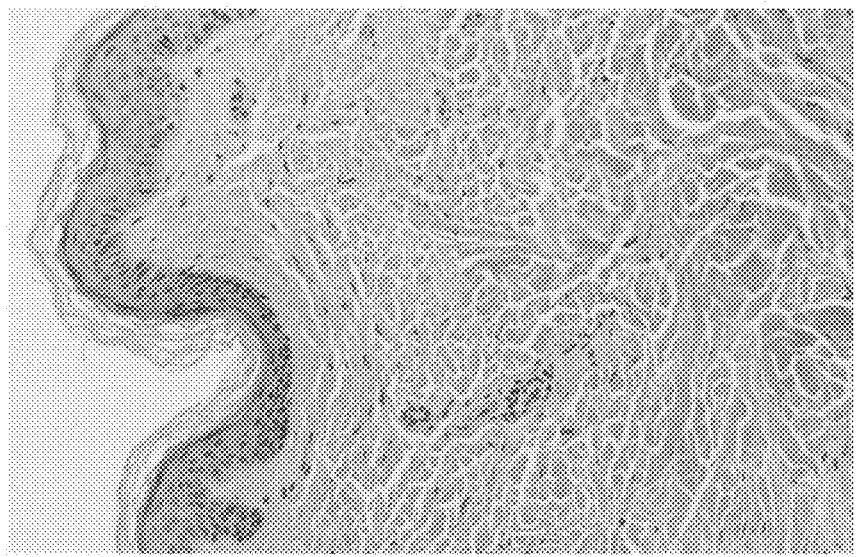

To assess the effect of pre-conditioning with dual peptides, a subject applied dual peptides to the fore arm for 2-3 weeks, and then a biopsy was taken from the treated fore arm as well as the another from the untreated (control) fore arm. The results are seen in FIGS. 12A and 12B. FIG. 12A shows the baseline, untreated sample biopsy stained with H/E. The baseline sample (FIG. 12A) shows irregularly clumped collagen in a disorganized extracellular matrix; the basal cells in the dermo-epidermal junction are flat displaying reduced functionality. After 2-3 weeks treatment with dual peptide, the biopsy (FIG. 12B) shows an extracellular matrix that has been cleared of a considerable amount of clumped collagen bundles and replaced with a more organized distribution and arrangement of the collagen; the basal stem cells at the dermo-epidermal junction are cuboidal in shape representing more functional activity and the epidermis is thicker with a healthier appearance.

Pre-conditioning is therefore a useful process for optimizing wound healing and esthetic outcomes on patients undergoing resurfacing procedures. This is based on the concept of wound bed preparation ensuring an early start to ECM remodeling. More particularly, early MMP-9 and later ongoing MMP-2 upregulation facilitates degradation of accumulated ECM protein bundles seen in elastotic photo-aged skin. In addition, stimulating angiogenesis on the basis of VEGF stimulation over a period of time improves ECM status in relation to future wound healing. A 2-3 week period is generally a minimum time satisfactory for pre-conditioning, but in certain circumstances a shorter preconditioning time can be employed. Accordingly, pre-conditioning for at least the two week period leading up to a procedure can advantageously be employed, e.g., pre-conditioning for two weeks, three weeks, four weeks or more, e.g., 2-4 weeks. Daily preconditioning is desirable, e.g., administration at least once a day, e.g., 2, 3, 4, or more times a day. Twice daily administration, e.g., morning and evening, can conveniently be employed. In certain embodiments, less than once per day application can be acceptable, e.g., every other day or every three days, or twice weekly.

Similar to pre-conditioning, post-treatment use can also be advantageously employed. A 2 week period is generally a minimum time satisfactory for post-treatment use, but in certain circumstances a shorter post-treatment use time can be employed. Accordingly, post-treatment use for at least the two week period following a procedure, once the skin is sufficiently healed such that the topical formulation can be applied, can be advantageously employed, e.g., post-treatment for two weeks, three weeks, four weeks or more, e.g., 2-4 weeks. Daily post-treatment administration is desirable, e.g., administration at least once a day, e.g., 2, 3, 4, or more times a day. Twice daily administration, e.g., morning and evening, can conveniently be employed. In certain embodiments, less than once per day application can be acceptable, e.g., every other day or every three days, or twice weekly.

In some instances, maintenance treatment of indefinite duration can be desirable to promote skin health, skin repair, and/or optimal skin bed condition. For maintenance, it may be acceptable to administer less frequently than once a day, e.g., once a week, or once every two or three days; however, twice daily administration, e.g., morning and evening, can conveniently be employed.

When the peptides are formulated in combination with other therapeutic agents, the formulation can be applied according to the preferred administration protocol for the other therapeutic agent(s). Alternatively, the administration protocol may be that as presented herein for compositions wherein the peptides are the only therapeutic agents present.

In various embodiments, various combinations of one or more of pre-conditioning, post-treatment application, and maintenance treatment can be employed.

Example 8

Elastin Production

Figure 13B:
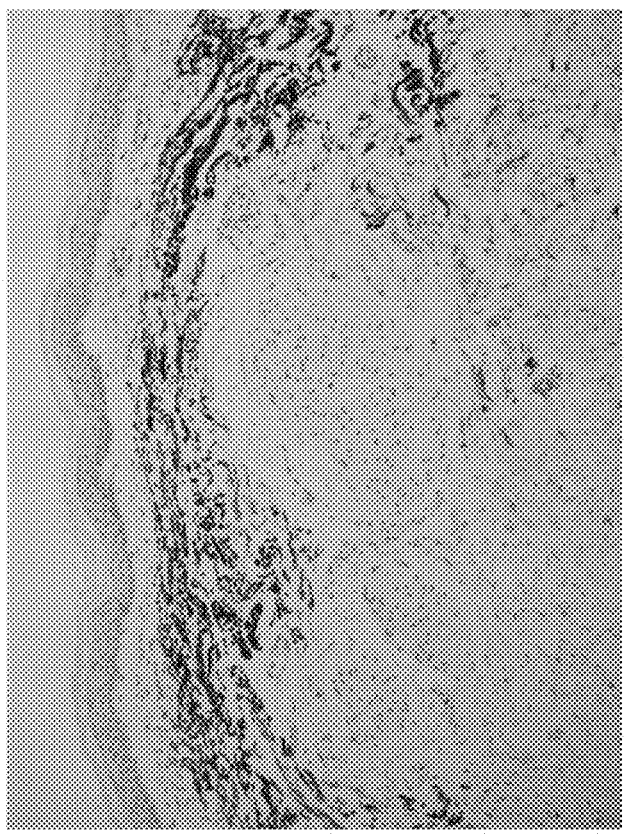
FIGS. 13A-13B provide photographs (100×) of skin biopsy samples for dual peptide treated skin (FIG. 13B) and an untreated control (FIG. 13A). The samples were stained to target elastin (brown), and the photographs demonstrate a significant increase in elastin protein levels associated with dual peptide treatment.
Figure 13A:
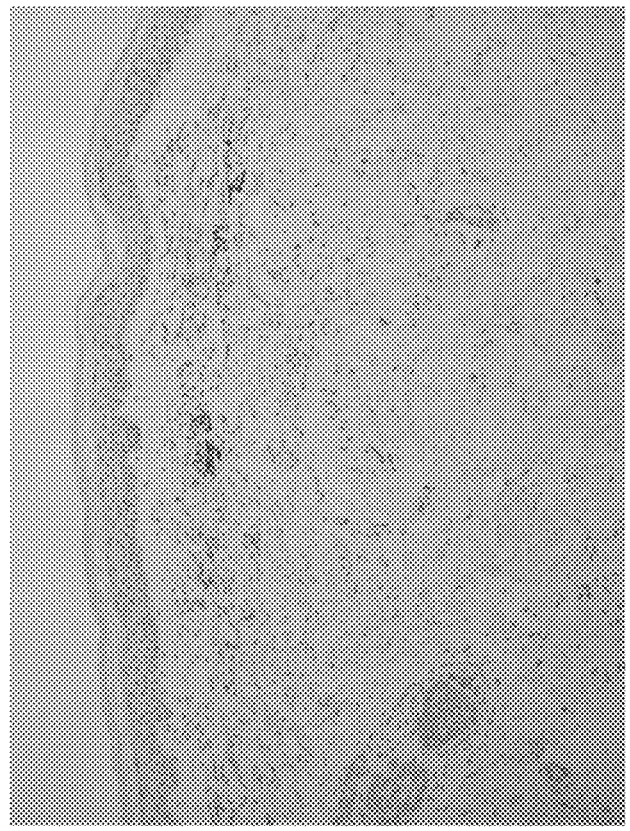

The impact of the dual peptide formulation on elastin production was investigated. A subject applied the dual peptide to a left forearm daily for 2-3 weeks and biopsies were obtained at of the conclusion of the daily treatment. Skin biopsy samples were taken from the treated portion of the left fore arm (dual peptide, FIG. 13B), and from an untreated portion of the right forearm (control, FIG. 13A). Using immune-histochemistry (IHC) techniques, the presence of elastin protein is seen as brown staining in the photographs at 20× and 100× magnification that were obtained. As the photographs show, a significant increase in elastin protein levels was observed for skin treated with the dual peptide formulation versus the control. A significantly lower level of elastin was observed in the untreated portion.

Example 9

Increased Pro-collagen Levels

Figure 14B:
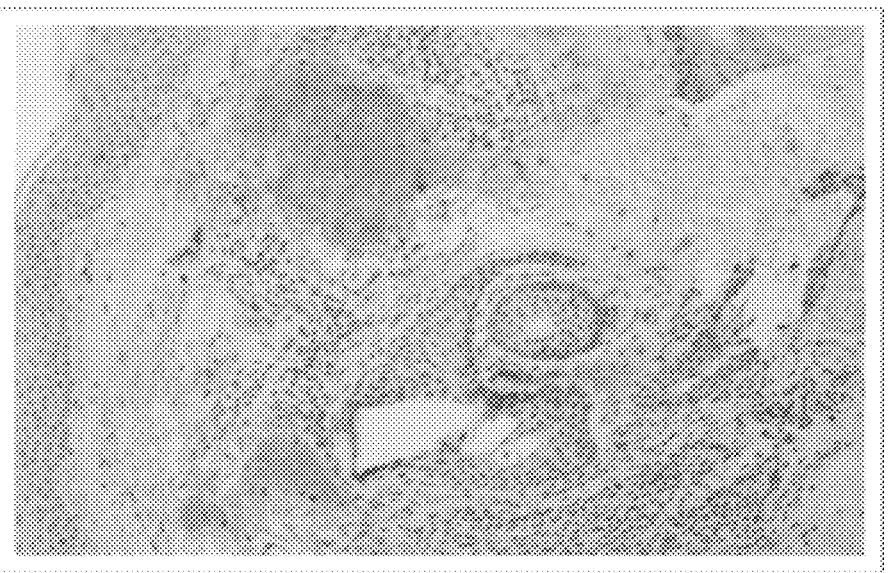
FIGS. 14A-14B provide photographs (100×) of skin biopsy samples for dual peptide treated skin (FIG. 14B) and an untreated control (FIG. 14A). The samples were stained to target pro-collagen by IHC, and the photographs demonstrate a significant increase in pro-collagen levels associated with dual peptide treatment.
Figure 14A:
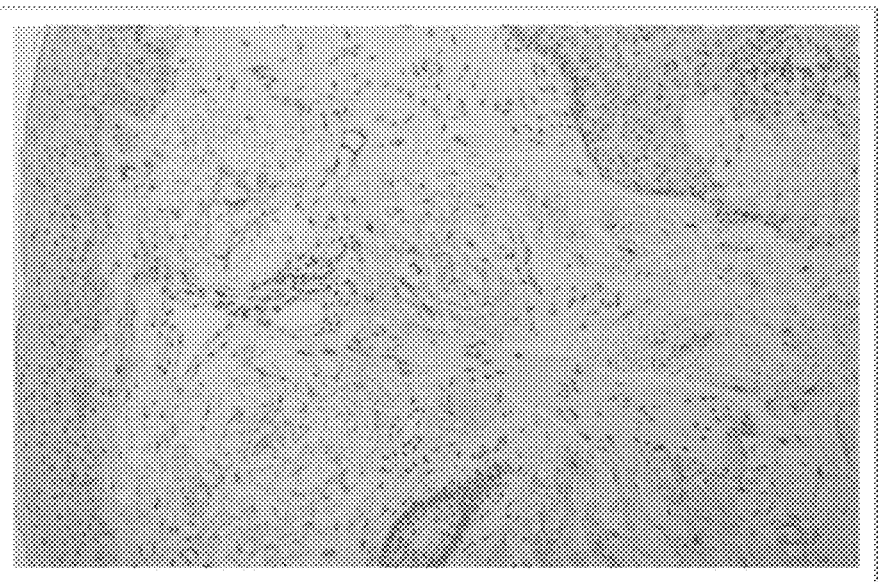

The impact on pro-collagen in dual peptide treated skin was investigated. Prior to the initiation of treatment with dual peptides, a baseline biopsy of the facial skin was obtained. The subject then applied the dual peptide to their face daily for 2 weeks and a second biopsy was obtained. FIG. 14A is a skin biopsy photograph (100×) showing low staining for pro-collagen by IHC as a baseline condition while FIG. 14B is a skin biopsy photograph (100×) showing significantly increased levels of pro-collagen after 2 weeks of dual peptide treatment.

Example 10

Increased Collagen

Figure 15B:
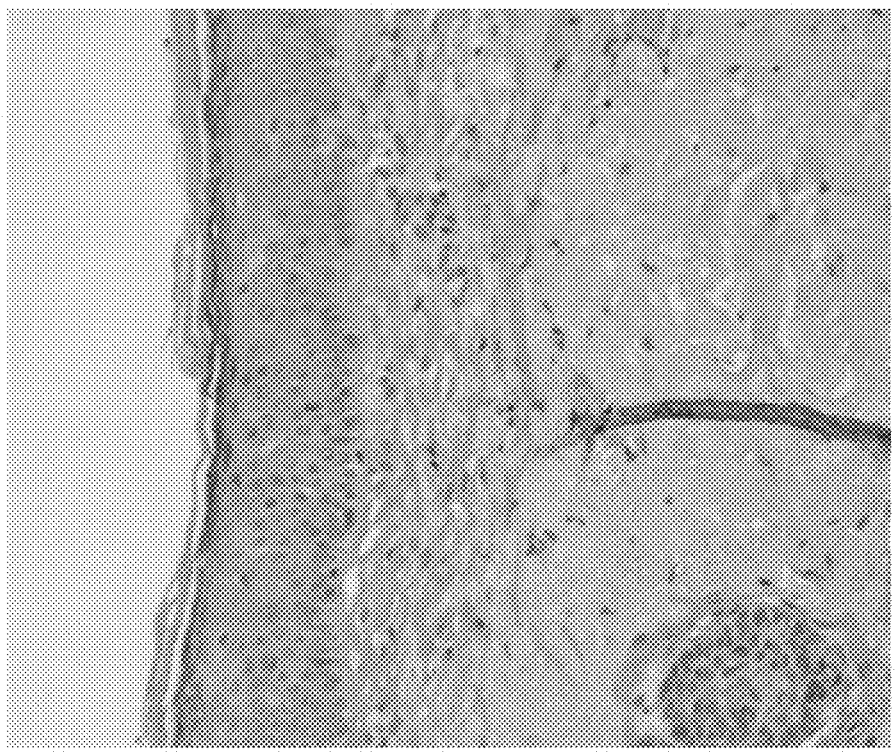
FIGS. 15A-15B provide photographs (100×) of skin biopsy samples for dual peptide treated skin three weeks after application (FIG. 15B) and a baseline sample (FIG. 15A). Upper dermal increased collagen formation over three weeks of topical application was observed, with solar elastosis pushed down by new collagen and improved epidermis appearance.
Figure 15A:
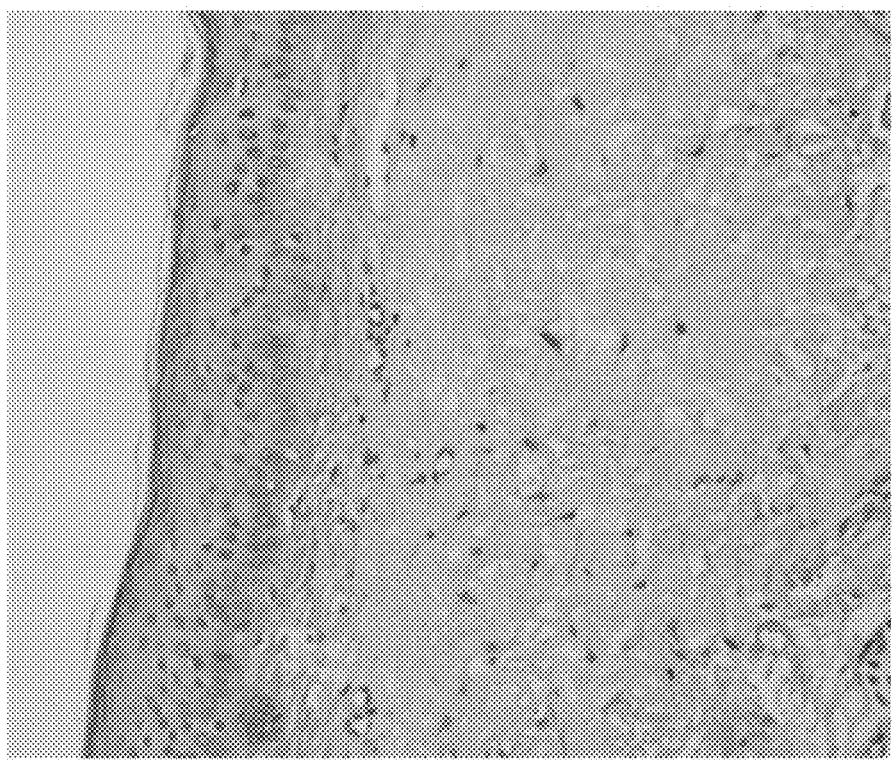

FIGS. 15A-B provide photographs (100×) of skin biopsy samples for dual peptide treated skin three weeks after application (FIG. 15B) and a baseline sample (FIG. 15A). Upper dermal increased collagen formation over three weeks of topical application was observed, with solar elastosis pushed down by new collagen and improved epidermis appearance.

Example 11

Distribution of Elastin

Figures 16A, 16B, 16C:
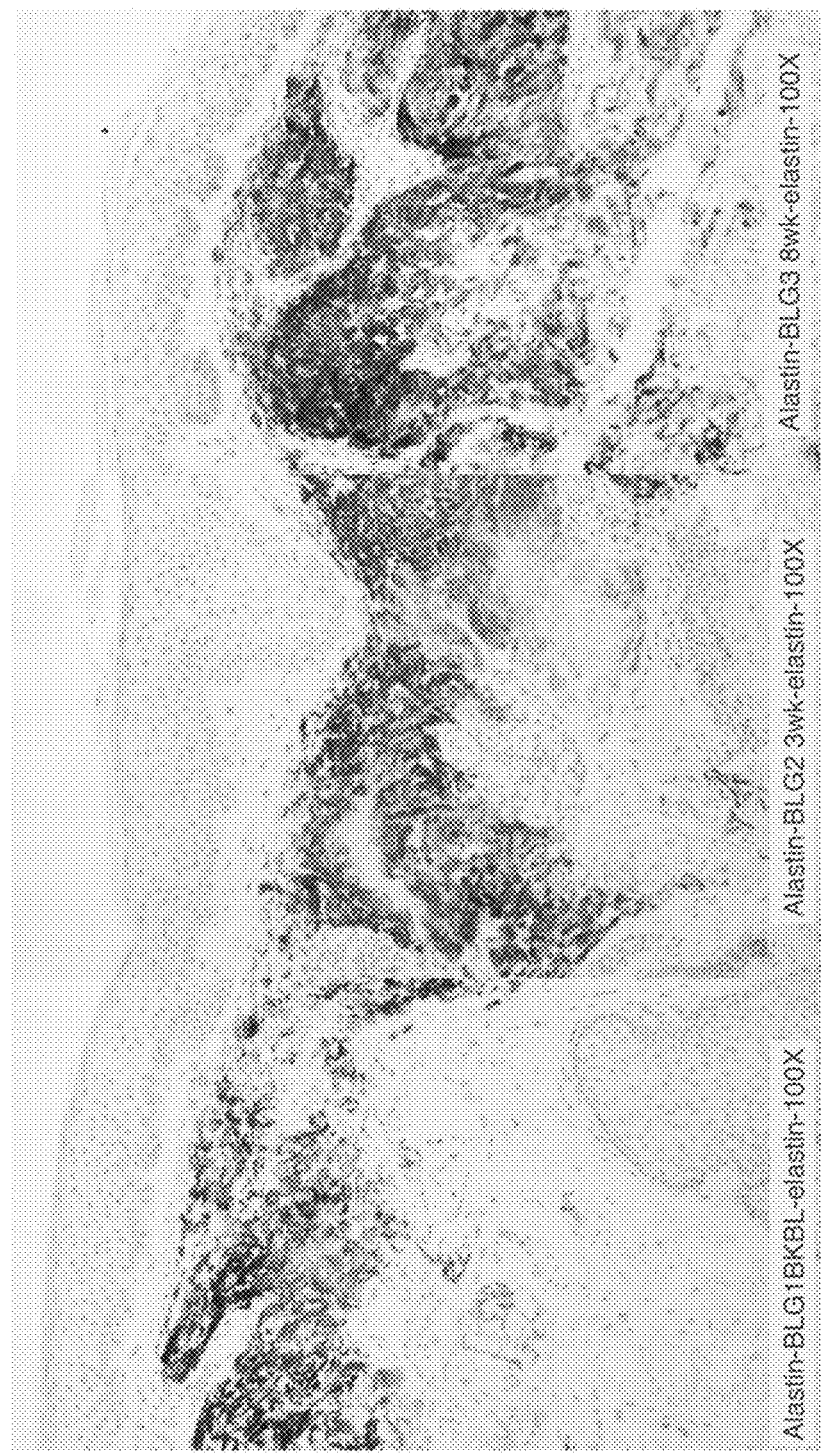
FIGS. 16A-16C provide photographs (100×) of skin biopsy samples for dual peptide treated facial skin three weeks after application (FIG. 16B), eight weeks after application (FIG. 16C) and a baseline sample (FIG. 16A). In clients who have elastin in elastotic photodamaged elastic tissue, topical application of the dual peptide results in the elastin material to be less clumped and markedly distributed into deeper dermal layers over the eight week period.

FIGS. 16A-C provide photographs (100×) of skin biopsy samples for dual peptide treated facial skin three weeks after application (FIG. 16B), eight weeks after application (FIG. 16C) and a baseline sample (FIG. 16A). In clients who have elastin in elastotic photodamaged elastic tissue, topical application of the dual peptide results in the elastin material to be less clumped and markedly distributed into deeper dermal layers over the eight week period.

Example 12

Decreased MMP 1

Figure 17A:
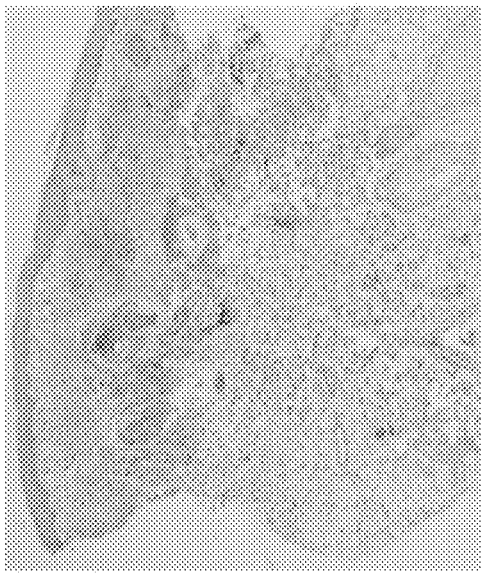
Figure 17B:
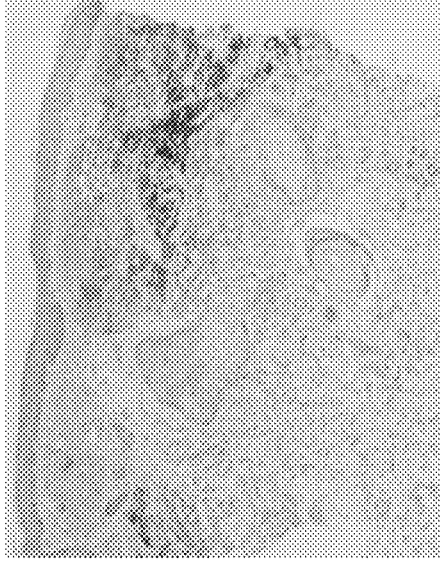

FIGS. 17A-D provide photographs of skin biopsy samples for dual peptide treated skin three weeks after application at 40× (FIG. 17B), a baseline sample at 40× (FIG. 8A), a skin biopsy sample for dual peptide treated skin three weeks after application at 100× (FIG. 17D) and a baseline sample at 100×(FIG. 17C). Decreased MMP1 staining was observed over the three week period in the pre-auricular region.

Example 13

Increased Decorin

Figure 18B:
FIGS. 18A-18B provide photographs (100×) of skin biopsy samples for dual peptide treated skin three weeks after application (FIG. 18B) and a baseline sample (FIG. 18A). Increased decorin staining was observed over the three week period in the pre-auricular region.
Figure 18A:

FIGS. 18A-B provide photographs (100×) of skin biopsy samples for dual peptide treated skin three weeks after application (FIG. 18B) and a baseline sample (FIG. 18A). Increased decorin staining was observed over the three week period in the pre-auricular region. Decorin is believed to influence fibrillogenesis, and also interacts with fibronectin, thrombospondin, the complement component Clq, epidermal growth factor receptor (EGFR) and transforming growth factor-beta (TGF-beta). Decorin has been shown to either enhance or inhibit the activity of TGF-beta 1. The primary function of decorin involves regulation during the cell cycle.

Example 14

Comparison of Dual Peptide Formulation to Standard of Care

To evaluate the efficacy in accelerating wound healing and subject satisfaction of Formulation 16A (composition provided above), it was compared to standard of care (SOC) following intense pulsed light (IPL) and/or pulsed dye laser (PDL) with Q-switch-alexandrite and fractionated $CO_2$ laser resurfacing compared to Vaniply regimen (Pharmaceutical Specialties, Inc., Rochester, Minn.). In addition, an analysis of adverse events was undertaken as the treatment formulations differed—a bland preservative free preparation (Vaniply) versus the other preparation containing active peptides and botanicals (Formulation 16A).

In this single-blind, randomized study, 15 female subjects aged 45-70 years with Fitzpatrick skin types I-III and moderate to severe photodamage underwent IPL and/or PDL with Q-switch-alexandrite and fractionated 10,600 nm $CO_2$ laser resurfacing of the face. Subjects were randomized on a 2:1 ratio to Formulation 16A or the standard of care (Vaniply ointment regimen). The subjects were pre-treated 3 weeks prior to resurfacing and continued for 8 weeks after the procedure. Subjects were evaluated on postoperative days 1, 3, 4, 7, 28, and 84. Endpoints included investigator— and subject-rated signs and symptoms of healing and subject-rated satisfaction questionnaire (p<0.05).

Assessment of healing in the first 2 week period post procedure was considered the most important end point. The overall analysis from investigator reporting was that skin healing and patient experience over the first 7 days (and all time points up to that time) post-resurfacing laser treatment was superior in the Formulation 16A group compared to expected healing outcomes. The Formulation 16A group showed better skin healing than the standard of care in all time intervals and by 7 days the group showed statistically significant advanced healing compared with SOC (P=0.015). In addition the blinded Investigator-rated healing rating and reported patient experience was higher in the Formulation 16A group than in the SOC group for all of the post-procedure timepoints, once again with statistical significance by day 7 (P=0.02). The turnaround time for healing and the day when differences between the groups began to manifest most obviously was day 3, when signs such as erythema (P=0.02) and exudation (P=0.01), and symptoms such as skin tenderness (P=0.02), burning and stinging (P=0.03) showed statistically significant differences between the 2 groups. As time progressed in the study, subjective assessment improved and by study end (day 84) significantly better results were obtained in the Formulation 16A group pertaining to the following 3 statements:

"Made me feel more confident in the way my skin looks" on Day 28 (P=0.08) and Day 84 (P=0.02)

"I would continue using this treatment regimen" on Day 28 (P=0.08) and Day 84 (P=0.03)

"I would recommend this treatment to others" on Day 28 (P=0.08) and Day 84 (P=0.03).

Formulation 16A appeared to produce improvements in the healing experience following IPL and/or PDL with Q-switch-alexandrite and fractionated $CO_2$ laser resurfacing of the face. The apparent reduction in healing time with Formula 16A allowed subjects to resume their normal activities of daily living sooner. In addition, subjects were more satisfied with Formula 16A than standard of care and without any report of adverse events.

Example 21

Comparison of Dual Peptide Formulation to Standard of Care

A study was conducted to evaluate the efficacy in accelerating wound healing and subject satisfaction of the Alastin Procedure Enhancement System ("Alastin", or Formula 16A) compared to standard of care following IPL and/or PDL with Q-switch-alexandrite and fractionated $CO_2$ laser resurfacing (Pharmaceutical Specialties, Inc., Rochester, Minn.) compared to Vaniply regimen (standard of care) particularly in the first week of treatment. The aim was to assess objectively if the Alastin group healed faster within the 7-day period, suffered any adverse events, experienced greater symptomatic relief over the same period and whether clients were able to enter the work force or society earlier than SOC group. In summary, the study was an assessment of downtime and patient experience following aggressive resurfacing procedures. Endpoints included investigator- and subject-rated signs and symptoms of healing and subject-rated comfort with procedure and satisfaction questionnaire.

In analyzing the results of the trial, in view of relatively small numbers the one sided Student-t test was used with statistical significance defined as ≤0.05.

Statistically Significant Differences

Figure 19A:
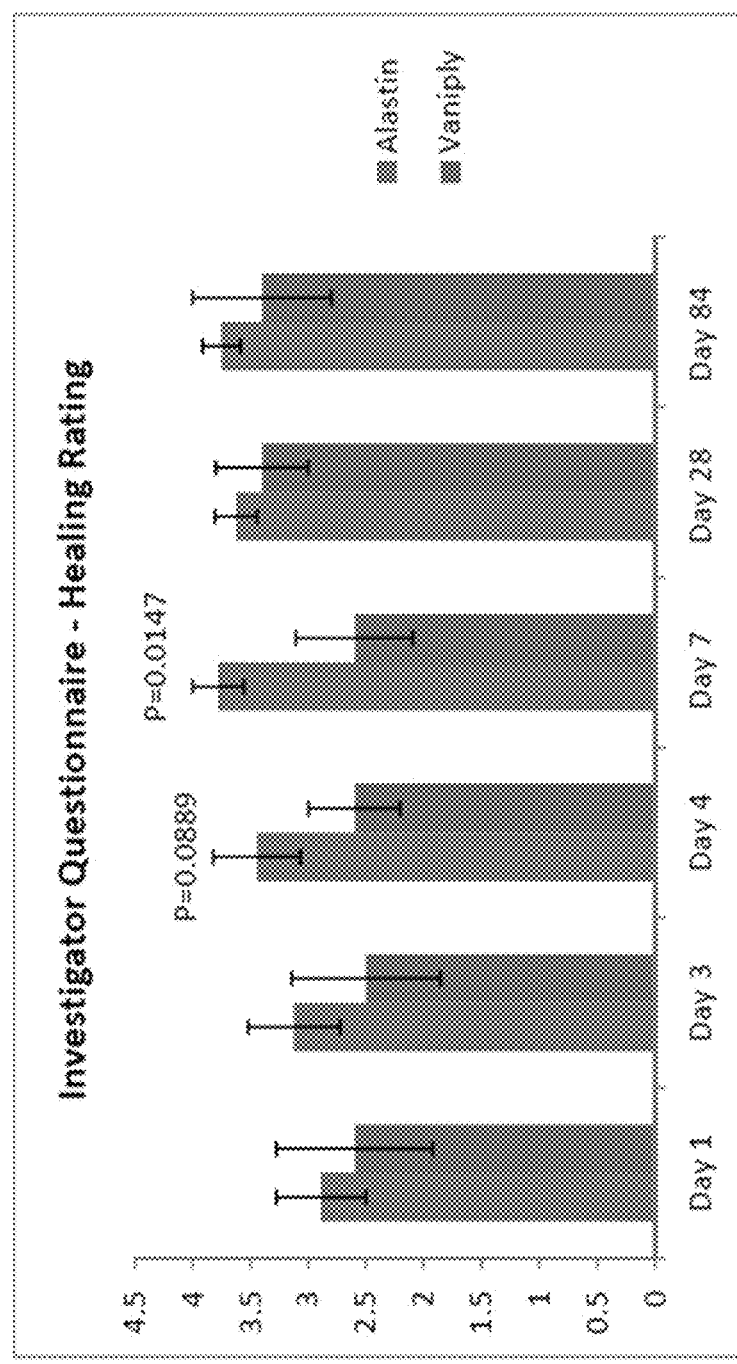
Figure 19B:
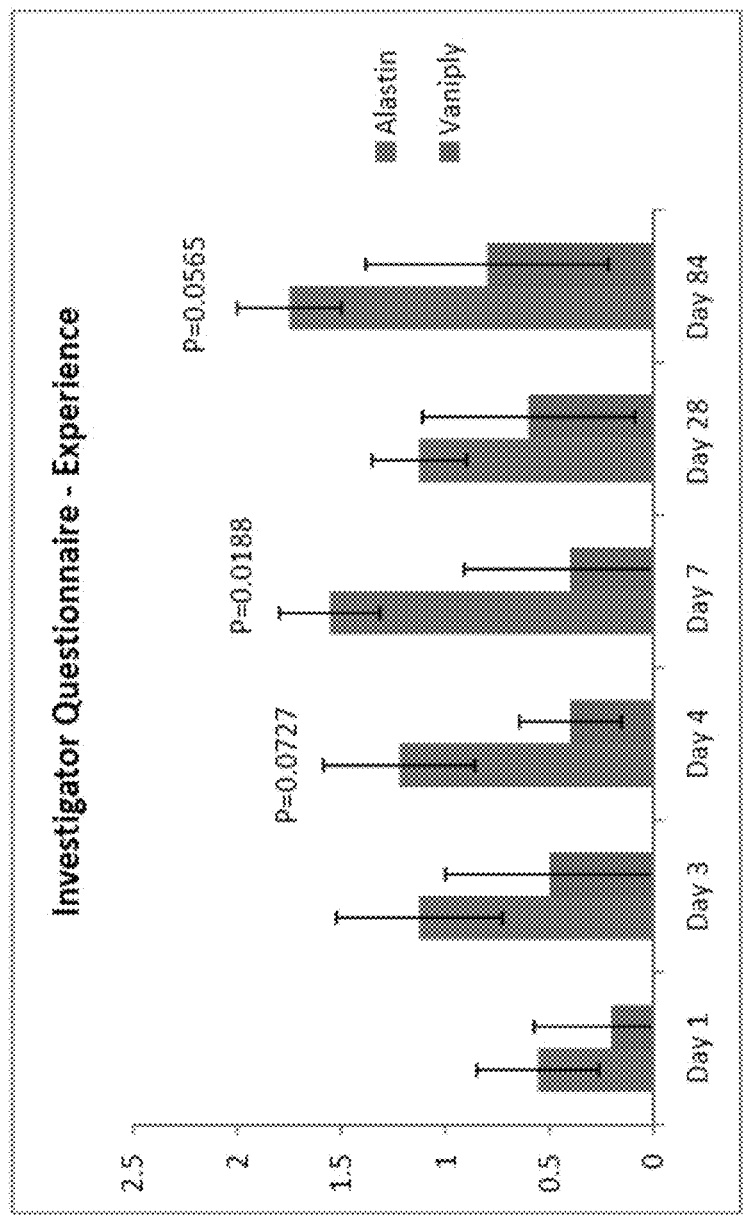

The overall analysis from investigator reporting was that skin healing and patient experience over the first 7 days (and all time points up to that time) post-resurfacing laser treatment was superior in the Alastin group compared to expected healing outcomes. The Alastin group showed better skin healing than the standard of care in all time intervals and by 7 days the group showed statistically significant advanced healing compared with SOC (P=0.015). In addition the blinded Investigator-rated healing rating and reported patient experience was higher in the Alastin group than in the SOC group for all of the post-procedure timepoints, once again with statistical significance by day 7 (P=0.02). The results of the Investigator Questionnaire including Healing Rating and Experience are presented in FIG. 19A and FIG. 19B, respectively.

Figure 19D:
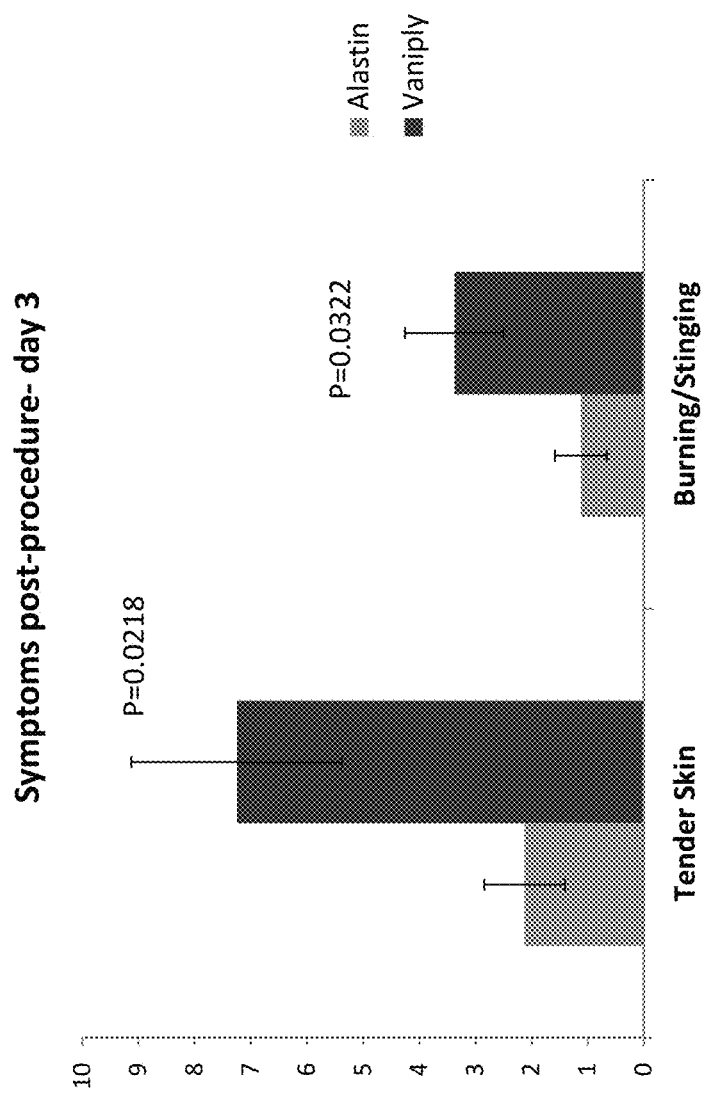
Figure 19E:
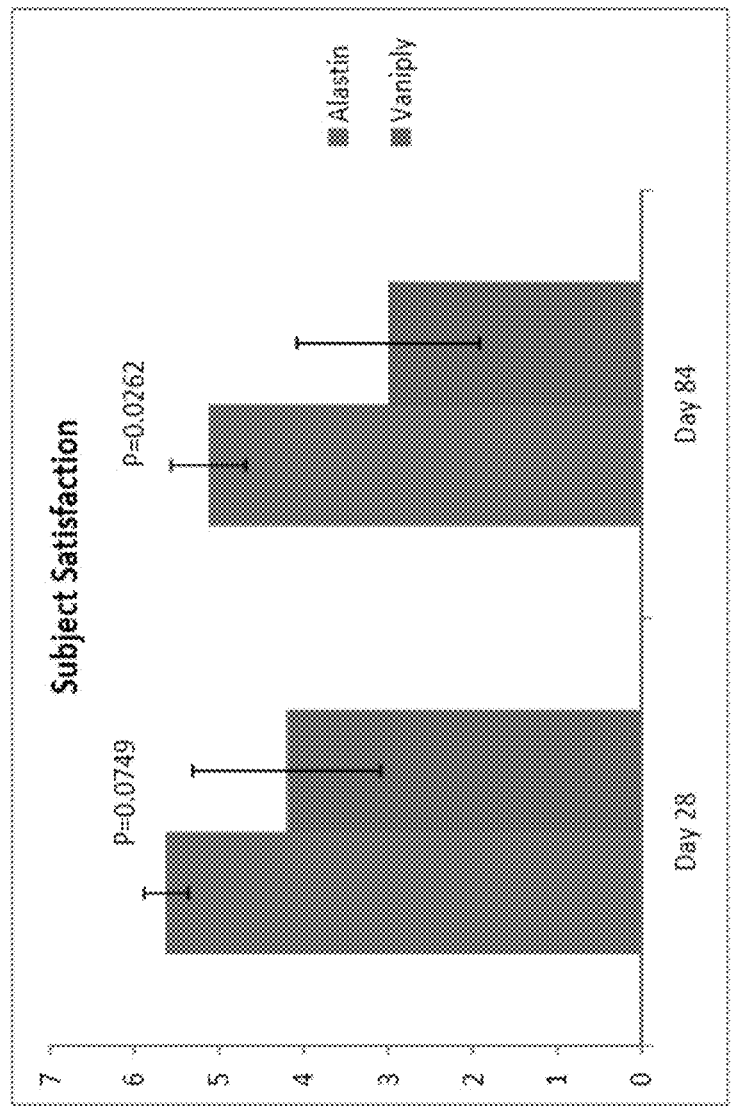

The turnaround time for healing and the day when differences between the groups began to manifest most obviously was day 3, when signs such as erythema (P=0.02) and exudation (P=0.01), and symptoms such as skin tenderness (P=0.02), burning and stinging (P=0.03) showed statistically significant differences between the two groups. The results of analysis of signs post procedure on day 3, symptoms post procedure on day 3, and subject satisfaction are presented in FIG. 19C, FIG. 19D, and FIG. 19E, respectively.

On subjective scoring, the Alastin group consistently demonstrated superior outcomes. The Alastin group showed statistically significant higher long term subject satisfaction than the SOC reaching significant levels by Day 84 (P=0, 03). For the Subject Global Aesthetic Improvement of long term Skin Quality, by the end of the study (day 84), the Alastin group had statistically significant better results than the SOC group for the following 3 statements:

"Made me feel more confident in the way my skin looks"—Day 84 (P=0.02) (Question 11)
"I would continue using this treatment regimen"—Day 84 (P=0.03) (Question 12)
"I would recommend this treatment to others"—Day 84 (P=0.03) (Question 13)

Figure 19F:
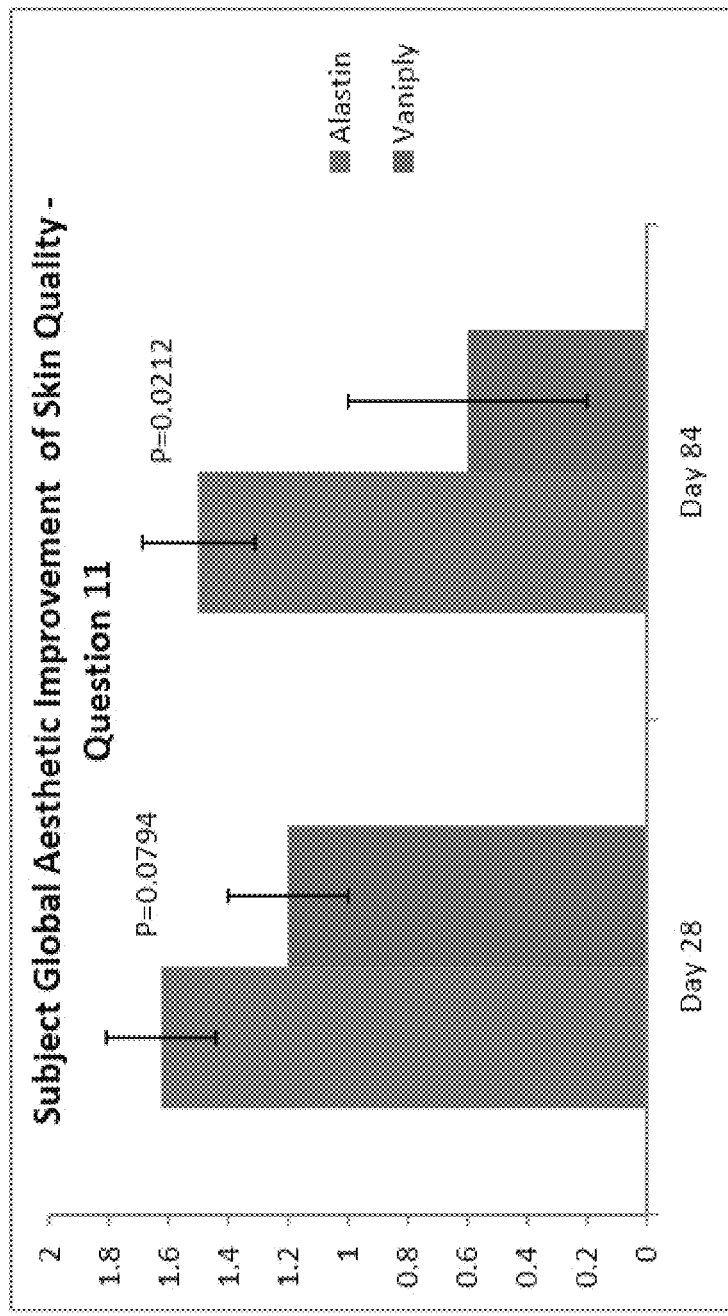
Figure 19G:
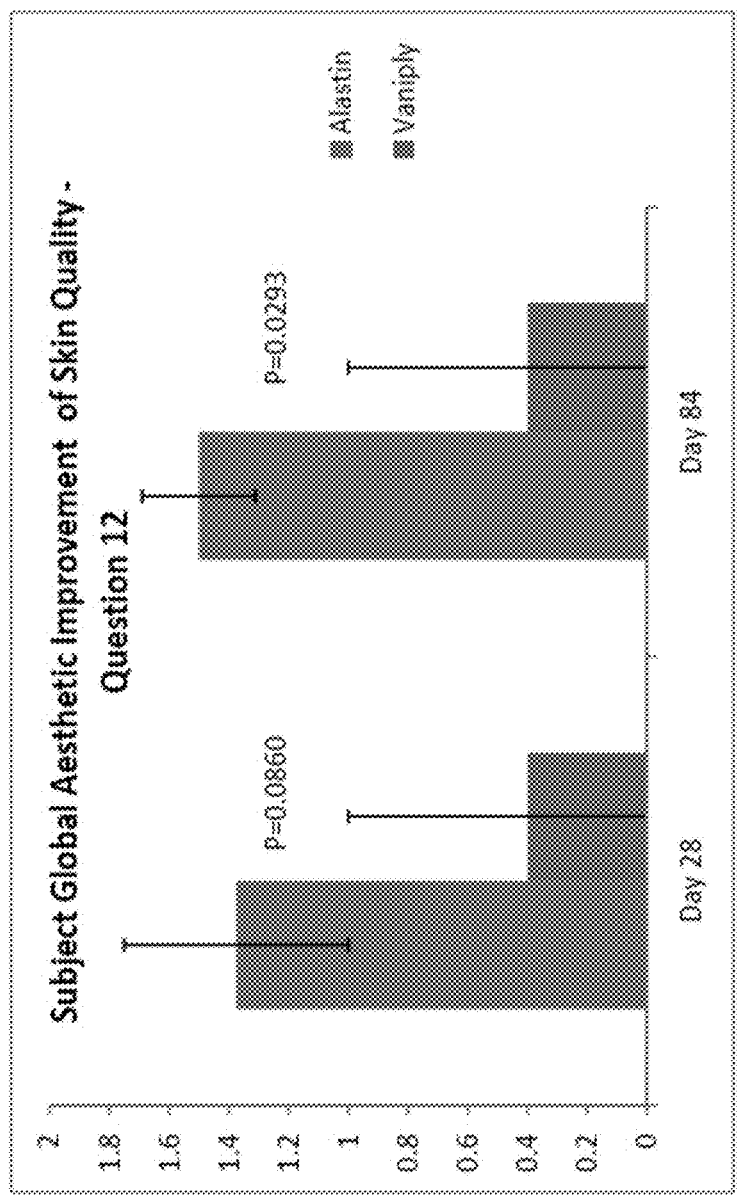
Figure 19H:
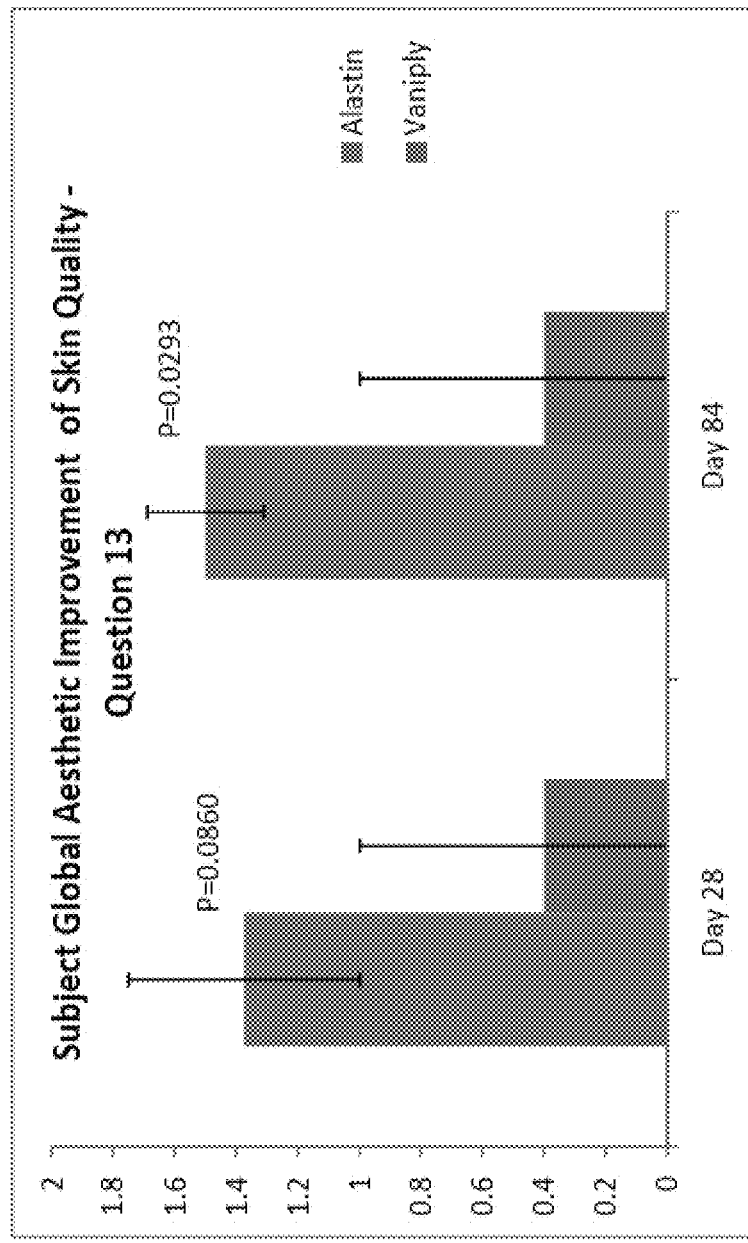

The results of the answers to Questions 11, 12, and 13 are presented in FIG. 19F, FIG. 19G, and FIG. 19H, respectively.

No Significant Differences

Investigator Evaluation of Side Effects—Crusting: Crusting was worse for the SOC group on Days 1, 4 and 7; however worse for the Alastin group on Day 3. Due to the healing properties of the Alastin Occlusive Moisturizer, the Crust has a better adherence to the face and comes off between Days 3 and 4, thus day 4 shows a dramatic reversal with a 35% improved appearance over SOC at day 4. The Investigator evaluation of side effects-crusting are presented in FIG. 19I.

The above description presents the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention. While the disclosure has been illustrated and described in detail in the drawings and foregoing description, such illustration and description are to be considered illustrative or exemplary and not restrictive.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article 'a' or 'an' does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases 'at least one' and 'one or more' to introduce claim recitations. However, the use of such phrases should not be construed to imply that the introduction of a claim recitation by the indefinite articles 'a' or 'an' limits any particular claim containing such introduced claim recitation to embodiments containing only one such recitation, even when the same claim includes the introductory phrases 'one or more' or 'at least one' and indefinite articles such as 'a' or 'an' (e.g., 'a' and/or 'an' should typically be interpreted to mean 'at least one' or 'one or more'); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of 'two recitations,' without other modifiers, typically means at least two recitations, or two or more recitations). Furthermore, in those instances where a convention analogous to 'at least one of A, B, and C, etc.' is used, in general such a construction is intended in the sense one having skill in the art would understand the convention (e.g., 'a system having at least one of A, B, and C' would include but not be limited to systems that have A alone, B alone, C alone, A and B together, A and C together, B and C together, and/or A, B, and C together, etc.). In those instances where a convention analogous to 'at least one of A, B, or C, etc.' is used, in general such a construction is intended in the sense one having skill in the art would understand the convention (e.g., 'a system having at least one of A, B, or C' would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase 'A or B' will be understood to include the possibilities of 'A' or 'B' or 'A and B.'

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A topical composition for promoting skin restoration around an eye, comprising:
   a tripeptide-1 present at 1-10 ppm;
   one or more peptides selected from a dipeptide, a tripeptide, or a tetrapeptide;
   a hexapeptide-12 present at 1-10 ppm; and
   Squalene,
   wherein the topical composition is configured to promote restoration of damaged skin or aging skin around the eye.

2. The topical composition of claim 1, wherein the tripeptide-1 comprises palmitoyl tripeptide-1, myristoyl tripeptide-1, or a combination thereof.

3. The topical composition of claim 1, wherein the hexapeptide-12 comprises palmitoyl hexapeptide-12, myristoyl hexapeptide-12, or a combination thereof.

4. The topical composition of claim 1, wherein the Squalene is present at 0.01-5.0 wt. %.

5. The topical composition of claim 1, wherein the Squalene is present at 0.1-1.0 wt. %.

6. The topical composition of claim 1, wherein the Squalene is present at no more than 1.0 wt. %.

7. The topical composition of claim 1, wherein the Squalene is present at 0.25 wt. %.

8. The topical composition of claim 1, further comprising one or more additional ingredients selected from the group consisting of disodium EDTA, niacinamide, caprylyl glycol, caprylhydroxamic acid, glycerin, phenoxyethanol, ethylhexylglycerin, betaine, propanediol, phospholipids, isopropyl palmitate, polyacrylate-13, polysorbate 20, Dunaliella salina extract, phytosterols, hydrolyzed pea protein, *Butyrospermum parkii* (Shea) butter, ceramide NP, tocopherol, butylene glycol, caprylyl methicone, ascorbyl palmitate, or combinations thereof.

9. The topical composition of claim 1, wherein the composition is aqueous.

* * * * *